(12) United States Patent
Chen et al.

(10) Patent No.: US 11,008,292 B2
(45) Date of Patent: May 18, 2021

(54) FGFR4 INHIBITOR AND PREPARATION METHOD AND USE THEREOF

(71) Applicant: GUANGDONG ZHONGSHENG PHARMACEUTICAL CO., LTD, Guangdong (CN)

(72) Inventors: Zhengxia Chen, Shanghai (CN); Chaofeng Long, Guangdong (CN); Yang Zhang, Shanghai (CN); Xiaoxin Chen, Guangdong (CN); Yikai Wang, Shanghai (CN); Meibi Dai, Shanghai (CN); Zhuowei Liu, Guangdong (CN); Haixia Zhao, Shanghai (CN); Xing Liu, Guangdong (CN); Guoping Hu, Shanghai (CN); Jian Li, Shanghai (CN); Shuhui Chen, Shanghai (CN)

(*) Notice: Subject to any disclaimer, the term of this patent is extended or adjusted under 35 U.S.C. 154(b) by 0 days.

(21) Appl. No.: 16/461,373

(22) PCT Filed: Nov. 17, 2017

(86) PCT No.: PCT/CN2017/111634
§ 371 (c)(1),
(2) Date: May 16, 2019

(87) PCT Pub. No.: WO2018/090973
PCT Pub. Date: May 24, 2018

(65) Prior Publication Data
US 2020/0062716 A1   Feb. 27, 2020

(30) Foreign Application Priority Data

Nov. 17, 2016 (CN) .......................... 201611012431.5

(51) Int. Cl.
*C07D 213/53* (2006.01)
*C07D 239/42* (2006.01)
*A61P 35/00* (2006.01)
*A61K 45/06* (2006.01)

(52) U.S. Cl.
CPC ............ *C07D 239/42* (2013.01); *A61P 35/00* (2018.01); *C07D 213/53* (2013.01); *A61K 45/06* (2013.01)

(58) Field of Classification Search
CPC ..................... C07D 213/53; C07D 239/42
See application file for complete search history.

(56) References Cited

U.S. PATENT DOCUMENTS

2008/0300248 A1   12/2008   Guo et al.

FOREIGN PATENT DOCUMENTS

| CN | 102731485 A | 10/2012 |
|---|---|---|
| CN | 105899490 A | 8/2016 |
| WO | 2007082434 A1 | 7/2007 |
| WO | 2012136099 A1 | 10/2012 |
| WO | 2014139465 A1 | 9/2014 |
| WO | 2015057938 A1 | 4/2015 |
| WO | 2016115412 A1 | 7/2016 |
| WO | 2016164703 A1 | 10/2016 |
| WO | WO 2019/085893 | * 5/2019 |

OTHER PUBLICATIONS

International Search Report and Written opinion of PCT/CN2017/111634 dated Feb. 14, 2018.
English translation of Chinese priority application No. 201611012431.5.
Cheng Mo et al., "2-Aminopyrimidine derivatives as new selective fibroblast growth factor receptor 4 (FGFR4) inhibitors", ASC Med. Chem.Lett., 8(5), 2017.
Dec. 14, 2020 Korean 1st Office Action issued in Korean Patent Application No. 10-2019-7016780.

* cited by examiner

*Primary Examiner* — Brian E McDowell
(74) *Attorney, Agent, or Firm* — Houston Beshining Law Office PLLC; Liangang Ye

(57) ABSTRACT

Provided are a class of compounds as shown in formula (I) as FGFR4 inhibitors, and pharmaceutically acceptable salts thereof, preparation methods therefor and the use thereof in the preparation of drugs for treating FGFR4-related diseases.

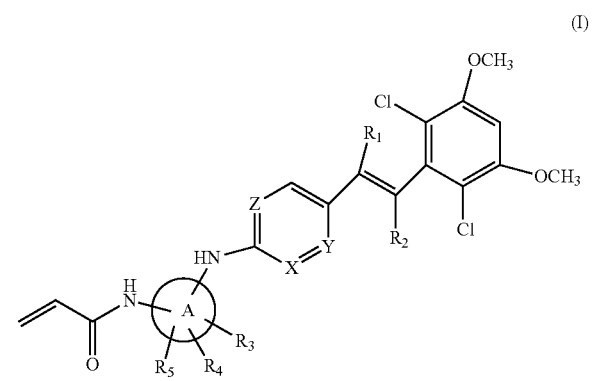

15 Claims, No Drawings

FGFR4 INHIBITOR AND PREPARATION METHOD AND USE THEREOF

CROSS REFERENCE TO RELATED APPLICATIONS

The present application is a National Stage of International Application No. PCT/CN2017/111634, filed on Nov. 17, 2017, which claims priority of the Chinese Patent Application No. CN 201611012431.5 filed on Nov. 17, 2016, the contents of which are incorporated herein by reference in their entireties.

TECHNICAL FIELD

The present invention relates to a class of compounds used as FGFR4 inhibitors, and the use thereof in the preparation of drugs for treating FGFR4-related diseases. In particular, the present invention relates to a compound as shown in formula (I) and pharmaceutically acceptable salts thereof.

BACKGROUND

Fibroblast growth factor receptor 4 (FGFR4) is a kind of human protein encoded by FGFR4 gene. This protein is a member of the fibroblast growth factor receptor family the homology of amino acid sequences among FGFR1-4 members is very high, with a high degree of similarity which is a glycoprotein composed of extracellular immunoglobulin (Ig)—like domains, hydrophobic transmembrane domains and a cytoplasm portion including tyrosine kinase domains. The binding of extramembrane domain to FGF leads to the dimerization of FGFR, autophosphorylation occurs on the receptors, which activates the downstream signal path, and finally affects the division and variation of cells.

FGFR4 is distinctly different from FGFR1-3 in terms of genetic structure, which is of a specific structure of cysteine 552 (CYS552), thus being capable of selectively inhibiting FGFR4, while not inhibiting the development of FGFR1-3 inhibitors, and being capable of reducing the potential toxicity caused by FGFR1-3 inhibition; it has been demonstrated from recent studies that FGFR4-FGF19 signal axes are closely related to liver cancer, renal cancer, colon cancer, breast cancer, etc., allowing FGFR4 become one of potential targets for treating liver cancer, renal cancer, colon cancer, breast cancer, etc.

In clinical, FGFR4 inhibitors are not limited to be used for treating liver cancer with high expression of FGFR4, also may be applied to other solid tumors with abnormal FGFR4 signal paths, meanwhile there is also a possibility of being used in combination with other therapies. Therefore, the development of FGFR4 inhibitors has a more extensive market space and application prospect.

Contents of the Invention

The present invention provides a compound as shown in formula (I), a pharmaceutically acceptable salt or a tautomer thereof,

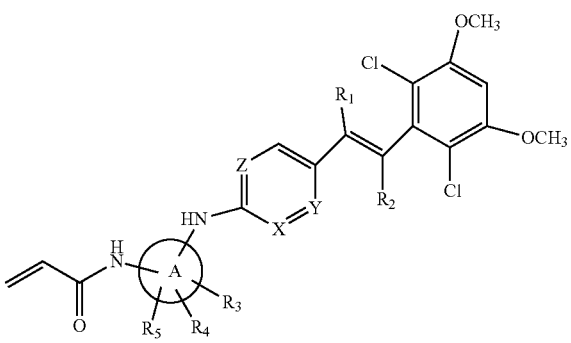

wherein, each of X, Y, Z is independently selected from the group consisting of C(R) and N;

one of $R_1$, $R_2$ is F, and the other is H or $CH_3$;

A-ring is selected from the group consisting of phenyl, 5-6 membered cycloalkyl and 5-6 membered heterocycloalkyl;

each of $R_3$, $R_4$ and $R_5$ is independently selected from the group consisting of H, F, Cl, or selected from the group consisting of $C_{1-3}$ alkyl, $C_{1-3}$ alkoxy, $C_{1-3}$ alkyl-C(=O)— and 5-6 membered heterocycloalkyl which are optionally substituted with 1, 2 or 3 R;

R is selected from H, or selected from the group consisting of $C_{1-3}$ alkyl, $C_{1-3}$ alkyl-C(=O)— and 5-6 membered heterocycloalkyl which are optionally substituted with 1, 2 or 3 R';

R' is selected from the group consisting of $CH_3$ and $CH_2CH_3$;

"hetero-" in the 5-6 membered heterocycloalkyl is each independently selected from the group consisting of —NH—, —O— and N;

in any one of the above cases, the number of heteroatoms or heteroatomic groups is each independently selected from the group consisting of 1, 2 and 3.

In some embodiments of the present invention, the above $R_1$ is F, $R_2$ is H or $CH_3$, and other variables are as defined in the present invention.

In some embodiments of the present invention, the above $R_1$ is H or $CH_3$, $R_2$ is F, and other variables are as defined in the present invention.

In some embodiments of the present invention, the above R is H, or selected from the group consisting of $CH_3$, $CH_2CH_3$,

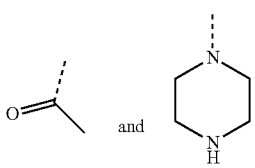

which are optionally substituted with 1, 2 or 3 R', and other variables are as defined in the present invention.

In some embodiments of the present invention, the above R is selected from the group consisting of H, $CH_3$, $CH_2CH_3$,

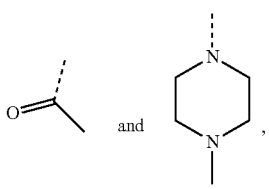 and 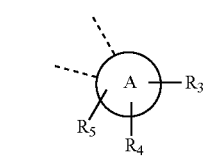, and other variables are as defined in the present invention.

In some embodiments of the present invention, the above A-ring is selected from the group consisting of phenyl, cyclohexyl, cyclopentyl, tetrahydropyranyl, tetrahydrofuryl and pyrrolidinyl, and other variables are as defined in the present invention.

In some embodiments of the present invention, the above A-ring is selected from the group consisting of

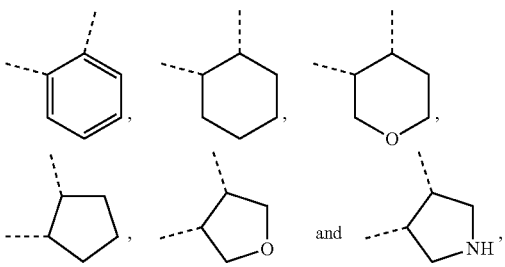

and other variables are as defined in the present invention.

In some embodiments of the present invention, the above structural unit

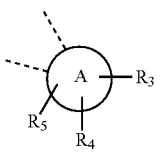

is selected from the group consisting of

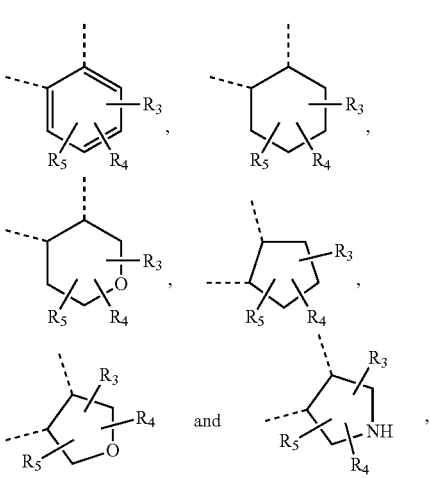

and other variables are as defined in the present invention.

In some embodiments of the present invention, the above structural unit

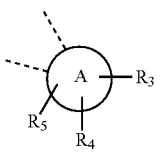

is selected from the group consisting of

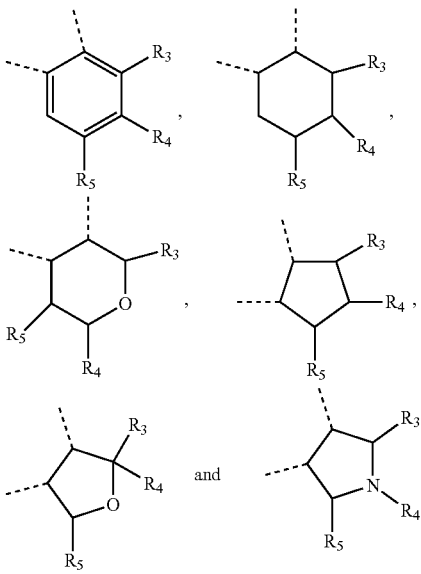

and other variables are as defined in the present invention.

In some embodiments of the present invention, the above structural unit

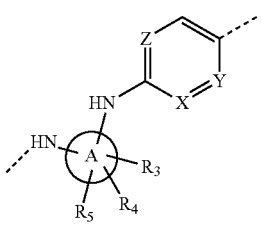

is selected from the group consisting of

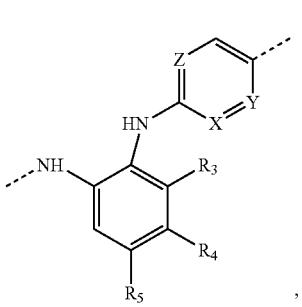

-continued

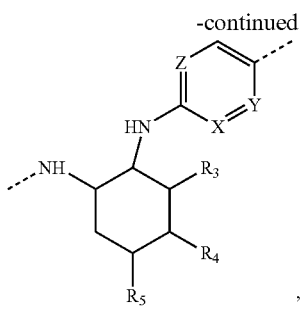

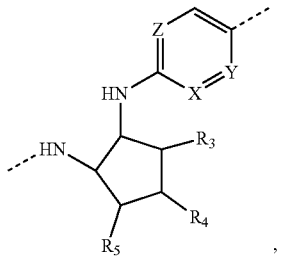

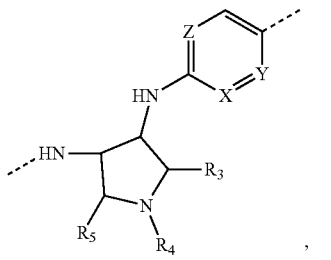

and other variables are as defined in the present invention.

In some embodiments of the present invention, the above structural unit is selected from the group consisting of

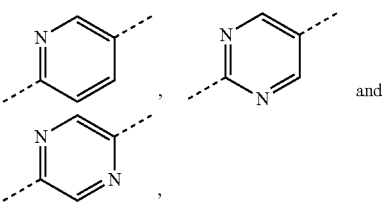

and other variables are as defined in the present invention.

In some embodiments of the present invention, each of $R_3$, $R_4$, $R_5$ is independently selected from the group consisting of H, F, Cl, or selected from the group consisting of methyl, ethyl, $C_{1-3}$ alkoxy, $C_{1-3}$ alkyl-C(=O)— and piperazinyl which are optionally substituted with 1, 2 or 3 R, and other variables are as defined in the present invention.

In some embodiments of the present invention, each of $R_3$, $R_4$, $R_5$ is independently selected from the group consisting of H, F, Cl, or selected from the group consisting of $CH_3$,

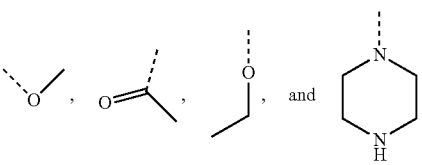

which are optionally substituted with 1, 2 or 3 R, and other variables are as defined in the present invention.

In some embodiments of the present invention, each of $R_3$, $R_4$, $R_5$ is independently selected from the group consisting of H, F, Cl, $CH_3$,

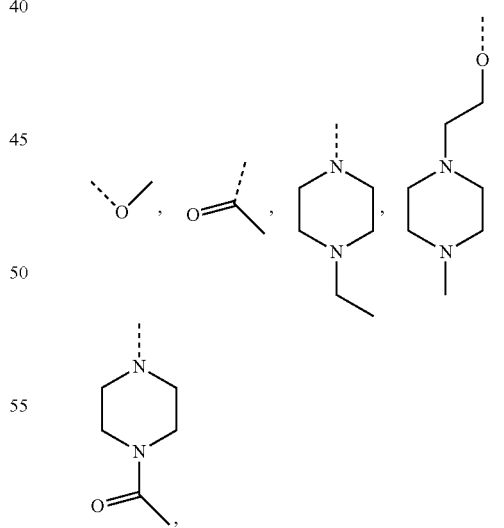

and other variables are as defined in the present invention.

In some embodiments of the present invention, the above $R_3$ is selected from the group consisting of H, F, Cl and $CH_3$, and other variables are as defined in the present invention.

In some embodiments of the present invention, the above $R_4$ is selected from the group consisting of H, F, Cl,

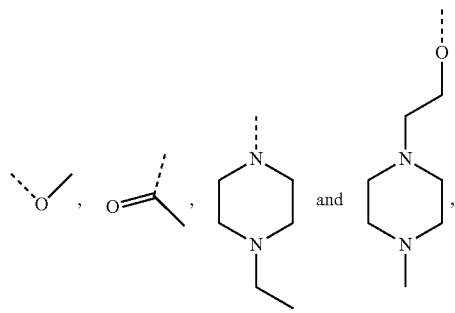

and other variables are as defined in the present invention.

In some embodiments of the present invention, the above $R_5$ is selected from the group consisting of H, F, Cl,

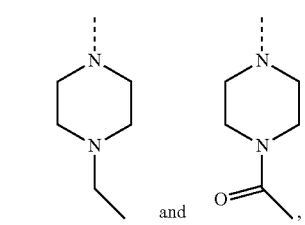

and other variables are as defined in the present invention.

Some other embodiments of the present invention are forming by any combination of the above variables.

In some embodiments of the present invention, the above compound, pharmaceutically acceptable salt or the tautomer thereof are selected from the group consisting of

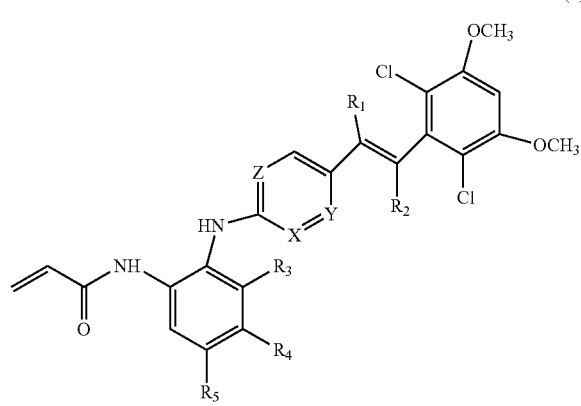

(2)

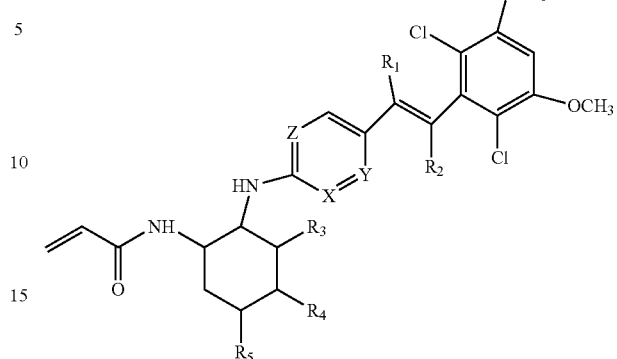

(3)

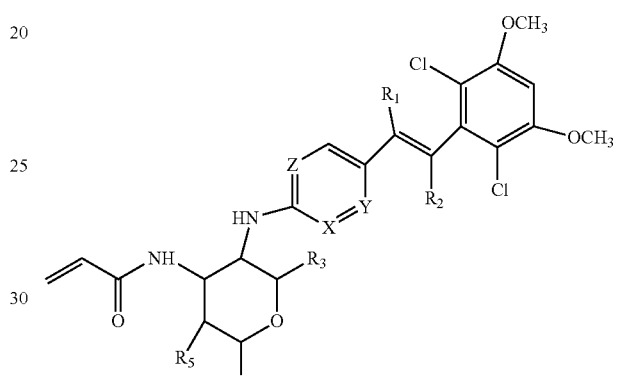

(3)

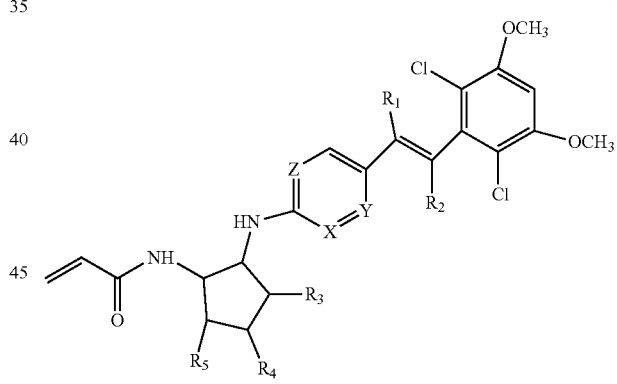

(4)

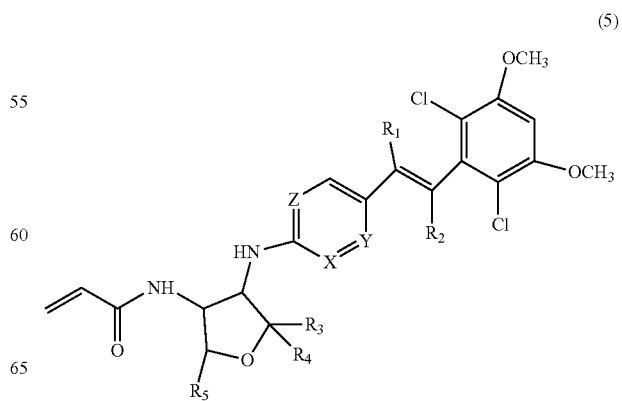

(5)

-continued (6)

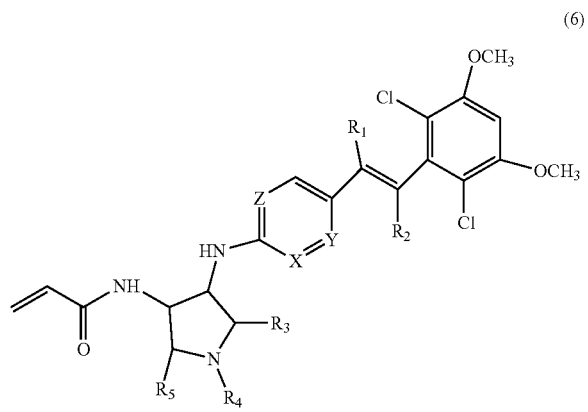

wherein, the definitions of $R_1$, $R_2$, $R_3$, $R_4$, $R_5$, Z, X, Y are as defined in the present invention.

In some embodiments of the present invention, the structural unit

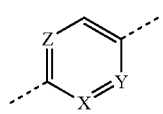

of the above compound as shown in formula (I) is selected from the group consisting of

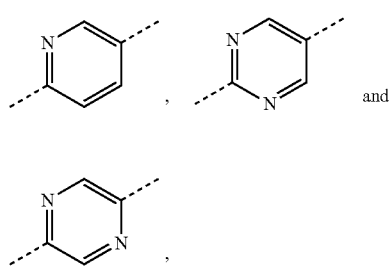

and and other variables are as defined in the present invention.

The present invention further provides the compound, the pharmaceutically acceptable salt or the tautomer thereof, which are selected from the group consisting of -continued

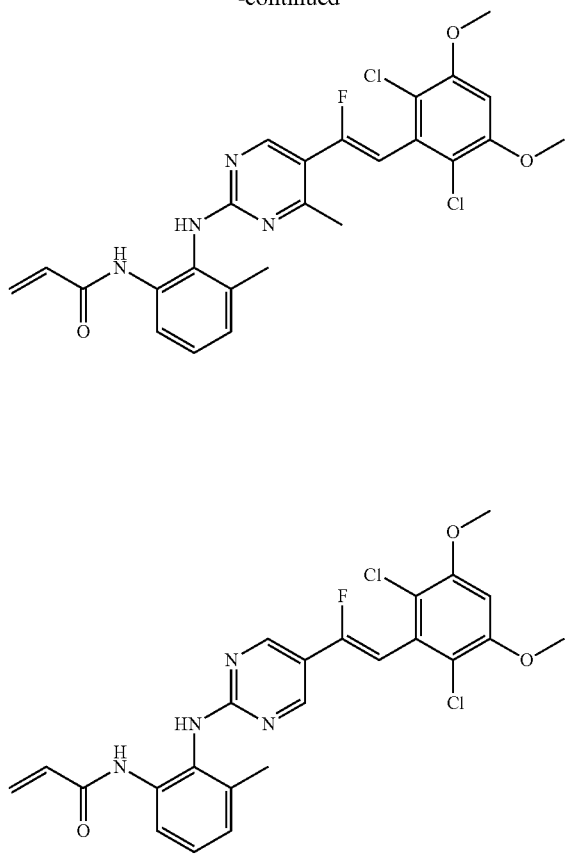

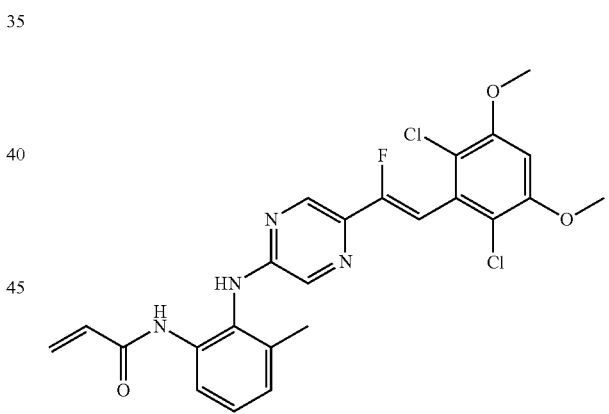

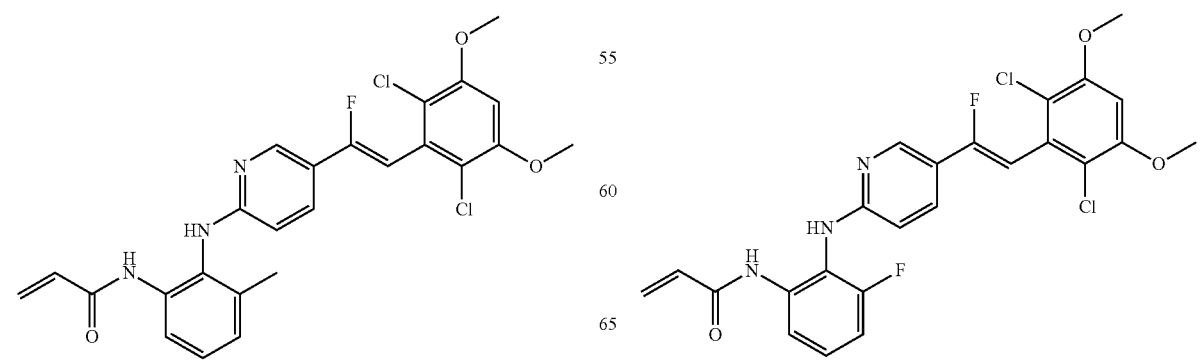

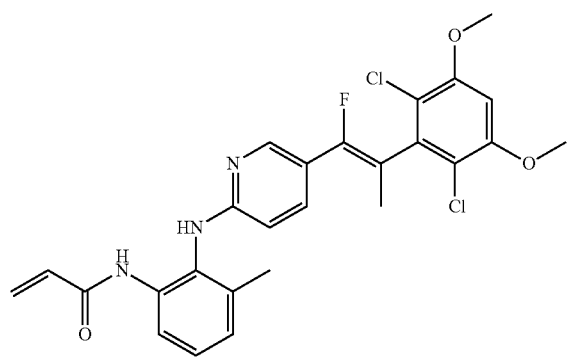
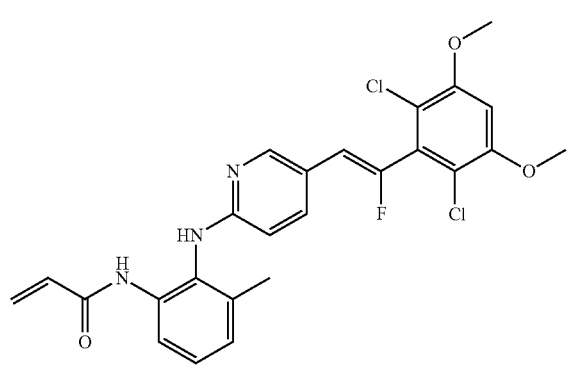
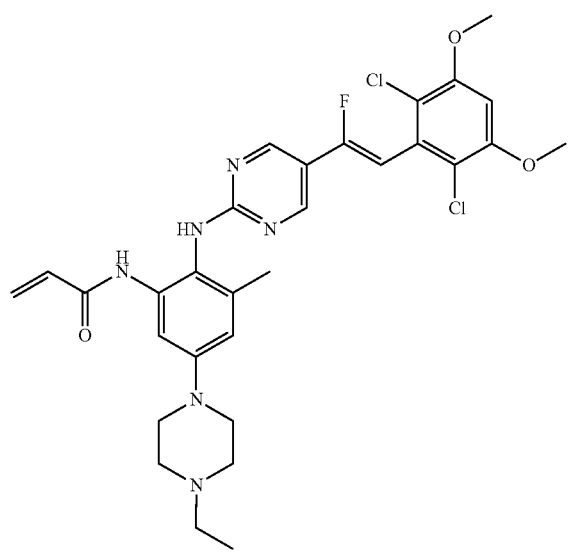
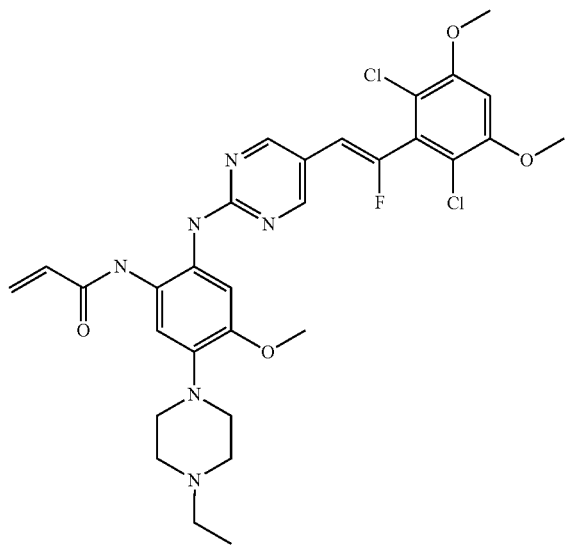
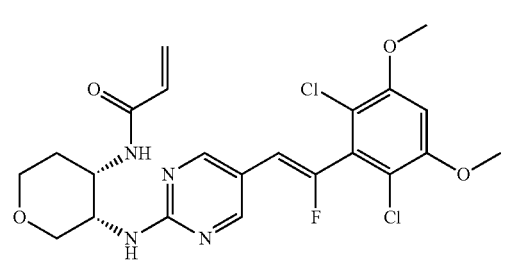

13
-continued
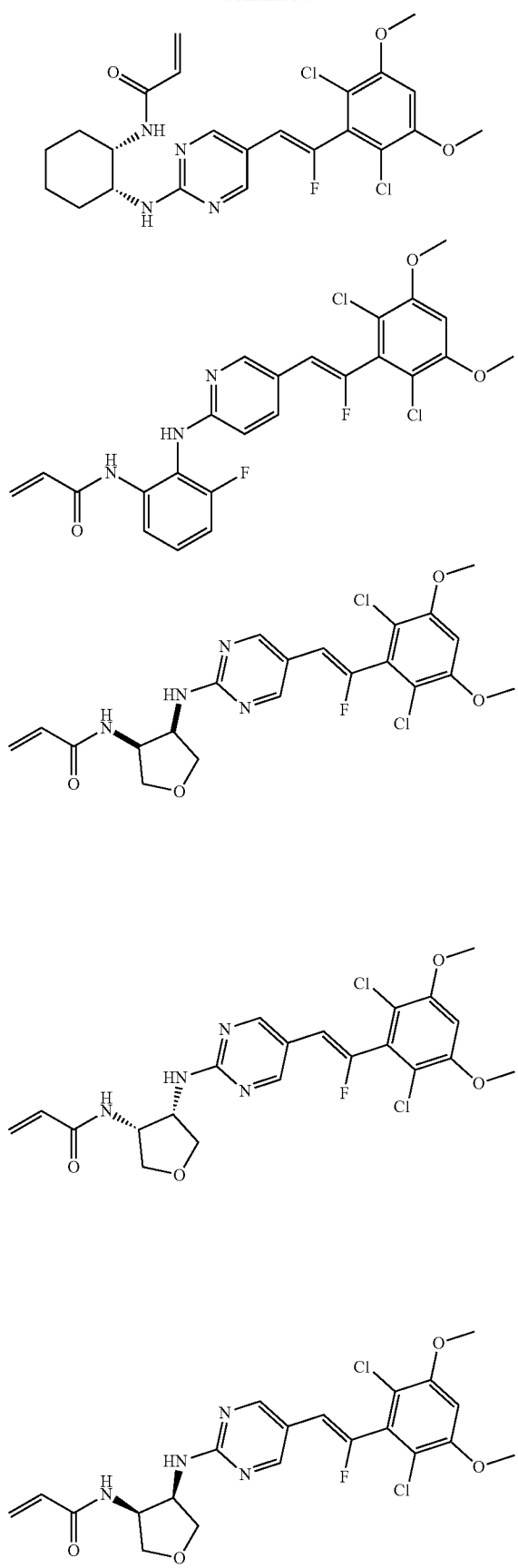
14
-continued
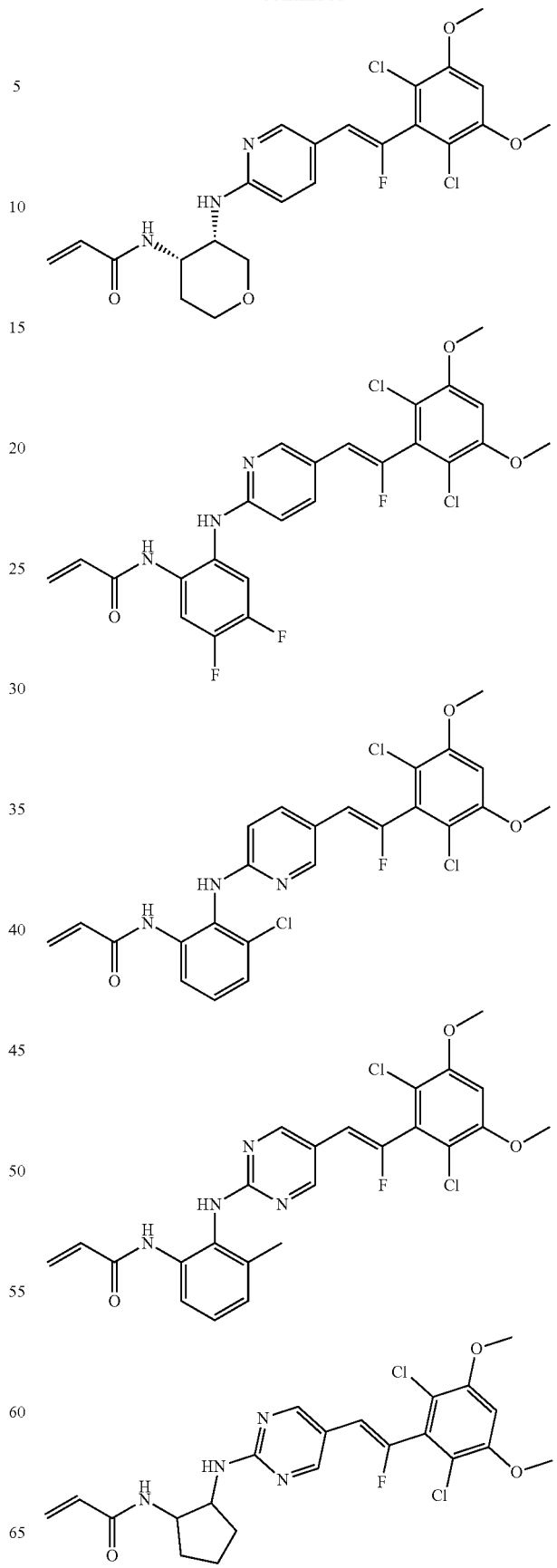

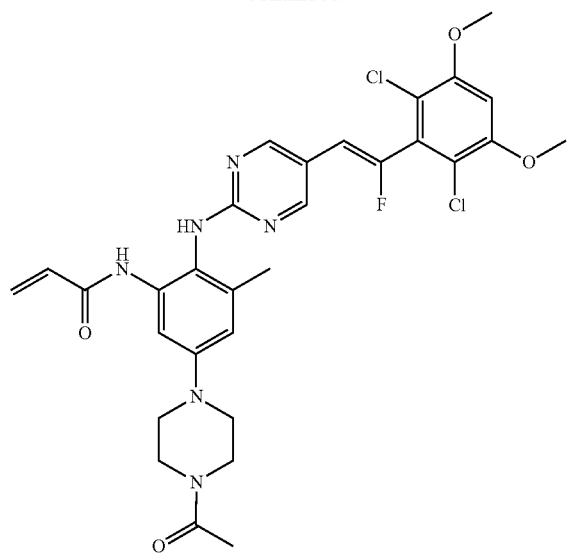
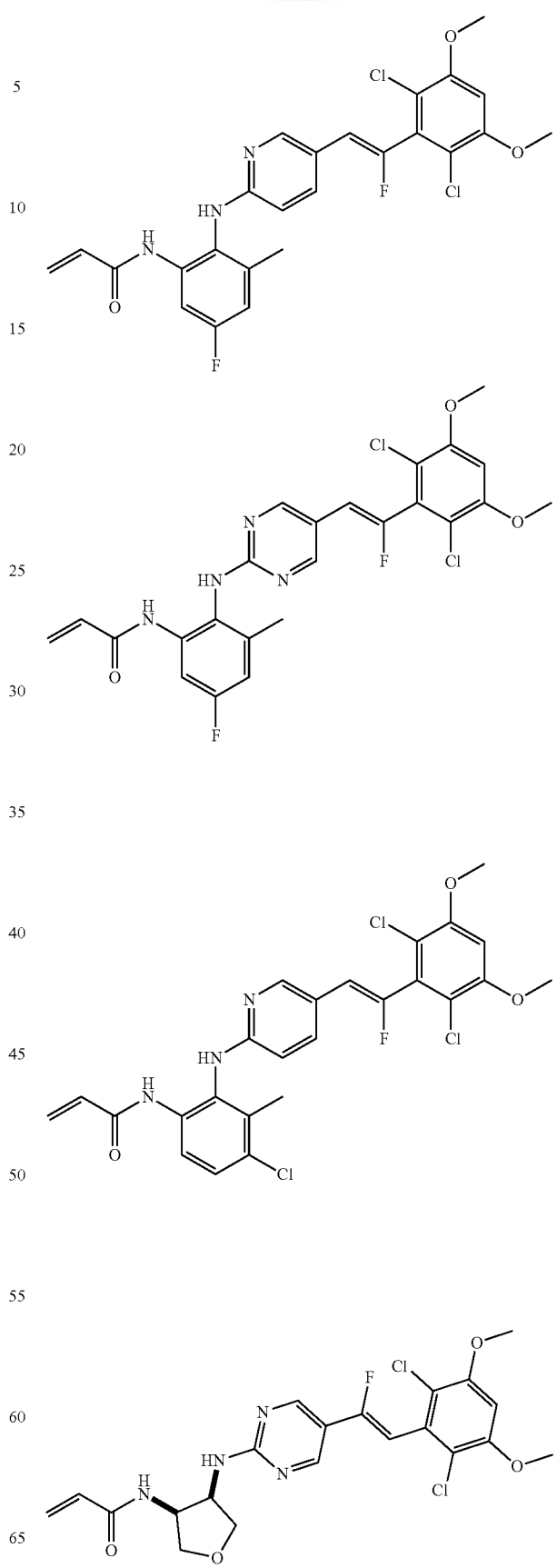

-continued

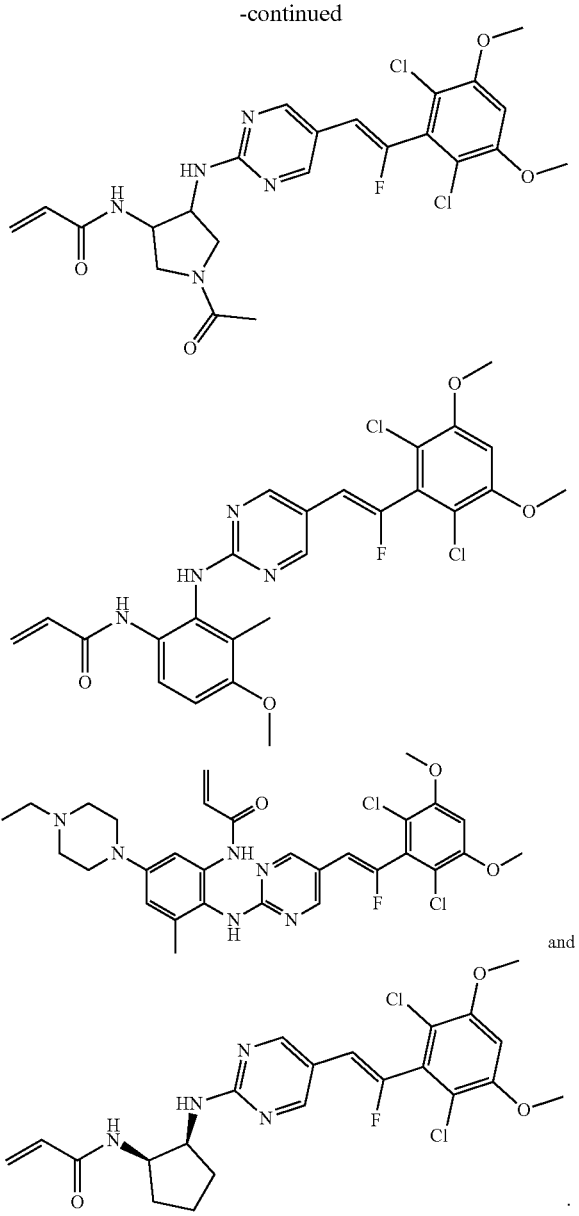

and

The present invention further provides a pharmaceutical composition, comprising a therapeutically effective amount of the above compound or the pharmaceutically acceptable salt thereof as the active ingredients, as well as pharmaceutically acceptable carrier.

The present invention further provides a use of the above compound or the pharmaceutically acceptable salt thereof in the preparation of drugs for treating FGFR4-related diseases.

The present invention further provides a use of the above composition in the preparation of drugs for treating FGFR4-related diseases.

In some embodiments of the present invention, the above use is characterized in that the drugs are useful for treating liver cancer or gastric cancer.

TECHNICAL EFFECTS

A series of the present compounds with high FGFR4 selectivity could be derived from the mother nuclear structure of acrylamide and fluorinated olefinic bond, which have superior inhibitory activities on FGFR4 kinases, while without activities on subtype FGFR1 kinases, the superiority of which against FGFR4 kinases is at least more than ten or a hundred times than that of subtype FGFR1 kinases. It was further found that in the structure of dimethoxy dichlorobenzene, the dichloro could enhance the inhibitory activity on FGFR4 greatly; for embodiment 1, the activity was enhanced by 70 times compared with that in the control example 1; a fluorine atom was introduced into the olefinic bond, and the fluorine atom was close to dichloroaniline, which could enhance the activity on target FGFR4, for example, the activity in embodiment 15 was enhanced by near 9 times compared with that in the control example 2, and the activity in embodiment 19 was enhanced by near 9 times compared with that in the control example 3; the fluorinated olefinic structure of the inventive compound, compared with benzyl ether structure, could enhance the metabolic stabilities of the drugs greatly, meanwhile enhance the oral absorption bioavailability of the drugs greatly; and the compound of the present invention have superior antitumor activities and have good effects on treating neoplastic diseases of various mammals (including human), such as liver cancer, gastric cancer, etc.

Definitions and Explanations

Unless stated otherwise, the following terms and phrases as used herein are intended to have the following meanings. A particular term or phrase should not be deemed indefinite or unclear without a special definition, but should be understood in the ordinary sense. When a trade name is used herein, it is intended to refer to the corresponding commercially available product thereof or the active ingredients thereof.

The term "pharmaceutically acceptable" as used herein means that by clinically reliable judgement, the compounds, materials, compositions and/or dosage forms are suitable for being used in contact with human and animal tissues without excessive toxicities, irritations, allergic reactions, or other problems or complications, and are commensurate with a reasonable benefit/rist ratio.

The term "pharmaceutically acceptable salt" refers to a salt of the compound of the present invention, which are prepared from a compound having specific substituent(s) found in the present invention with a relatively non-toxic acid or base. When the compound of the present invention comprises a relatively acidic functional group, it is possible to obtain a base addition salt by means of contacting a sufficient amount of base with a neutral form of such compound in a pure solution or a suitable inert solvent. Pharmaceutically acceptable base additional salts comprise sodium, potassium, calcium, ammonium, organic amine or magnesium salts, or the like. When the compound of the present invention comprises relatively basic functional groups, it is possible to obtain an acid additional salt by means of contacting a sufficient amount of acid with a neutral form of such compounds in a pure solution or a suitable inert solvent. Examples of pharmaceutically acceptable acid addition salts comprise inorganic acid salts, including, e.g., hydrochloride, hydrobromide, nitrate, carbonate, bicarbonate, phosphorate, monohydrogen phosphate, dihydrogen phosphate, sulfate, hydrosulfate, hydroiodate, phosphite, etc.; and organic acid salts, including, e.g., acetate, propionate, isobutyrate, maleate, malonate, benzoate, succinate, suberate, fumarate, lactate, mandelate, phthalate, benzenesulfonate, tosilate, citrate, tartarate and methanesulfonate and the like; and salts of amino acids (e.g., arginine or the like), as well as salts of organic acids, e.g., glucuronic acid or the like (see Berge et al., "Pharmaceutical Salts", Journal of Pharmaceutical Science 66: 1-19 (1977)). Some particular compounds of the present invention have basic and acid functional groups, and thus can be converted to any one of base or acid additional salt.

Preferably, the neutral forms of the compounds can be regenerated by a conventional means of contacting a salt with a base or an acid, followed by isolating the parent compound. The parent form of a compound differs from its various salt forms in terms of certain physical properties, e.g., different solubilities in a polar solvent.

The term "pharmaceutically acceptable salt" as used herein belong to the derivatives of the compound of the present invention, wherein the parent compound is modified by forming a salt with an acid or a base. Examples of pharmaceutically acceptable salts comprise, but not limited to, inorganic or organic acid salts of basic groups, such as amines; basic metal or organic salts of acidic groups, such as, carboxylate. Pharmaceutically acceptable salts comprise conventional non-toxic salts or quandary ammonium salts of parent compounds, such as, salts formed from non-toxic inorganic or organic acids. Conventional non-toxic salts comprise, but not limited to those derived from inorganic and organic acids selected from the group consisting of 2-acetoxybenzoic acid, 2-hydroxyethanesulfonic acid, acetic acid, ascorbic acid, benzenesulfonic acid, benzoic acid, hydrocarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionate, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalacturon, propionic acid, salicylic acid, stearic acid, folinate, succinic acid, aminosulfonic acid, p-aminobenzenesulfonic acid, sulfuric acid, tannin, tartaric acid and p-toluenesulfonic acid.

The pharmaceutically acceptable salt of the present invention may be chemically synthesized from a parent compound having an acidic or a basic functional group via a conventional chemical method. In general, such salts are prepared from reacting these compounds in forms of free acid or base with a stoichiometric amount of a suitable base or acid in water or an organic solvent or a mixture thereof. Typically, non-aqueous mediums, e.g., ether, ethyl acetate, ethanol, isopropanol, or acetonitrile or the like, are preferred.

Some compounds of the present invention may have an asymmetric carbon atom (the optical center) or a double bond. Racemates, diastereomers, geometric isomers, and individual isomers are all encompassed within the scope of the present invention.

Unless stated otherwise, the wedge bond and dashed bond ( ▰ ▰ ) are used to indicate the absolute configuration of a stereocenter; ▰ ▰ is used to indicate the relative configuration of a stereocenter. When the compounds as described herein comprise an olefinic double bond or other geometrically asymmetric centers, unless specified otherwise, they comprise E-, Z-geometrical isomers. Similarly, all the tautomers are encompassed within the scope of the present invention.

The compounds of the present invention may be present in specific geometric or stereoisomeric forms. It is envisioned that all forms of the compounds as described in the present invention, including cis- and trans-isomers, (−)- and (+)-enantiomers, (R)- and (S)-enantiomers, diastereomers, (D)-isomers, (L)-isomers, as well as racemic mixtures thereof and other mixtures, such as, enantiomer- or diastereomer-enriched mixtures, are encompassed within the scope of the present invention. Substituents, such as, alkyl, etc., may comprise additional asymmetric carbon atoms. All of these isomers and mixtures thereof are encompassed within the scope of the present invention.

Chiral synthesis or chiral reagents or other conventional technologies may be used to prepare optically active (R)- and (S)-isomers as well as D- and L-isomers. If one enantiomer of a compound of the present invention is desired, it can be prepared by asymmetric synthesis or derivatization with a chiral auxiliary, in which the resulting mixture of diastereometers is isolated, and the auxiliary group is cleaved to provide the desired pure enantiomer. Alternatively, if the molecule contains a basic functional group (e.g., amino) or an acidic functional group (e.g., carboxyl), it may be reacted with a suitable optically active acid or base to form salts of diastereomers, which are in turn subjected to diastereoisomers resolution via a conventional method as well known in the art, and recovered to give pure enantiomers. Furthermore, the separation between enantiomers and diastereoisomers is usually accomplished by chromatography, which utilizes a chiral stationary phase, and optionally combined with a chemical derivation method (e.g., producing a carbamate from amine)

With respect to drugs or pharmacologically active agents, the term "effective amount" or "therapetically effective amount" refers to the sufficient amount of drugs or agents which is not toxic but can achieve the desired effect. As for the oral dosage forms of the present invention, the "effective amount" of an active substance in the composition refers to the amount required to achieve the desired effect when used in combination with another active substance in the composition. The determination of the effective amount varies from person to person, depending on the age and general condition of the subject, and also depending on the particular active substance. The appropriate effective amount in individual cases may be determined by a person skilled in the art via conventional experiments.

The term "active ingredient", "therapeutic agent", "active substance" or "active agent" refers to a chemical entity which can effectively treat the target disorders, diseases, or conditions.

"Optional" or "optionally" means that the subsequently described events or conditions may but do not have to occur, and the description includes both the cases that the event or condition occurs and the cases that the event or condition does not occur.

The term "substituted" means that any one or more hydrogen atoms attached to a particular atom are substituted with a substituent, and heavy hydrogen and variants of hydrogen may be included, as long as the valence of the particular atom is normal and the substituted compound is stable. When the substituent is a ketone group (i.e., =O), it means that two hydrogen atoms are substituted. Ketone substitution would not occur on an aromatic group. The term "optionally substituted" means that it is may or may not be substituted, and unless specified otherwise, the type and number of substituents may vary randomly as long as they are chemically achievable.

When any variables (e.g., R) occur in the composition or structure of a compound more than once, their definitions are independent in each case. Therefore, for example, if a group is substituted with 0-2 R, the group may be optionally substituted with at most two Rs, and the substituent R is independently selected in each case. Moreover, a combination of a substituent and/or variants thereof is allowable only if such combination leads to a stable compound.

When the number of the linking group is 0, such as —(CRR)$_0$—, it means that the linking group is a single bond.

When a variable is selected from the group consisting of a single bond, it means that the two groups linked thereby are directly linked, e.g., when L in in A-L-Z represents a single bond, this structure is actually A-Z.

When a substituent is null, it means that the substituent is absent, for instance, when X in A-X is null, it means that the structure is actually A. When the bond of a substituent may be cross-linked to two atoms in a ring, the substituent may be bonded to any atom in the ring. When a recited substituent does not indicate through which atom it is attached to the compound included but not specifically mentioned in the general formula of the chemical structure, the substituent may be bonded through any atom therein. The combination of a substituent and/or variants thereof is allowable only if such combination leads to a stable compound. For example, the structural unit

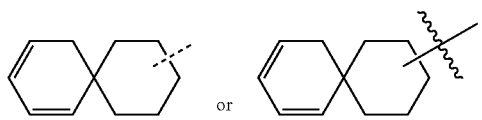

indicates that it may be substituted at any position of cyclohexyl or cyclohexadiene.

Unless specified otherwise, the term "hetero-" means heteroatom or heteroatomic group (i.e., atomic group containing heteroatom), including atoms other than carbon (C) and hydrogen (H) as well as atomic groups containing these heteroatoms, including, e.g., oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless specified otherwise, "ring" represents substituted or unsubstituted cycloalkyl, heterocycloalkyl, cycloalkenyl, heretocycloalkenyl, cycloalkynyl, heretocycloalkynyl, aryl or heteroaryl. The so-called ring comprises mono ring, dual ring, Spiro ring, fused ring, or bridge ring. The atomic number in the ring is typically defined as the membered number of the ring, e.g., "5-7 membered ring" indicates that there are 5-7 atoms in a cyclized arrangement. Unless specified otherwise, the ring contains optionally 1-3 heteroatoms. Thus, "5-7 membered ring" comprises, e.g., phenyl, pyridinyl and piperidyl; and on the other hand, the term "5-7-membered heterocycloalkyl" comprises pyridyl and piperidyl, but does not comprises phenyl. The term "ring" further comprises a ring system containing at least one ring, of which each "ring" meets independently the above definition.

Unless specified otherwise, the term "heterocycle" or "heterocyclyl" is intended to mean stable mono-, bi-, or tri-cycle containing heteroatom or heteroatomic group that may be saturated, partially unsaturated or unsaturated (aromatic), and may comprise carbon atoms and 1, 2, 3 or 4 ring heteroatoms independently selected from the group consisting of N, O and S, wherein any of the above heterocycles may be fused to a phenyl ring to form a dual ring. Nitrogen and sulfur heteroatoms may be optionally oxidized (i.e., NO and S(O)$_p$, wherein p is 1 or 2). Nitrogen atoms may be substituted or unsubstituted (i.e., N or NR, wherein R is H or other substituents as defined herein). The heterocycle may be attached to a pendant group of any heteroatom or carbon atom to form a stable structure. If the resultant compound is stable, the heterocycle as described herein may be substituted at the carbon- or nitrogen-position. Nitrogen atoms in the heterocycle are optionally quaternized. One preferred embodiment is that when the total number of S and O atoms in the heterocycle exceeds one, these heteroatoms are not adjacent to each other. Another preferred embodiment is that the total number of S and O atoms in the heterocycle does not exceed 1. As used herein, the term "aromatic heterocyclyl" or "heteroaryl" is intended to mean stable 5-, 6-, 7-membered monocyclic or bicyclic, or 7-, 8-, 9- or 10-membered bicyclic heterocyclyl aromatic ring that comprise carbon atoms and 1, 2, 3 or 4 ring heteroatoms independently selected from the group consisting of N, O and S. Nitrogen atoms may be substituted or unsubstituted (i.e., N or NR, wherein R is H or other substituents as defined herein). Nitrogen and sulfur heteroatoms may be optionally oxidized (i.e., NO and S(O)$_p$, wherein p is 1 or 2). It is worth to note that the total number of S and O atoms in the aromatic heretocycle does not exceed 1. Bridge ring is also encompassed within the definition of heterocycle. When one or more atoms (i.e., C, O, N or S) are linked to two non-adjacent carbon atoms or nitrogen atoms, a bridge ring is formed. Preferred bridge ring comprises, but not limited to: one carbon atom, two carbon atoms, one nitrogen atom, two nitrogen atoms, and one carbon-nitrogen bond. It is worth to note that one bridge always converts a monocycle to a tricycle. In a bridge ring, substituent(s) of the ring may also present in the bridge.

Examples of heterocyclic compounds include, but not limited to: acridinyl, azocinyl, benzimidazolyl, benzofuryl, benzothiofuryl, benzothiophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl decahydroquinolinyl, 2H, 6H-1,5,2-dithiazinyl, dihydrofuro[2,3-b]tetrahydrofuryl, furyl, furazanyl, imidazolidinyl, iniidazolinyl imidazolyl, 1H-indazolyl, indolenyl, indolinyl, indolizinyl, indolyl, 3H-indolyl, isobenzofuryl, isoindolyl, isoindolinyl, isoquinolinyl, isothiazoyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazoyl, oxazolidinyl, oxazolyl, hydroxyindolyl, pyrimidyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, thianthrenyl, thiazolyl, isothiazolyl, thienyl, thienooxazolyl, thienothiazolyl, thienoimidazolyl, thienyl, triazinyl, 1,2,4-triazolyl, 1,2,5-triazolyl, 1,3,4-triazolyl, and xanthenyl. Fused ring and Spiro ring compounds are also included.

Unless specified otherwise, the term "hydrocarbyl" or its specific concepts (such as alkyl, alkenyl, alkynyl, aryl, etc.) alone or as a portion of another substituent represent linear, branched, or cyclic hydrocarbon atomic groups or the combination thereof, which may be completely saturated (such as, alkyl), mono- or poly-unsaturated (such as, alkenyl, alkynyl, aryl); mono- or poly-substituted; monovalent (such as, methyl), divalent (such as, methylene) or polyvalent (such as, methine); and may comprise divalent or polyvalent atomic groups, and have a specified number of carbon atoms (such as, $C_1$-$C_{12}$ represents 1-12 carbon atoms, $C_{1\text{-}12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3\text{-}12}$ is selected from the group consisting of $C_3$, $C_4$, $C_6$, $C_7$, $C_8$, $C_9$, $C_{10}$, $C_{11}$ and $C_{12}$). "Hydrocarbyl" comprises, but not limited to, aliphatic hydrocarbyl and aromactic hydrocarbyl, wherein the aliphatic hydrocarbyl may be linear or cyclic, and particularly comprises, but not limited to alkyl, alkenyl, alkynyl, and the aromatic hydrocarbyl comprises, but not limited to 6-12 membered aromatic hydrocarbyls, such as, phenyl, naphthyl, and the like. In some embodiments, the term "hydrocarbyl" represents linear or branched atomic groups or the combination thereof that may be completely saturated, mono- or poly-unsaturated, and may comprise divalent and polyvalent atomic groups. Examples of saturated hydrocarbon atomic groups comprise, but not limited to methyl, ethyl, n-propyl, iso-propyl, n-butyl, tert-butyl, iso-butyl, sec-butyl, iso-butyl, cyclohexyl, (cyclohexyl) methyl, cyclopropylmethyl, as well as homologs or isomers of atomic groups such as n-pentyl, n-hexyl, n-heptyl, n-octyl, and the like. Unsaturated hydrocarbyls may have one or more double bonds or triple bonds, and the examples thereof comprise, but not limited to ethenyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butyryl, and higher homologs and isomers.

Unless specified otherwise, the term "hetero-hydrocarbyl" or its specific concepts (such as heteroalkyl, heteroalkenyl, heteroalkynyl, heteroaryl, etc.) alone or in combination with another term represents a stable linear, branched or cyclic hydrocarbon atomic group or a combination thereof, which consists of a certain number of carbon atoms and at least one heteroatom. In some embodiments, the term "heteroalkyl" alone or in combination with another term represents a stable linear, branched hydrocarbon atomic group or a combination thereof, which consists of a certain number of carbon atoms and at least one heteroatom. In a typical embodiment, the heteroatom is selected from the group consisting of B, O, N and S, wherein the nitrogen and sulfur atoms are optionally oxidized, and the nitrogen heteroatom is optionally quaternized. The heteroatom or heteroatomic group may be located at any internal position of heterohydrocarbyl, including the position where the hetero-hydrocarbyl is attached to the rest part of the molecule, while the terms "alkoxy", "alkylamino" and "alkylthio" (or thioalkoxy) belong to routine expressions, and refer to those alkyls attached to the rest part of the molecule via an oxygen atom, an amino, or a sulfur atom, respectively. Examples comprise, but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —$CH_2$—CH=N—O$CH_3$ and —CH=CH—N($CH_3$)—$CH_3$. At most two heteroatoms may be consecutive, e.g., —$CH_2$—NH—O$CH_3$.

Unless specified otherwise, the term "cyclic hydrocarbyl", "heterocyclic hydrocarbyl" or their specific concepts (such as aryl, heteroaryl, cycloalkyl, heterocycloalkyl, cycloalkenyl, heretocycloalkenyl, cycloalkynyl, heretocycloalkynyl, etc.) alone or in combination with other terms represent cyclized "hydrocarbyl", "hetero-hydrocarbyl", respectively. Moreover, as for hetero-hydrocarbyl or heterocyclic hydrocarbyl (such as heteroalkyl, heterocycloalkyl), heteroatom(s) may be located at the position where the heterocycle is attached to the rest part of the molecule. Examples of cyclic hydrocarbyl comprise, but not limited to cyclopentyl, cyclohexyl, 1-cyclopentenyl, 3-cyclohexenyl, cycloheptyl, and the like. Non-limiting examples of heterocyclyl comprise 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuranoindol-3-yl, tetrahydrothien-2-yl, tetrahydrothien-3-yl, 1-piperzainyl and 2-piperzainyl.

Unless specified otherwise, the term "alkyl" is used to represent a linear or branched saturated hydrocarbyl, which may be mono-substituted (e.g., —$CH_2F$) or poly-substituted (e.g., —$CF_3$), and which may be monovalent (e.g., methyl), divalent (e.g., methylene) or polyvalent (e.g., methine). Examples of alkyl comprise methyl (Me), ethyl (Et), propyl (e.g., n-propyl and iso-propyl), butyl (e.g., n-butyl, iso-butyl, s-butyl, t-butyl), pentyl (e.g., n-pentyl, iso-pentyl, neo-pentyl) or the like.

Unless specified otherwise, "alkenyl" refers to an alkyl having one or more carbon-carbon double bonds at any site of the chain, which may be mono-substituted or poly-substituted, and which may be monovalent, divalent or polyvalent. Examples of alkenyl comprise ethenyl, propenyl, butenyl, pentenyl, hexenyl, m-butadienyl, m-pentadienyl, m-hexadienyl, and the like.

Unless specified otherwise, cycloalkyl comprises any stable cyclic or polycyclic hydrocarbyl, in which any carbon atoms are saturated, which may be mono-substituted or poly-substituted, and which may be monovalent, divalent or polyvalent. Examples of these cycloalkyls comprise, but not limited to, cyclopropyl, norbornanyl, [2.2.2]bicyclooctane, [4.4.0]bicyclodecane, and the like.

Unless specified otherwise, the term "halo" or "halogen", alone or as a part of another substituent, represents an atom of fluorine, chlorine, bromine or iodine. Moreover, the term "halogenated alkyl" is intended to comprise monohalogenated alkyl and polyhalogenated alkyl. For example, the term "halogenated ($C_1$-$C_4$) alkyl" is intended to comprise, but not limited to trifluoromethyl, 2,2,2-trifluoroethyl, 4-chlorobutyl and 3-bromopropyl, and the like. Unless specified otherwise, examples of halogenated alkyl comprise, but not limited to: trifluoromethyl, trichloromethyl, pentafluoroethyl, and pentachloroethyl.

"Alkoxy" represents the above alkyl attached via an oxygen bridge, which has a certain number of carbon atoms. Unless specified otherwise, $C_{1\text{-}6}$ alkoxy comprises $C_1$, $C_2$, $C_3$, $C_4$, $C_5$ and $C_6$ alkoxy. Examples of alkoxy comprise, but not limited to: methoxy, ethoxy, n-propoxy, iso-propoxy, n-butoxy, sec-butoxy, term-butoxy, n-pentoxy and S-pentoxy. Unless specified otherwise, the term "aryl" refers to the poly-unsaturated aromatic hydrocarbon substituent, which may be mono-substituted or poly-substituted, which may be mono-, di-, or poly-valent, and which may mono-cyclic or poly-cyclic (for example, 1-3 rings; of which at least one ring is aromatic) and which are fused together or covalently linked. The term "heteroaryl" refers to aryl. (or ring) containing 1-4 heteroatoms. In an exemplary example, the heteroatom is selected from the group consisting of B, N, O and S, wherein the nitrogen and sulfur atoms are optionally oxidized, and the nitrogen atom is optionally quaternized. Heteroaryl may be attached to the rest part of a molecule through a heteroatom. Non-limiting examples of aryl or heteroaryl comprise phenyl, 1-naphthyl, 2-naphthyl, 4-biphenyl, 1-pyrrolyl, 2-pyrrolyl, 3-pyrrolyl, 3-pyrazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinonyl, 5-isoquinonyl, 2-quinoxalinyl, 5-quinoxalinyl, 3-quinolyl, and 6-quinolyl. The substituent in any one of the above aryl and heteroaryl cyclic systems is selected from the acceptable substituents as described below.

Unless specified otherwise, aryl, when in combination with other terms (e.g., aryloxy, arylthio, aralkyl), comprises the aryl and heteroaryl ring as defined above. Thus, the term "aralkyl" is intended to comprise those radicals having aryl attached to alkyl (e.g., benzyl, phenylethyl, pyridylmethyl, etc.), including those alkyls in which carbon atom(s) (e.g., methylene) have been replaced with oxygen atoms, e.g., phenoxymethyl, 2-pyridyloxymethyl 3-(1-naphthyloxy) propyl and the like.

The compounds of the present invention may be prepared by a variety of synthetic methods well known to persons skilled in the art, including the detailed description as listed below, the embodiments thereof formed by combining with other chemical synthetic methods, as well as equivalence(s) well known to persons skilled in the art. Preferred embodiments comprise, but not limited to the embodiments of the present invention.

The solvents as used in the present invention may be commercially available. The following abbreviations are employed in the present invention: aq represents aqueous; HATU represents O-(7-azabenzotriazol-1-yl)-N,N,N',N'-tetramethylurea hexafluorophosphate; EDC represents N-(3-dimethylamino propyl)-N-ethylcarbodiimide hydrochloride; m-CPBA represents 3-chloroperoxybenzoic acid; eq represents equivalent; CDI represents carbonyl diimidazole; DCM represents dichloromethane; PE represents petroleum ether; DIAD represents di-iso-propyl azodicarboxylate; DMF represents N,N-dimethyl formamide; DMSO represents dimethyl sulfoxide; EtOAc represents ethyl acetate; EtOH represents ethanol; MeOH represents methanol; CBz represents benzyloxy carbonyl, which is an amine protective group; BOC represents tert-butyloxy carbonyl, which is an amine protective group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents di-iso-propyl ethyl amine; SOCl$_2$ represents sulfoxide chloride; CS$_2$ represents carbon disulfide; TsOH represents p-toluene sulfonic acid; NFSI represents N-fluoro-N-(benzene sulfonyl)benzene sulfonamide; NCS represents 1-chloropyrrolidin-2,5-dione; n-Bu$_4$NF represents tetrabutyl ammonium fluoride; iPrOH represents 2-propanol; Trip represents melting point; WA represents lithium di-iso-propylamide; EGTA represents ethylene glycol bis(2-amino ethyl ether) tetraacetic acid; ATP represents adenosine triphosphate; HEPES represents 4-hydroxyethyl piperazine ethanesulfonic acid; MgCl$_2$ represents magnesium chloride; MnCl$_2$ represents manganese chloride; EGTA represents ethylene glycol bis(2-amino ethyl ether) tetraacetic acid; DTT represents dithiothreitol; DIEA represents N,N-diisopropyl ethyl amine; NaBH4 represents sodium borohydride; NBS represents N-bromosuccinimide; XPhos represents 2-di-tert-butylphosphino-2',4',6'-triisopropyl biphenyl.

The compounds are named manually or by ChemDraw® software, and the commercially available compounds are named based on the supplier's catalog.

DETAILED DESCRIPTION OF EMBODIMENT

The present invention will be described in detail through the following embodiments, but it is not meant to limit the invention in any undesirable way. The present invention has been described in detail herein, in which the particular embodiments thereof also have been disclosed. It will be apparent to those skilled in the art of various modifications and improvements on the detailed description of the present invention without deviating from the spirit and scope of the present invention.

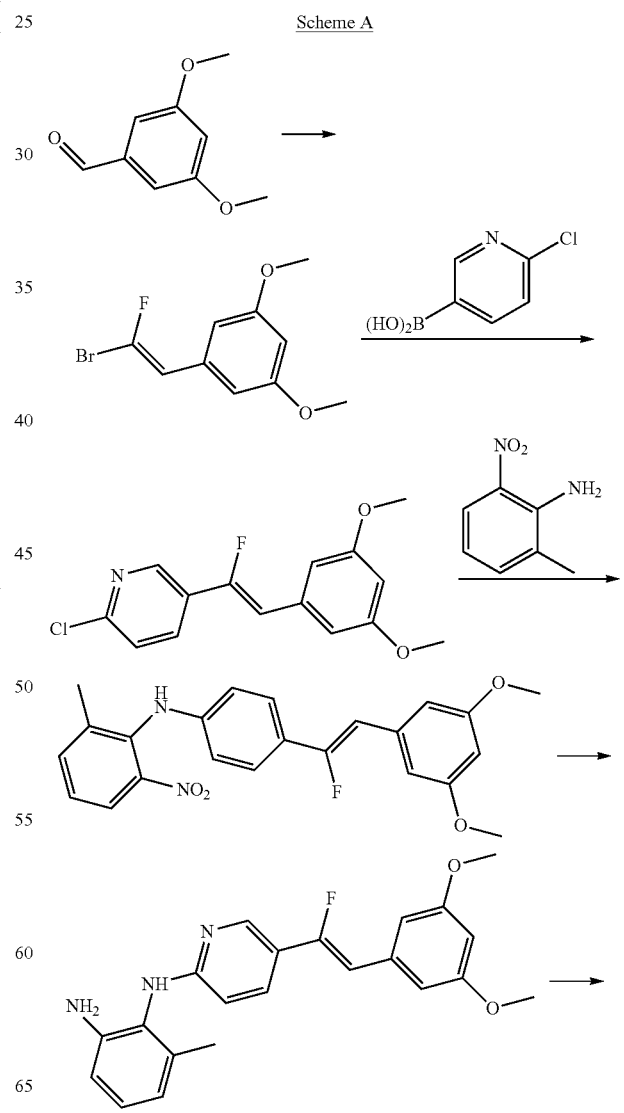

Scheme A

Control Example 1

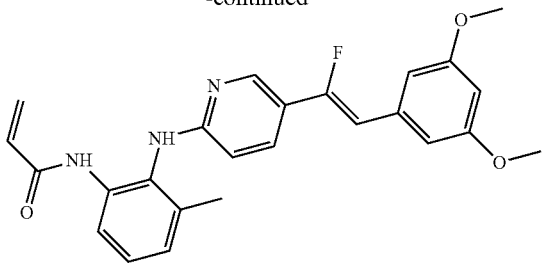

Control Example 1A

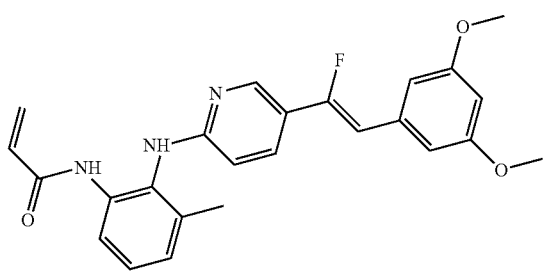 [SMILES: C=CC(=O)Nc1cccc(C)c1Nc1ccc(/C(F)=C/c2cc(OC)cc(OC)c2)cn1]

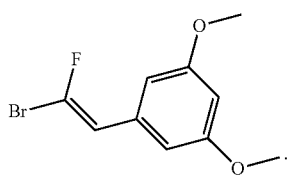

At room temperature (28° C.), hydrazine hydrate (18.1 g, 361 mmol) was dropwise added into 3,5-dimethoxy benzaldehyde (20 g, 120 mmol). At room temperature, after stirring for 2 hours, TLC detection showed that 3,5-dimethoxy benzaldehyde has not reacted completely, thus prolonging the reaction time. After continuously reacting for 16 hours, to the reaction flask were added ethylenediamine (21.70 g, 361 mmol) and cuprous chloride (1.19 g, 12.04 mmol). After stirring for 30 minutes, the reaction solution was placed in an ice-bath and cooled to 0° C., then a solution of tribromofluoromethane (81.46 g, 301 mmol) in ethanol (30 ml) was dropwise added into the reaction solution through a constant pressure dropping funnel (with a little gas being released during the dropwise addition). Upon the completion of the dropwise addition, the reaction was stirred at 0° C. for 1 hour, then warmed slowly to room temperature (28° C.), and then reacted continuously for 1 hour. After the intermediate E-3,5-dimethoxy phenylhydrazone was completely reacted, it was filtered, the solid was washed with ethyl acetate, the filtrate was concentrated at reduced pressure to evaporate off most of the solvents. It was diluted with ethyl acetate (200 ml), and washed with an aqueous solution of citric acid (1M, 50 ml), the liquid was separated, and the aqueous phase was then extracted with ethyl acetate (3×100 ml). The organic phase was combined and washed with saturated saline (150 ml), dried over anhydrous sodium sulfate, and filtered. The filtrate was concentrated at reduced pressure to give a crude product, which was separated over a flash silica gel column (mobile phase: 0~15% ethyl acetate/petroleum ether) to give the control example 1A (18.86 g, yield: 60%) as a light yellow liquid.

$^1$H NMR (400 MHz, CHLOROFORM-d) δ 6.56 (d, J=2.4 Hz, 2H), 6.43-6.39 (m, 1H), 5.92 (d, J=32.4 Hz, 1H), 3.80 (s, 6H).

Control Example 1B

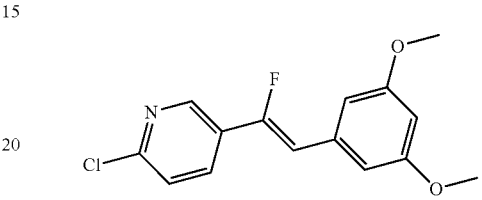

The control example 1B was synthesized by employing the same process as described in embodiment 1C, the analytical data was shown below;

LCMS (ESI) m/z: 294.1[M+1]$^+$

Control Example 1C

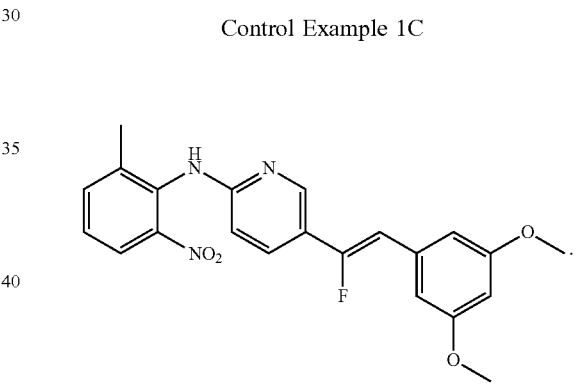

To a solution of the control example 1B (190 mg, 647 μmol) and 2-methyl-3-nitroaniline (148 mg, 971 μmol) in N,N-methyl acetamide were added tri(dibenzylidene acetone)dipalladium (59 mg, 64.69 μmol), 2-dicyclohexyl phosphine-2,4,6-triisopropyl biphenyl (62 mg, 129 μmol), cesium carbonate (421 mg, 1.29 mmol), the mixture was stirred at 110° C. for 2 hours under the protection of nitrogen. To the mixture was added ethyl acetate (20 ml), washed with water (250 ml), extracted with ethyl acetate for 3 times. The organic phase was dried over anhydrous sodium sulfate, filtered, the solution was rotatory evaporated until dry, the sample was mixed and passed through the column to give the dark-red control example 1C (197 mg).

LCMS (ESI) m/z: 410.1 [M+1]$^+$ $^1$H NMR. (400 MHz, CHLOROFORM-d) δ (ppm) 8.46 (d, J=2.0 Hz, 1H), 8.08 (br. s., 1H), 7.93 (d, J=8.0 Hz, 1H), 7.74 (dd, J=2.4, 8.4 Hz, 1H), 7.54 (d, J=7.6 Hz, 1H), 7.26 (s, 1H), 6.78 (d, J=2.0 Hz, 2H), 6.57 (d, J=9.2 Hz, 1H), 6.41 (t, J=2.0 Hz, 1H), 6.01-6.17 (m 1H), 3.82 (s, 6H), 2.26 (s, 3H).

Control Example 1D

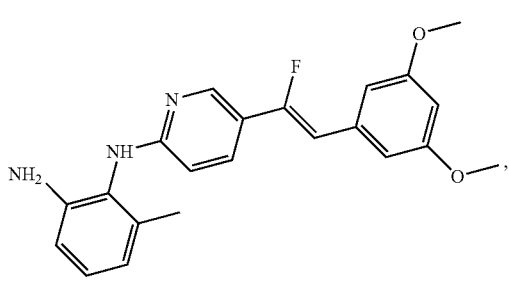 [SMILES: COc1cc(/C=C(\F)c2ccc(Nc3c(C)cccc3N)nc2)cc(OC)c1]

To a 90% solution of the control example 1C (197 mg, 481 μmol) in ethanol (6.0 ml) were added ferrous powder (134 mg, 2.41 mmol), ammonium chloride (129 mg, 2.41 mmol). The mixture was stirred at 100° C. for 2 hours. The mixture was diluted with ethyl acetate (10 ml), washed with water, extracted with ethyl acetate for 3 times, dried over anhydrous sodium sulfate, the solvent was removed by rotatory evaporation until dry to give the control example 1D (189 mg, crude).

LCMS (ESI) 380.1 [M+1]$^+$

Control Example 1

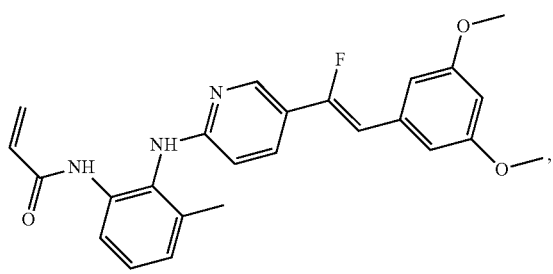 [SMILES: C=CC(=O)Nc1cccc(C)c1Nc1ccc(/C(F)=C/c2cc(OC)cc(OC)c2)cn1]

At 0° C., to a solution of the crude control example 1D (152 mg, 401 μmol) in dichloromethane (7.0 ml) were added N,N-diisopropyl ethyl amine (104 mg, 801 μmol) and a solution of acryloyl chloride (29 mg, 320 μmol) in dichloromethane (1.0 ml) successively, and stirred for half an hour. The mixture was quenched with water (5.0 ml), washed with water, extracted with dichloromethane for 3 times, and post-treated to give the final compound control example 1 (20 mg).

LCMS (ESI) m/z: 434.3 [M+1]

$^1$H NMR (400 MHz, CHLOROFORM-d) δ 11.27 (br. s., 1H), 8.25 (br. s., 1H), 8.15 (s, 1H), 8.02 (d, J=8.0 Hz, 1H), 7.91 (d, J=9.2 Hz, 1H), 7.34 (dd, J=8.0, 8.0 Hz, 1H), 7.13 (d, J=7.6 Hz, 1H), 6.75 (d, J=1.6 Hz, 2H), 6.50 (d, J=9.6 Hz, 1H), 6.45 (s, 1H), 6.35-6.42 (m, 1H), 6.22-6.31 (m, 1H), 6.12 (d, J=38.4 Hz, 1H), 5.74 (d, J=10.4 Hz, 1H), 3.83 (s, 6H)

Scheme B

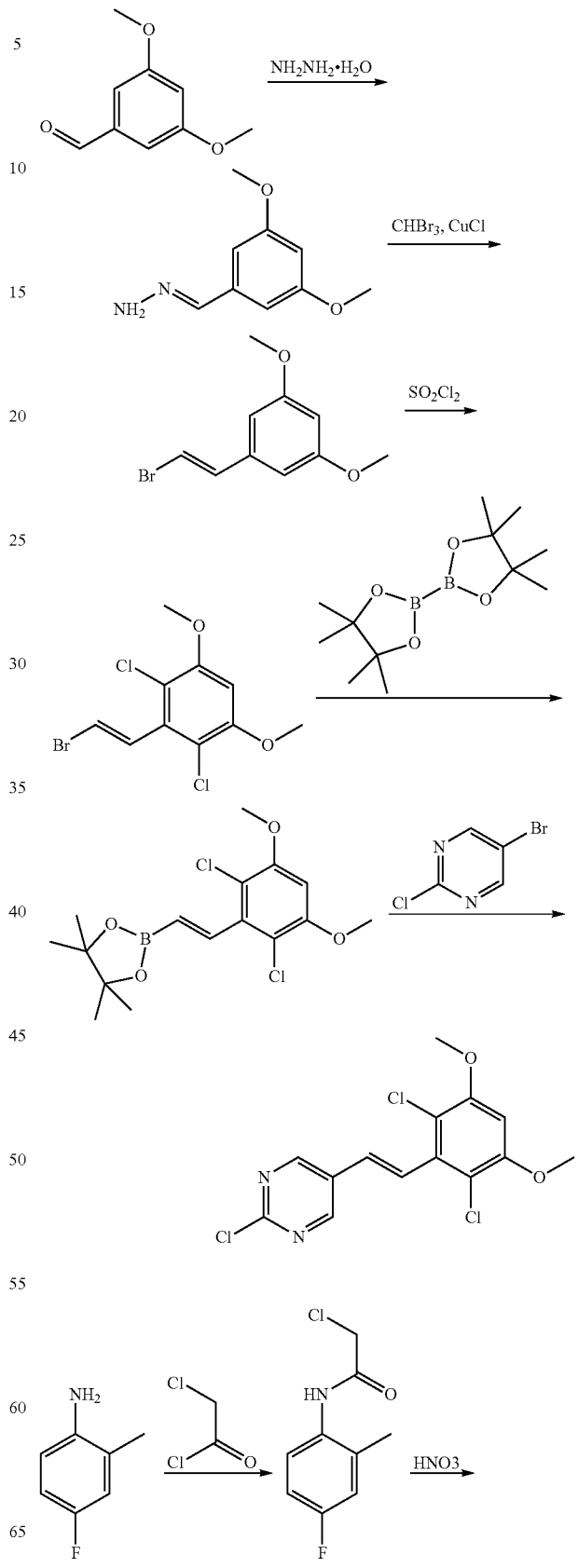

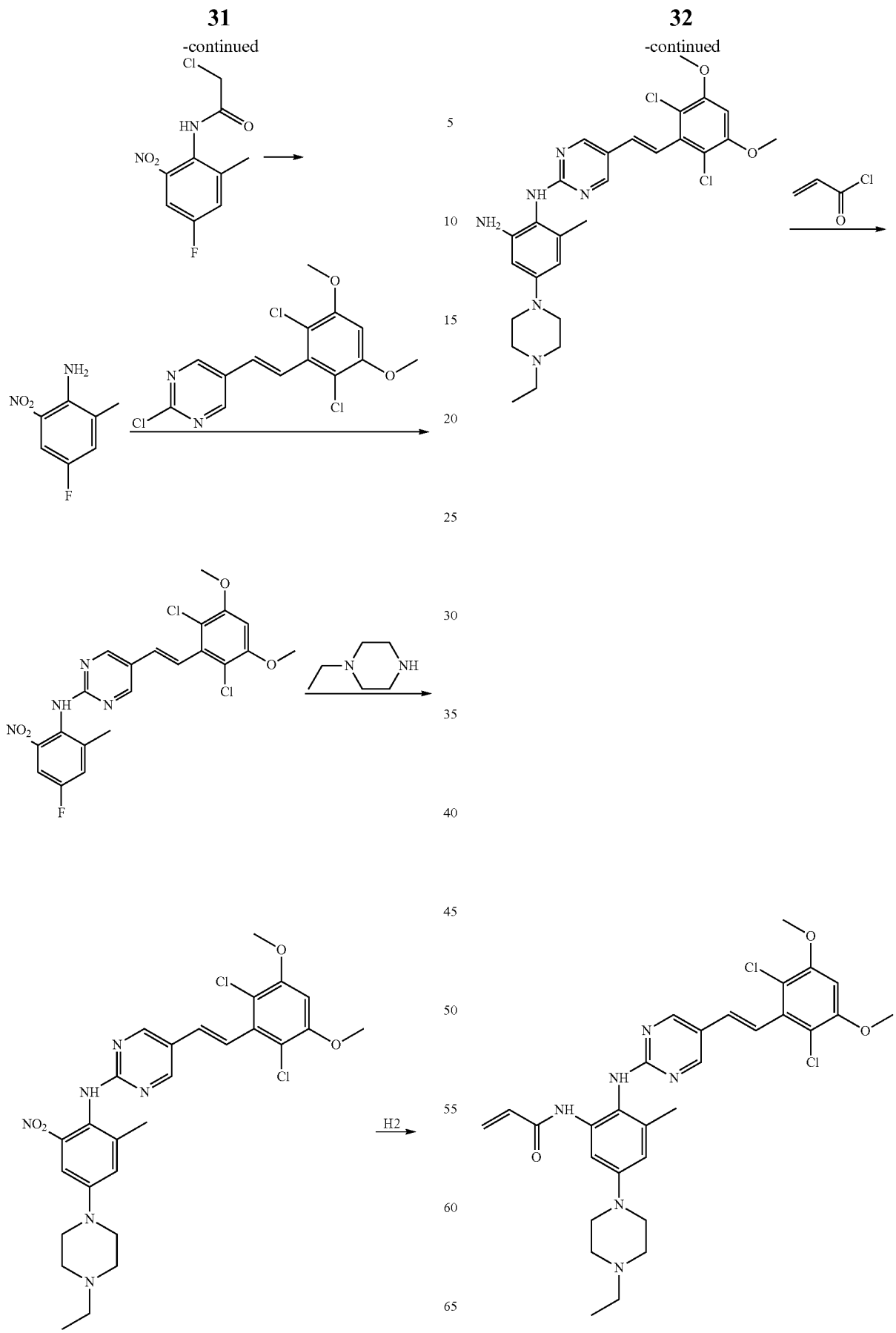

Control Example 2

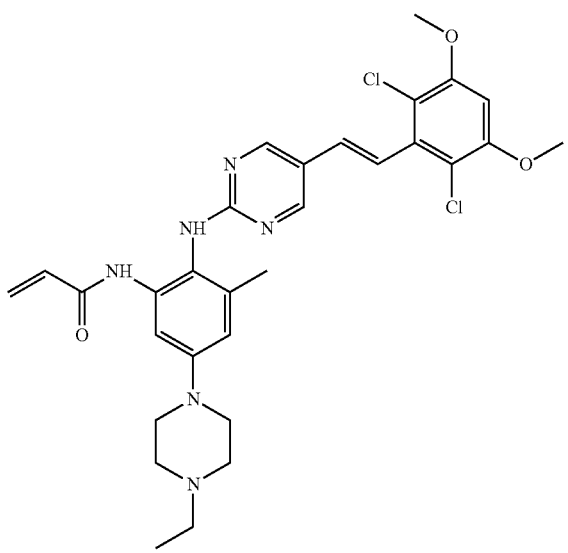 [SMILES: C=CC(=O)Nc1cc(N2CCN(CC)CC2)cc(C)c1Nc1ncc(/C=C/c2c(Cl)c(OC)cc(OC)c2Cl)cn1]

Control Example 2A

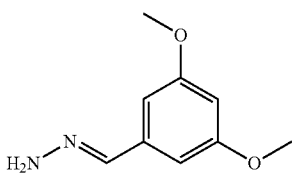

Hydrazine hydrate (27.11 g, 541.62 mmol) was added into a solution of 3,5-dimethoxy benzaldehyde (30.00 g, 180.54 mmol) in ethanol (300.00 ml), stirred at 80-90° C. for 2 hours. When thin layer chromatography showed that the reaction has been completed, the solvent was removed by concentration at reduced pressure to give the control example 2A (33.10 g) as a colorless oil.

$^1$H NMR (400 MHz, CHLOROFORM-d) δ 3.80 (s, 6H) 5.54 (br. s., 2H) 6.42 (t, J=2.26 Hz, 1H) 6.71 (d, J=2.01 Hz, 2H) 7.66 (s, 1H).

Control Example 213

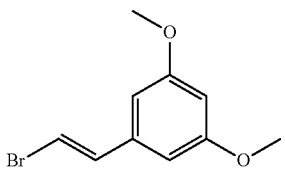

Ammonia water (54.67 g, 389.97 mmol) and cuprous chloride (1.79 g, 18.05 mmol) were added into a solution of control example 2A (32.53 g, 180.54 mmol) in dimethylsulfoxide (300.00 ml). With stirring at room temperature, chloroform (136.88 g, 541.62 mmol) was dropwise added slowly (an obvious exothermic reaction) into the reaction solution. Upon completion, the reaction was placed in an oil bath at 30-40° C. and stirred for 26 hours. Upon completion, the reaction was cooled to room temperature, into which were added 1200 ml water, 500 ml ethyl acetate, and the mixture was mixed evenly to be partitioned. The aqueous phase was extracted with 1200 ml (600 ml*2) ethyl acetate. The organic phase was dried over anhydrous sodium sulfate, filtered, and concentrated at reduced pressure to give a crude product, which was purified over a flash silica gel column (petroleum ether:ethyl acetate=20:1) to give a light yellow control example 2B (14.13 g, 58.12 mmol, 32.19% yield).

$^1$H NMR (400 MHz, CHLOROFORM-d) δ 6.99-7.06 (m, 1H) 6.86 (d, J=2.01 Hz, 2H) 6.39-6.50 (m, 2H) 3.81 (s, 6H).

Control Example 2C

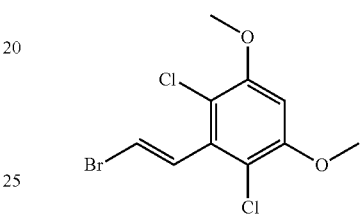

At −60 to −50° C., sulfonyl chloride (19.61 g, 145.20 mmol) was dropwise added into a solution of the control example 2B (14.12 g, 58.08 mmol) in tetrahydrofuran (140.00 ml) slowly, and the mixture was stirred for 5 minutes, with the thin layer chromatography showing that the reaction has been completed. To the reaction solution was added 200 ml water to quench the reaction, into which was additionally added 100 ml ethyl acetate, the mixture was mixed evenly and then partitioned. The water phase was extracted with 150 ml ethyl acetate for 2 times. The organic phase was dried over anhydrous sodium sulfate and then filtered, concentrated at reduced pressure to give the control example 2C (19.53 g crude) as a light yellow solid.

$^1$HNMR (400 MHz, CHLOROFORM-d) δ 3.87-3.93 (m, 6H) 6.49-6.55 (m, 1H) 6.85-6.93 (m, 1H) 7.10-7.19 (m, 1H).

Control Example 2D

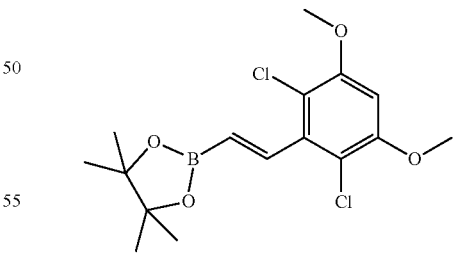

The control example 2C (19.53 g, 62.60 mmol), bis (pinacolato)diboron (16.06 g, 63.23 mmol), Pd(dppf)Cl$_2$ (4.58 g, 6.26 mmol) and potassium acetate (19.29 g, 125.20 mmol) were dissolved in a solution of dioxane (200 ml). After replacement with nitrogen for three times, the reaction solution was stirred at 80-90° C. for 18 hours. Upon completion of the reaction, the reaction solution was cooled to room temperature and then filtered. It was concentrated at reduced pressure to give a crude product, which was purified over a flash silica gel column (petroleum ether:ethyl acetate=10:1) to give the control example 2D (13.15 g, 36.62 mmol, 58.51% yield) as a white solid.

¹HNMR (400 MHz, CHLOROFORM-d) δ 7.31-7.39 (m, 1H) 6.51 (s, 1H) 6.15 (d, J=18.82 Hz, 1H) 3.92 (s, 6H) 1.32 (s, 12H).

Control Example 2E

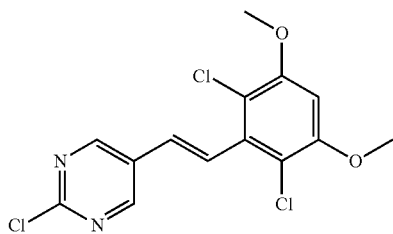 [SMILES: COc1cc(OC)c(Cl)c(/C=C/c2cnc(Cl)nc2)c1Cl]

To the mixture of 2-chloro-5-bromopyrimidine (10 g, 51.70 mmol), the control example 2D (20.42 g, 56.87 mmol), Pd(dppl)Cl₂ (3.78 g, 5.17 mmol), K3PO4 (21.95 g, 103.40 mmol) were added dioxane (100.00 MO, water (20.00 mL). The reaction solution was stirred at 100° C. for 21 hours. When TLC showed that the reaction has been completed, to the reaction solution was added water (100 ml), the mixture was extracted with ethyl acetate (100 ml×3) for 3 times. The organic phase was combined, dried over anhydrous sodium sulfate, filtered and rotatory evaporated until dry, the residue of which was purified over a flash silica gel column to give the control example 2E (7.56 g, 17.50 mmol, 33.85% yield, 80% purity) as a yellow solid.

Control Example 2F

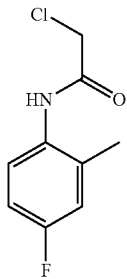

At 10° C., a solution of chloroacetyl chloride (18.23 g, 161.42 mmol) in ethyl acetate (30.00 mL) was dropwise added into a suspension of 4-fluoro-2-methyl aniline (20.00 g, 159.82 mmol) in ethyl acetate (160.00 mL) and sodium carbonate (16.94 g, 159.82 mmol), after the completion of the dropwise addition, the suspension was stirred at this temperature for 30 minutes; upon the completion, to the reaction was added water, extracted with ethyl acetate (30 ml×3). The organic layer was combined and washed with water (20 ml×2) and saturated saline (30 ml) successively, dried over anhydrous sodium sulfate, filtered, and concentrated in vacuum to give the control example 2F which was directly used in the next step without being purified.

¹HNMR (400 MHz, CHLOROFORM-d) δ 8.14 (br. s., 1H), 7.74 (dd, J=5.5, 9.5 Hz, 1H), 7.01-6.89 (m, 2H), 4.32-4.20 (m, 2H), 2.35-2.25 (m, 3H).

Control Example 2G

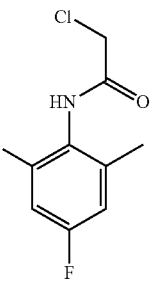

At 0° C., nitric acid (13.39 g, 146.61 mmol) was dropwise added into a solution of the control example 2A (29.56 g, 146.61 mmol) in sulfuric acid (150 ml) slowly, after the completion of the dropwise addition, the mixture was stirred at this temperature for 30 minutes; upon the completion of the reaction, the reaction solution was poured slowly into the stirring ice-water, from which a large amount of light purple solid was precipitated, and filtered, the filter cake was rinsed with water for many times to give a light purple control example 2G (34 g), which was directly used in the next step without being further purified.

¹HNMR (400 MHz, CHLOROFORM-d) δ 8.99 (br. s., 1H), 8.67 (d, J=7.0 Hz, 1H), 8.29 (br. s., 1H), 7.61 (dd, J=2, 5, 7.0 Hz, 1H), 7.30 (dd, J=2, 5, 8.0 Hz, 1H), 7.17 (d, J=1.1.5 Hz, 1H), 4.76 (hr. s., 1H), 4.27 (s, 2H), 4.22 (s, 1H), 2.40 (s, 3H), 2.35 (s, 2H)

Control Example 2H

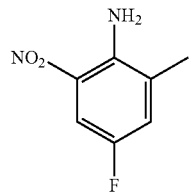

An aqueous solution of sodium hydroxide (4 mol, 229.19 ml) was added into a solution of the control example 2G (34 g, 137.86 mmol) in tetrahydrofuran (5 ml), the reaction solution was heated to 95° C. and stirred for 2 hours; upon the completion of the reaction, the reaction solution was cooled, into which were added ethyl acetate (50 ml) and water (50 ml), the mixture was extracted with ethyl acetate (100 ml×5). The organic layer was combined and washed with water (20 m×2) and saturated saline (10 ml) successively, dried over anhydrous sodium sulfate, filtered, and concentrated in vacuum, the residue of which was purified over a flash silica gel column to give the control example 2H (4.91 g, 28.86 mmol) as a yellow solid.

¹HNMR (400 MHz, DMSO-d6) δ 7.65 (dd, J=2.3, 9.3 Hz, 1H), 7.39 (d, J=8.0 Hz, 1H), 7.25-7.05 (m, 1H), 2.23 (s, 3H).

Control Example 2I

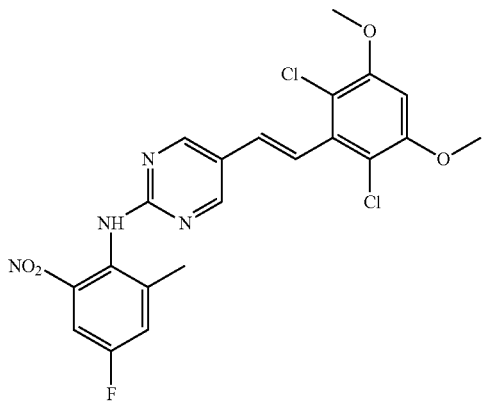 [SMILES: COc1cc(OC)c(Cl)c(/C=C/c2cnc(Nc3c(C)cc(F)cc3[N+](=O)[O-])nc2)c1Cl]

Pd(dba)$_2$ (169.05 mg, 294.00 μmol), XPhos (280.31 mg, 588.00 μmol) and potassium carbonate (1.22 g, 8.82 mmol) were added into a solution of the control example 2H (500.00 mg, 2.94 mmol) and the control example 2E (1.32 g, 3.82 mmol) in tert-butanol (5.00 ml). Under the protection of nitrogen, the suspension was heated to 110° C., and stirred for 4 hours; upon completion, the reaction was cooled, filtered, and the filtrate was concentrated in vacuum, the residue of which was purified over a flash silica gel column to give the product (2.90 g, 6.05 mmol) as a light yellow solid.

$^1$H NMR (400 MHz, CHLOROFORM-d) δ 8.55 (s, 2H), 7.75 (s, 1H), 7.62 (dd, J=2.9, 7.9 Hz, 1H), 7.31 (dd, J=2.8, 8.3 Hz, 1H), 7.09-6.87 (m, 2H), 6.54 (s, 1H), 3.95 (s, 6H), 2.36 (s, 3H).

LCMS (ESI) m/z: 479.0 [M+1]$^+$

Control Example 2J

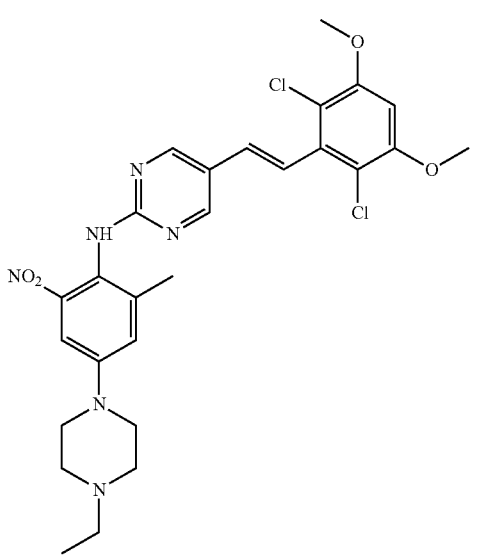

N-methylpiperazine (714.75 mg, 6.26 mmol) was added into a solution of the control example 2I (300 mg, 625.93 μmol) in dimethylsulfoxide (3 ml), the mixture was stirred at 135° C. for 18 hours. Upon completion, the reaction was cooled to room temperature, to the reaction solution were added 30 ml ethyl acetate and 35 ml water, the mixture were mixed evenly and then partitioned. The water phase was extracted with 15 ml ethyl acetate for 2 times, the organic phase was dried over anhydrous sodium sulfate, filtered and concentrated at reduced pressure to give a crude product, which was purified over a flash silica gel column (dichloromethane:methanol=15:1-10:1), and purified again over a thin layer chromatography preparative plate (dichloromethane:methanol=10:1) to give the title control example 2J (20 mg, 34.88 mmol, 5.57% yield) as a yellow solid.

LCMS (ESI) m/z: 573.3 [M+1]$^+$

Control Example 2K

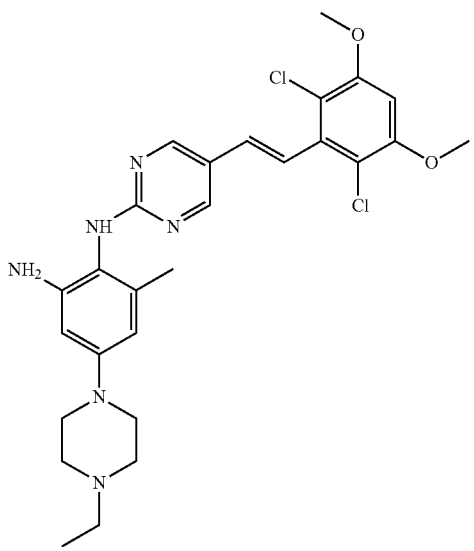 [SMILES: CCN1CCN(c2cc(C)c(Nc3ncc(/C=C/c4c(Cl)c(OC)cc(OC)c4Cl)cn3)c([N+](=O)[O-])c2)CC1]

At 15 Psi hydrogen pressure; Raney-Ni (400 mg, 4.67 mmol) was added into a mixed solution of the control example 2J (20 mg, 34.88 μmol) in ethanol (2 ml) and tetrahydrofuran (2 ml), the reaction solution was stirred at 5-10° C. for 10 minutes. When LCMS showed that the reaction has been completed, the reaction solution was filtered, concentrated at reduced pressure to give the control example 2K (15.00 mg crude) as a yellow solid.

LCMS (ESI) m/z: 543.1 [M+1]$^+$

Control Example 2

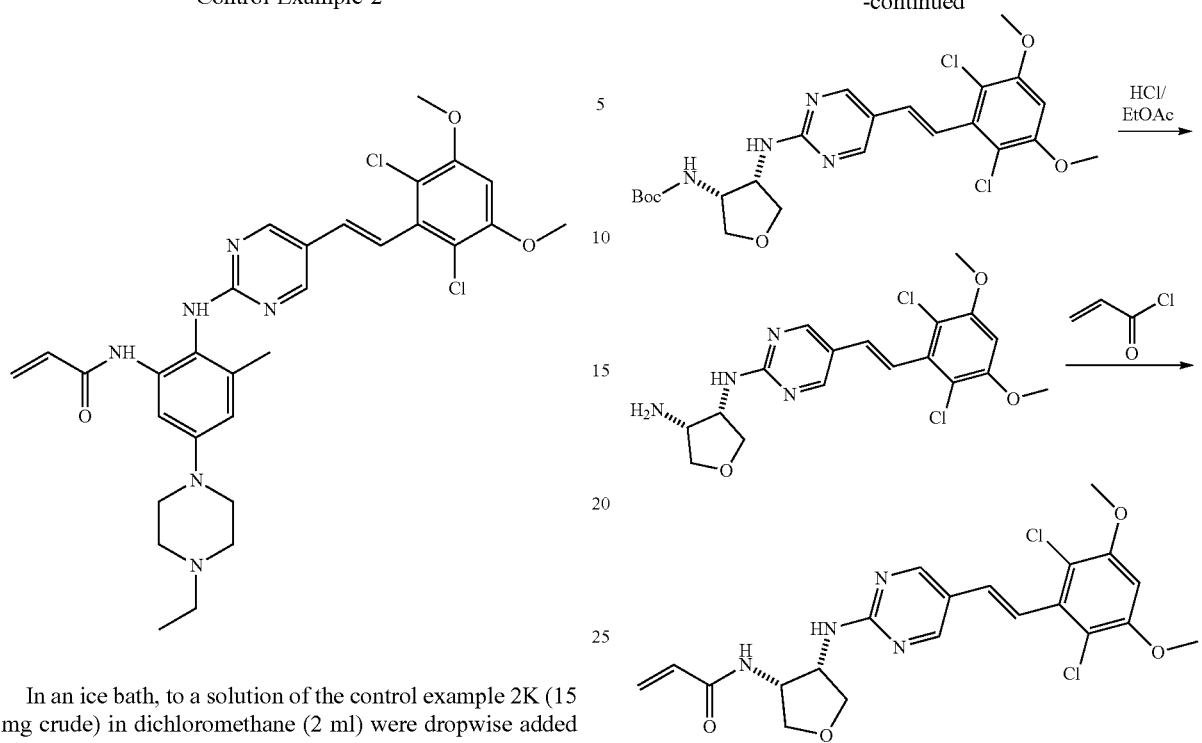

In an ice bath, to a solution of the control example 2K (15 mg crude) in dichloromethane (2 ml) were dropwise added N,N-diisopropyl ethyl amine (7.13 mg, 55.20 μmol) and acryloyl chloride (2.50 mg, 27.60 μmol) successively. The reaction solution was stirred at 0° C. for 15 minutes. When LCMS detected that the reaction has been completed, 10 ml ethyl acetate and 15 ml water were added to the reaction solution. They were mixed evenly and left to be partitioned. The aqueous phase was extracted with 10 nil ethyl acetate for 3 times, and the organic phase was dried over anhydrous sodium sulfate and then filtered, concentrated at reduced pressure to give a crude product, which was separated by high performance liquid chromatography (trifluoroacetic acid-acetonitrile) and lyophilized to give the control example 2 (3.00 mg, 5.02 μmol, 18.19% yield) as a yellow solid.

LCMS (ESI) m/z: 597.1 $[M+1]^+$ $^1$H NMR (400 MHz, METHANOL-d4) δ1.44 (t, J=7.40 Hz, 3H) 2.27 (s, 3H) 3.12-3.31 (m, 6H) 3.68-3.78 (m, 2H) 3.94-4.00 (m, 8H) 5.78 (dd, J=10.04, 1.76 Hz, 1H) 6.30-6.37 (m, 1H) 6.42-6.51 (m, 1H) 6.83 (s, 1H) 6.93-7.02 (m, 2H) 7.25 (d, J=16.81 Hz, 1H) 7.34-7.42 (m, 1H) 8.65-8.88 (m, 2H).

Scheme C

Scheme C

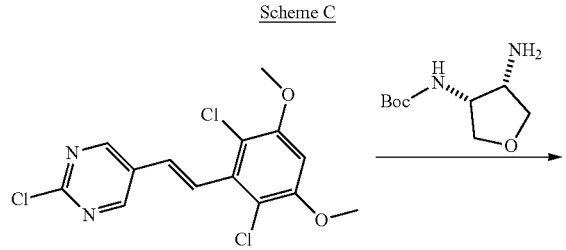

Control Example 3

Control Example 3A

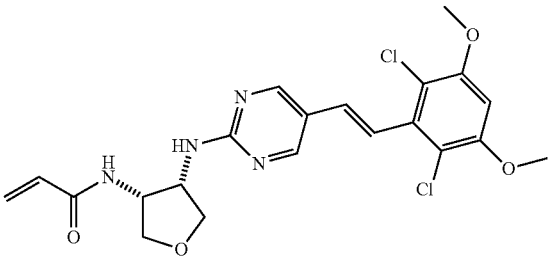 [SMILES: C=CC(=O)N[C@H]1COC[C@H]1Nc1ncc(/C=C/c2c(Cl)c(OC)cc(OC)c2Cl)cn1]

To a solution of the control example 2E (300.00 mg, 868.03 μmol, 1.00 eq.) and Example 20E (300.00 mg, 1.14 mmol, 1.31 eq.) in N-methylpyrrolidone (6 ml) was added sodium bicarbonate (150.22 mg, 1.79 mmol, 2.06 eq.), and the mixture was reacted at 100° C. for 18 hours. When thin layer chromatography-liquid chromatography-mass spectrometer detected that the reaction has been completed, the reaction solution was diluted with 20 ml water, extracted with ethyl acetate (15 ml for each time) for 2 times, and washed with saturated saline (10 ml for each time) for two times. The organic phase was dried over anhydrous sodium sulfate, filtered, and concentrated in vacuum, the residue of which was purified over a flash silica gel column (petroleum ether/ethyl acetate=I/O to 4/1) to give the control example 3A (178.00 mg, yield: 40.10%) as a yellow solid.

LCMS (ESI) m/z: 511.1 [M+1]+

$^1$H NMR (400 MHz, CHLOROFORM-d) δ8.49 (s, 3H), 6.95-7.02 (m, 2H), 6.85-6.92 (m, 2H), 6.52 (s, 2H), 5.61 (br s, 1H), 5.21 (br s, 1H), 4.98 (br s, 1H), 4.75 (quip, J=6.52 Hz, 1H), 4.46 (br s, 1H), 4.18 (dd, J=6.52, 9.02 Hz, 1H), 4.07-4.15 (m, 4H), 3.94 (s, 9H), 3.65-3.73 (m, 2H), 2.04 (s, 4H), 1.39 (s, 8H), Control Example 3B

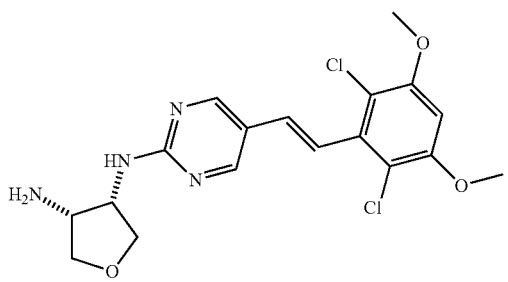 [SMILES: COc1cc(OC)c(Cl)c(/C=C/c2cnc(N[C@@H]3COC[C@@H]3N)nc2)c1Cl]

To the control example 3A (40.00 mg, 78.22 μmol, 1.00 eq.) was added a solution of ethyl acetate hydrochloride (4 mol, 5 ml, 255.69 eq.), and the mixture was reacted at 30° C. for 1 hour. When liquid chromatography-mass spectrometer detected that there were raw materials remained, the reaction solution was reacted continuously at 100° C. for 16 hours. When liquid chromatography-mass spectrometer detected that the reaction has been completed, the reaction was filtered, and concentrated in vacuum to give the control example 3B (30.00 mg) as a yellow solid, which was used directly in the next step.

LCMS (ESI) m/z: 411.0 [M+1]+

Control Example 3

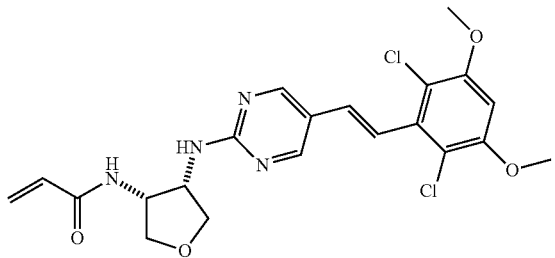 [SMILES: C=CC(=O)N[C@H]1COC[C@H]1Nc1ncc(/C=C/c2c(Cl)c(OC)cc(OC)c2Cl)cn1]

At 0° C., to a solution of the control example 3B (30.00 mg, 72.94 μmol, 1.00 eq.) and N,N-diisopropyl ethyl amine (19.70 mg, 152.45 mmol, 26.63 μl, 2.09 eq.) in dichloromethane (4 ml) was added acryloyl chloride (0.25 mol/l, 150.00 μl, 0.51 eq.), and the mixture was reacted at 0° C. for 0.5 hours. When the liquid chromatography-mass spectrometer showed that there were raw materials remained, the reaction was continued at 0° C. for 1 hour. When liquid chromatography-mass spectrometer detected that the reaction has been completed, the reaction was quenched with water (15 ml), extracted with dichloromethane (10 ml for each time) for 3 times. The organic phase was dried over anhydrous sodium sulfate, filtered, concentrated in vacuum, purified by high performance liquid chromatography (trifluoroacetic acid system:column:Boston Green ODS 150*30 5 u; mobile phase: [water (0.1% trifluoroacetic acid)-acetonitrile]; B %: 36%-46%, 8 min), and lyophilized to give the control example 3 (6.00 mg, yield: 17.68%) as a white solid.

LCMS (ESI) m/z: 465.1 [M+1]+

$^1$H NMR (400 MHz, CHLOROFORM-d) δ 8.51 (br s, 2H), 6.99-7.05 (m, 1H), 6.85-6.92 (m, 1H), 6.54 (s, 1H), 6.41 (br s, 1H), 6.22-6.28 (m, 1H), 6.03-6.11 (m, 1H), 5.64 (d, J=9.03 Hz, 1H), 4.78-4.88 (m, 2H), 4.19 (td, J=6.43, 9.47 Hz, 2H), 3.91-3.96 (m, 6H), 3.74-3.86 (m, 3H).

Scheme X

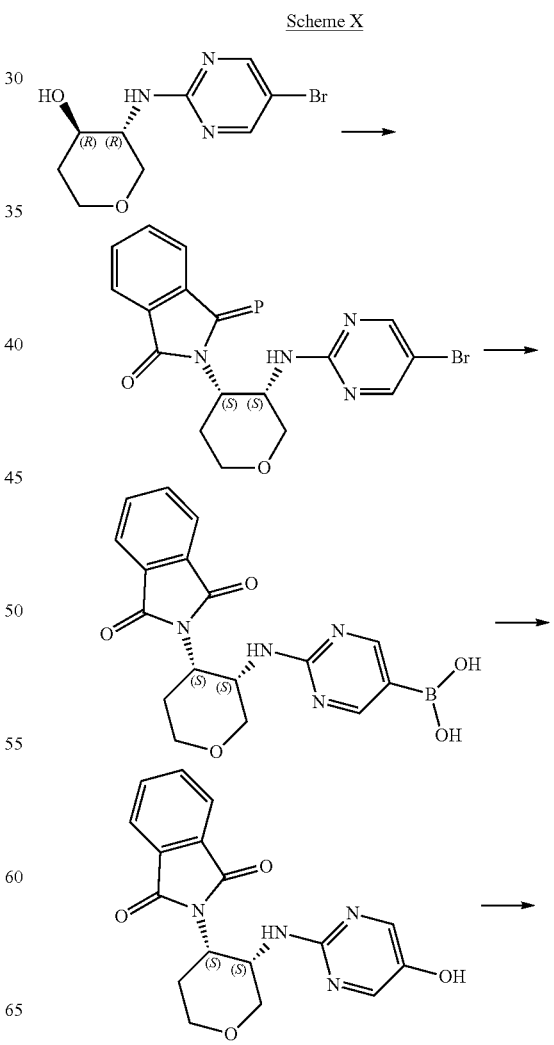

-continued

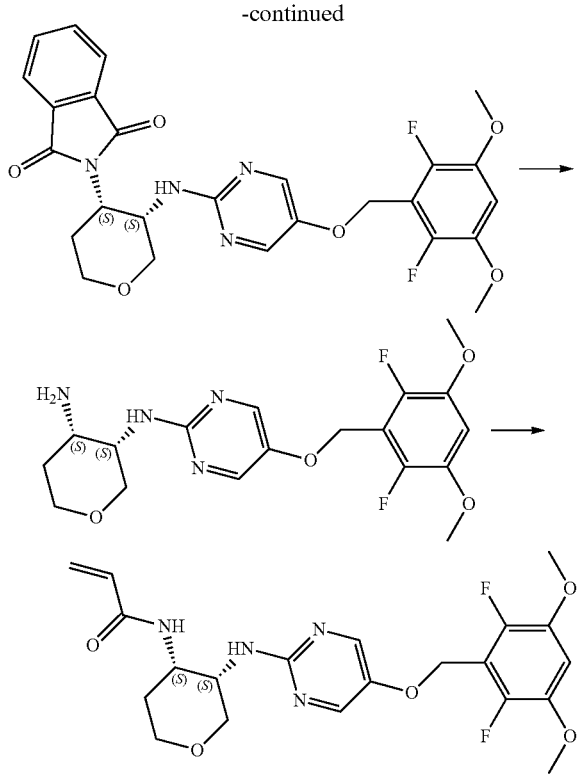

Control Example 4

Control Example 4A

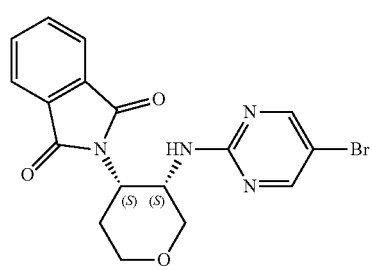

(3R,4R)-3-[(5-bromopyrimidine-2-yl)amine]tetrahydro-2H-pyran-4-ol (600.00 mg, 2.19 mmol) was dissolved in dry tetrahydrofuran (10 mL), into which was added triphenylphosphine (861.19 mg, 3.29 mmol) in one portion, and then was added DIAD (663.93 mg, 3.29 mmol) slowly. The reaction solution was reacted at 20° C. for 3 hours. The reaction solution was concentrated until dry to give a crude product, which was purified over a flash silica gel column (petroleum ether:ethyl acetate=3/1-1/1) to give a crude control example 4A (yellow solid, 1.3 g).

LCMS (ESI) m/z: 402.8, 404.8 [M+1]$^+$

Control Example 4B

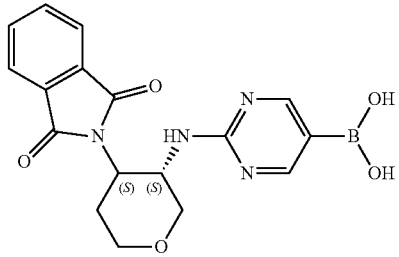

The control example 4A (400 mg, 0.99 mmol) was dissolved in an one-neck flask (50 mL) containing dioxane (3 mL), into which were then added bis(pinacolato)diboron (305 mg, 1.2 mmol), Pd$_2$(dba)$_3$ (90.84 mg, 0.1 mmol), KOAc (196 mg, 2.0 mmol), tricyclohexylphosphine (55.64 mg, 0.2 mmol), with nitrogen replacement for 3 times, then under the protection of nitrogen, the reaction solution was stirred at the temperature of 90° C. for 12 hours. The reaction solution was filtered, and the filtrate was rotatory evaporated until dry at reduced pressure to give the control example 49 crude product (600 mg) which was used directly in the next step.

LCMS (ESI) ink: 369.1 [M+1]$^+$

Control Example 4C

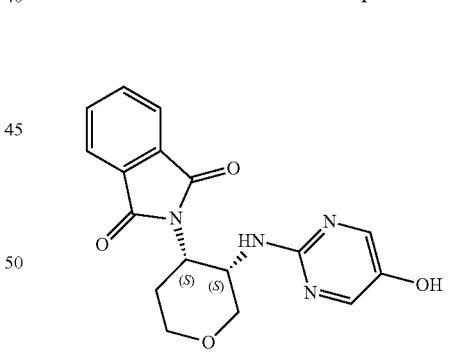

The control example 4B (550 mg, crude) was dissolved in tetrahydrofuran (10 mL), into which was then added hydrogen peroxide (0.22 mL, 30%), and the mixture was stirred at room temperature (15-20° C.) for 2 hours. The reaction was quenched with 10 ml water, extracted with ethyl acetate (20 ml×2). The organic layer was combined, then washed with saturated saline (30 ml), dried over anhydrous sodium sulfate, filtered, and concentrated in vacuum to give the crude product, which was purified over a preparative plate (petroleum ether:ethyl acetate=1/1) to give the control example 4C (white solid, 200 mg, 39% yield).

LCMS (ESI) m/z: 341.1 [M+1]$^+$

Control Example 4D

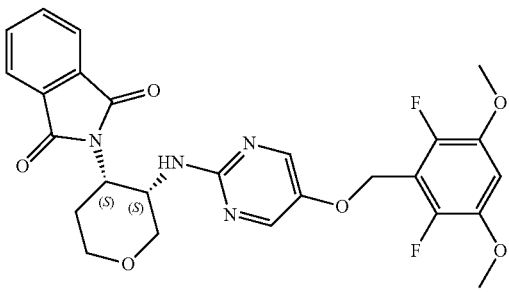

The control example 4C (170 mg, 0.5 mmol) was dissolved in an one-neck flask (50 containing acetonitrile (5 mL), into which were then added (2,6-difluoro-3,5-dimethoxyphenyl)methyl methane sulfonic acid (183 mg, 0.65 mmol), $Cs_2CO_3$ (325.5 mg, 1.0 mmol), the resultant mixture was reacted at 80-90° C. for 2 hours. The reaction solution was filtered, and the filtrate was concentrated to give a crude product, which was purified over a preparative plate (eluent PE:EA=1/1) to give the control example 4D (white solid, 140 mg, 43.65% yield).

LCMS (ESI) m/z: 527.1 [M+1]$^+$

Control Example 4E

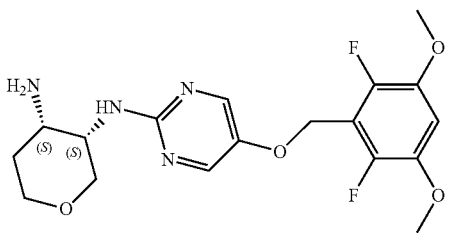

The control example 4D (100 mg, 0.19 mmol) was dissolved in ethanol (4.00 mL), into which was then added hydrazine hydrate (0.1 ml). The reaction solution was stirred at the temperature of 80-90° C. for 2 hours. The reaction solution was directly concentrated in vacuum to give a crude product, into which was added dichloromethane (5 ml) and stirred for 5 minutes. The resulting filtrate was filtered and then concentrated to give a crude product, which was purified over a preparative plate (eluent DCM/MeOH=10/1) to give the control example 4E (colorless oil, 45 mg, 59.77% yield).

LCMS (ESI) ink: 397.1 [M+1]$^+$

Control Example 4

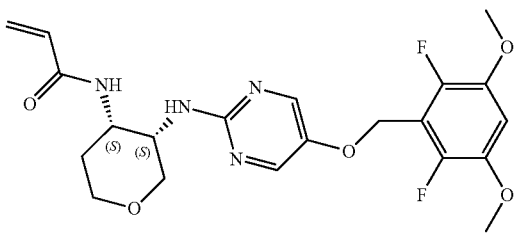

The control example 4E (35 mg, 88 μmol) was dissolved in a one-neck flask (50 ml) containing dichloromethane (3 mL), into which was then added DIEA (23 mg, 176 μmol). Propionyl chloride was diluted with dichloromethane (0.42 ml, 0.25 mol/l) and dropwise added into the reaction solution, which was stirred at 10-15° C. for 30 minutes. The reaction was quenched with 10 ml water, extracted with dichloromethane (20 ml). The organic layers were combined, then washed with saturated saline (10 ml), dried over anhydrous sodium sulfate, filtered, and concentrated in vacuum, the residue of which was purified over a preparative plate (DCM:MeOH=10:1) to give the control example 8 (white solid, 18 mg, 41.53% yield).

LCMS (ESI) m/z: 451.2 [M+1]$^+$ $^1$H NMR (400 MHz, METHANOL-$d_4$) δ 8.03 (s, 2H), 6.81 (t, J=8.3 Hz, 1H), 6.13-5.88 (m, 2H), 5.49 (dd, 1=2.6, 9.4 Hz, 1H), 5.00 (t, J=1.5 Hz, 2H), 4.31 (br s, 1H), 4.14 (td, J=4.1, 11.4 Hz, 1H), 3.87 (td, J=3.6, 11.5 Hz, 1H), 3.77 (s, 6H), 3.75-3.71 (m, 1H), 3.58 (dd, J=2.0, 11.8 Hz, 1H), 3.47 (dt, J=2.8, 11.4 Hz, 1H), 1.39-1.27 (m, 2H)

The control example 7 and control example 8 as below were prepared with reference to the process described in the control example 4.

| Example | Structure | NMR Data | LCMS (ESI) m/z: (M + 1) |
|---|---|---|---|
| Control example 7 | 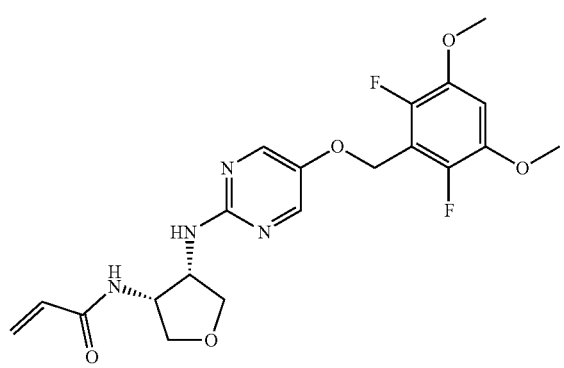 [SMILES: C=CC(=O)N[C@H]1COC[C@H]1Nc1ncc(OCc2c(F)c(OC)cc(OC)c2F)cn1] | $^1$H NMR (400 MHz, CHLOROFORM-d) δ 8.09-8.13 (m, 2H), 6.66 (t, J = 8.28 Hz, 1H), 6.59 (br d, J = 6.02 Hz, 1H), 6.19 (dd, J = 1.51, 17.07 Hz, 1H), 5.94-6.05 (m, 1H), 5.53-5.75 (m, 2H), 5.09 (s, 2H), 4.60-4.76 (m, 2H), 4.08-4.22 (m, 2H), 3.87 (s, 6H), 3.68-3.74 (m, 2H) | 436.9 |

| Example | Structure | NMR Data | LCMS (ESI) m/z: (M + 1) |
|---|---|---|---|
| Control example 8 | 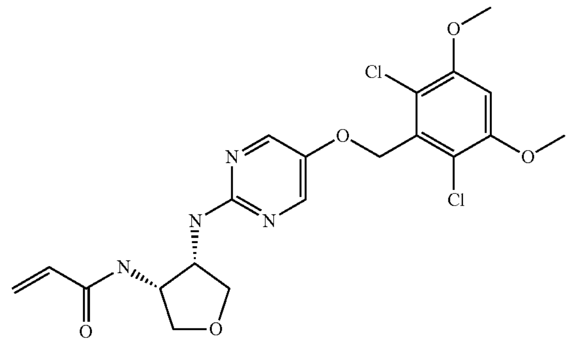 [SMILES: C=CC(=O)N[C@H]1COC[C@H]1Nc1ncc(OCc2c(Cl)c(OC)cc(OC)c2Cl)cn1] | $^1$H NMR (400 MHz, CHLOROFORM-d) δ 8.18 (s, 3H), 6.59-6.68 (m, 2H), 6.19-6.29 (m, 1H), 6.02-6.13 (m, 1H), 5.63 (dd, J = 1.38, 10.16 Hz, 1H), 5.30 (s, 2H), 4.81-4.91 (m, 1H), 4.74 (br d, J = 4.77 Hz, 1H), 4.14 (ddd, J = 6.27, 9.35, 13.49 Hz, 2H), 3.94 (s, 6H), 3.73-3.85 (m, 2H) | 490.8 [M + 23] |
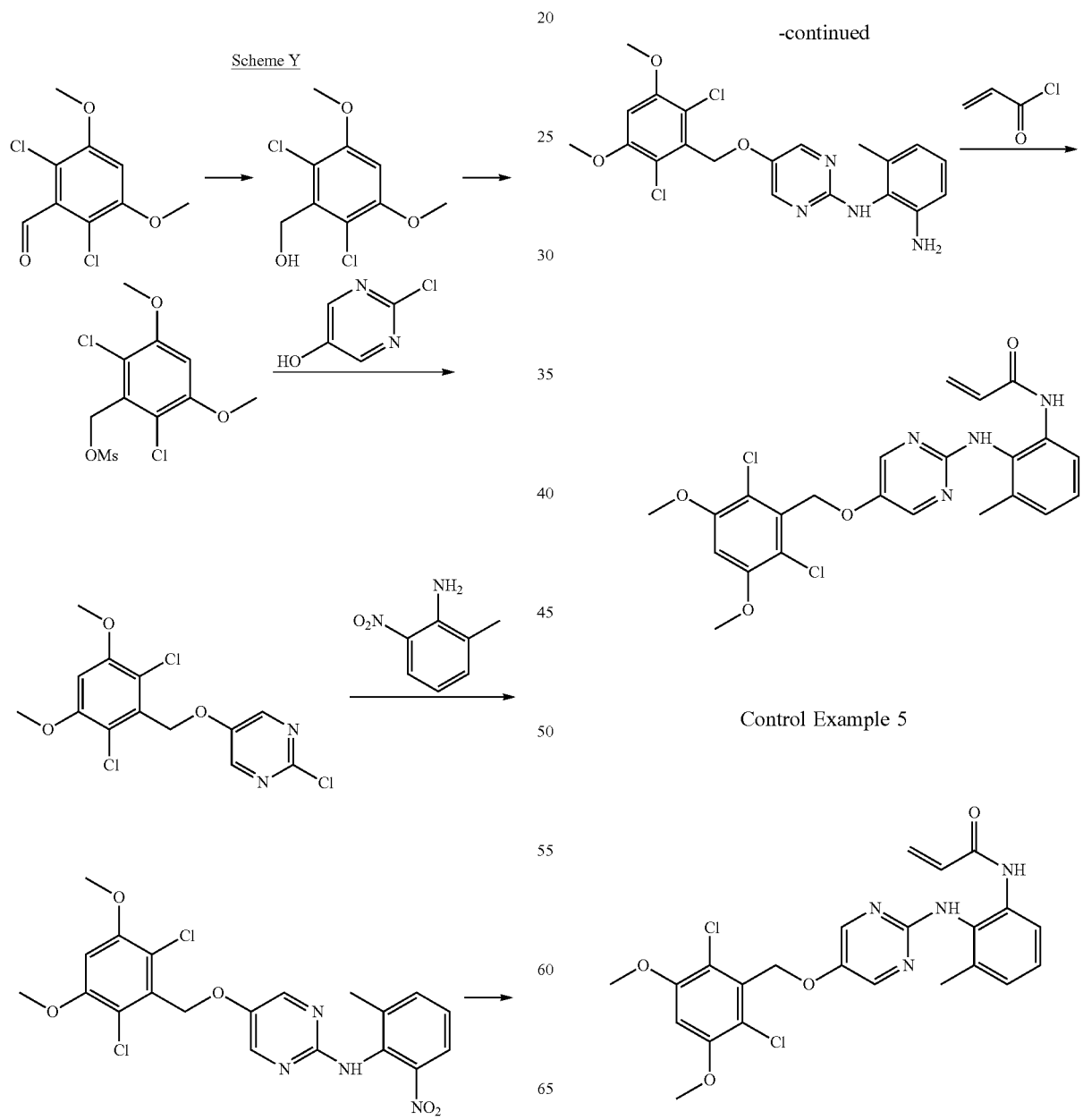

Control Example 5A

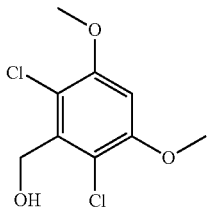

At 0° C., to a solution of 2,6-dichloro-3,5-dimethoxy benzaldehyde (1.00 g, 4.25 mmol) in ethanol (15.00 ml) was added NaBH$_4$ (321.56 mg, 8.50 mmol) batchwise. The mixture was reacted at 0° C. for 1 hour, and then reacted at 15° C. for 16 h. Upon the completion of the reaction, a saturated NH$_4$Cl solution (1 ml) was added to the reaction solution, then the mixture was extracted with ethyl acetate (2×10 ml), washed with saturated saline (10 ml), dried over anhydrous sodium sulfate, and filtered. The filtrate was concentrated at reduced pressure to give a crude control example 5A (1.00 g, yield 99.25%).

$^1$H NMR (400 MHz, CHLOROFORM-d) δ6.56 (s, 1H), 5.00 (d, J=7.2 Hz, 2H), 3.93 (s, 6H), 2.16 (t, J=7.2 Hz, 1H).

Control Example 5b

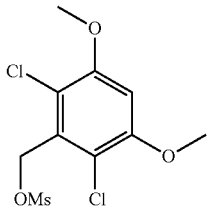 [SMILES: COc1cc(OC)c(Cl)c(COS(C)(=O)=O)c1Cl]

At 0° C., to a solution of the control example 5A (1.00 g, 4.22 mmol) and triethyl amine (640.53 mg, 6.33 mmol) in dichloromethane (20.00 ml) was dropwise added methane sulfonyl chloride (580.0 mg, 5.06 mmol). The reaction solution was reacted for 1 hour with stirring at 0° C. Upon the completion of reaction, the reaction was quenched with water (10 ml). Then the aqueous phase was extracted with dichloromethane (2×10 ml). The organic phase was combined, washed with saturated saline (10 ml), dried over anhydrous sodium sulfate, and filtered. The filtrate was concentrated at reduced pressure to give the control example 5B (1 g, yield: 96.9%).

$^1$H NMR (400 MHz, CHLOROFORM-d) δ=6.64 (s, 1H), 5.56 (s, 2H), 3.94 (s, 6H), 3.09 (s, 3H).

Control Example 5C

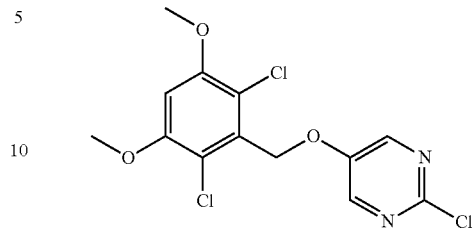

The control example 5B (447.2 mg, 3.43 mmol), 4-chloro, 5-hydroxy pyrimidine (447.2 mg, 3.43 mmol) and cesium carbonate (2.23 g, 6.85 mmol) were added into acetonitrile (15.00 ml). Then the reaction was heated to reflux in an oil bath. After the mixture was stirred for 1.0 h, LCMS detection showed that the reaction was completed. The reaction solution was diluted with water (10 ml), with adjusting the pH to 9. The organic phase was washed with water to neutral, then washed with saturated saline (10 ml), dried over anhydrous sodium sulfate, and filtered. The filtrate was concentrated at reduced pressure to give the control example 5C (1.02 g, yield 85.1%).

$^1$H NMR (400 MHz, CHLOROFORM-d) δ 8.40 (s, 2H), 6.64 (s, 1H), 5.43 (s, 2H), 3.95 (s, 6H).

Control Example 5D

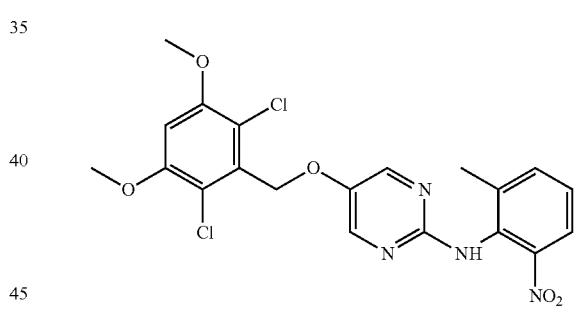

The control example 5C (300.00 mg, 0.86 mmol), 2-methyl-6-nitroaniline (195.85 mg, 1.29 mmol), Pd$_2$(dba)$_3$ (39.29 mg, 42.91 μmol), XPhos (81.82 mg, 171.62 μmol), cesium carbonate (559.19 mg, 1.72 mmol) and DMA (6.00 ml) were placed in a 100 ml one-neck flask equipped with a reflux condensing tube successively. After replacement with nitrogen for three times, the reaction mixture was heated to 110° C. in an oil bath and reacted for 3 hours. After the reaction was cooled to room temperature, the reaction solution was filtered, into which was added water (10 ml), and then extracted with ethyl acetate (10 ml×2). The organic phases were combined and washed with water (10 ml) and saturated saline (10 ml) successively, dried over anhydrous sodium sulfate, and filtered. The filtrate was concentrated at reduced pressure to give a crude product, which was purified over a flash silica gel column (mobile phase: 0~25% ethyl acetate/petroleum ether) to give the control example 5D (220 mg, yield: 55.1%) as a white solid.

LCMS (ESI): m/z=465.0, 467.0[M+1]$^+$.

¹H NMR (400 MHz, CHLOROFORM-d) 8.13 (s, 2H), 7.90 (s, 1H), 7.80 (d, J=8.0 Hz, 1H), 7.44 (d, J=7.6 Hz, 1H), 7.14 (t, J=7.6 Hz, 1H), 6.54 (s, 1H), 5.24 (s, 2H), 3.86 (s, 6H), 2.23 (s, 3H).

Control Example 5E

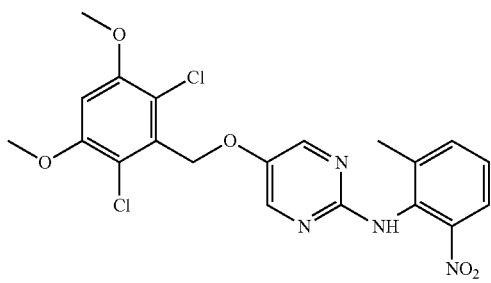 [SMILES: COc1cc(OC)c(Cl)c(COc2cnc(Nc3c(C)cccc3[N+](=O)[O-])nc2)c1Cl]

At 20° C., the control example 5D (220.00 mg, 472.82 μmol), reduced ferrous powder (132.03 mg, 2.36 mmol) and ammonium chloride (126.46 mg, 2.36 mmol) were added into a mixed solution of ethanol (8.00 ml) and water (1.60 ml). The reaction was then heated to reflux in an oil bath, stirred for 2 hours, and filtered. The reaction solution was extracted with ethyl acetate (10 ml×2). The organic phases were combined and washed with saturated saline (10 ml), dried over anhydrous sodium sulfate, and filtered. The filtrate was concentrated at reduced pressure to give the control example 5E (205.82 mg).

LCMS (ESI): m/z=435.1, 437.1[M+1]⁺.

Control Example 5

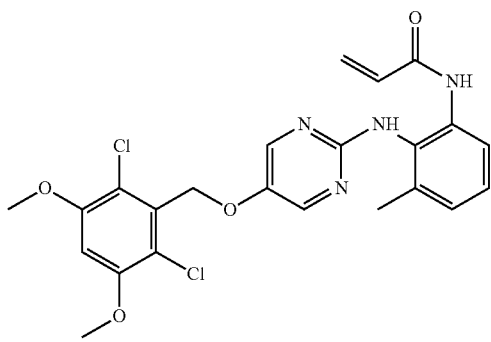 [SMILES: C=CC(=O)Nc1cccc(C)c1Nc1ncc(OCc2c(Cl)c(OC)cc(OC)c2Cl)cn1]

The control example 5E (195.00 mg, 447.97 μmol), DMA (173.69 mg, 1.34 mmol, 234.72 μL) and DCM (6.00 ml) were added into a 50 ml round-bottom flask, and the solution was cooled to 0° C. in an ice-water bath. Acryloyl chloride (38.52 mg, 425.57 mot, 34.70 μL) was dropwise added into the reaction solution and the mixture was reacted at 0° C. for 30 min, at which the reaction was showed to be complete based on LCMS detection. The reaction was quenched with ice-water (0.5 ml) and extracted with dichloromethane (2×10 ml). The dichloromethane solution was combined and washed with saturated saline (5 ml), dried over anhydrous sodium sulfate, and filtered. The filtrate was concentrated at reduced pressure to give the residue. The crude product was separated by neutral prep-HPLC, finally obtaining the target compound control example 5 (5 mg, yield 2.3%).

LCMS (ESI) m/z=489.0, 491.0 [M+1]⁺.

¹H NMR (400 MHz, CHLOROFORM-d) δ=8.25-8.17 (m, 3H), 8.07 (hr. s., 1H), 7.25-7.20 (m, 1H), 7.07 (d, J=7.6 Hz, 1H), 6.62 (s, 1H), 6.37-6.29 (m, 2H), 6.23-6.11 (m, 1H), 5.70 (d, J=10.4 Hz, 1H), 5.33 (s, 2H), 5.30 (s, 1H), 3.95 (s, 6H), 2.25 (s, 3H), 2.19 (s, 1H).

Scheme Z

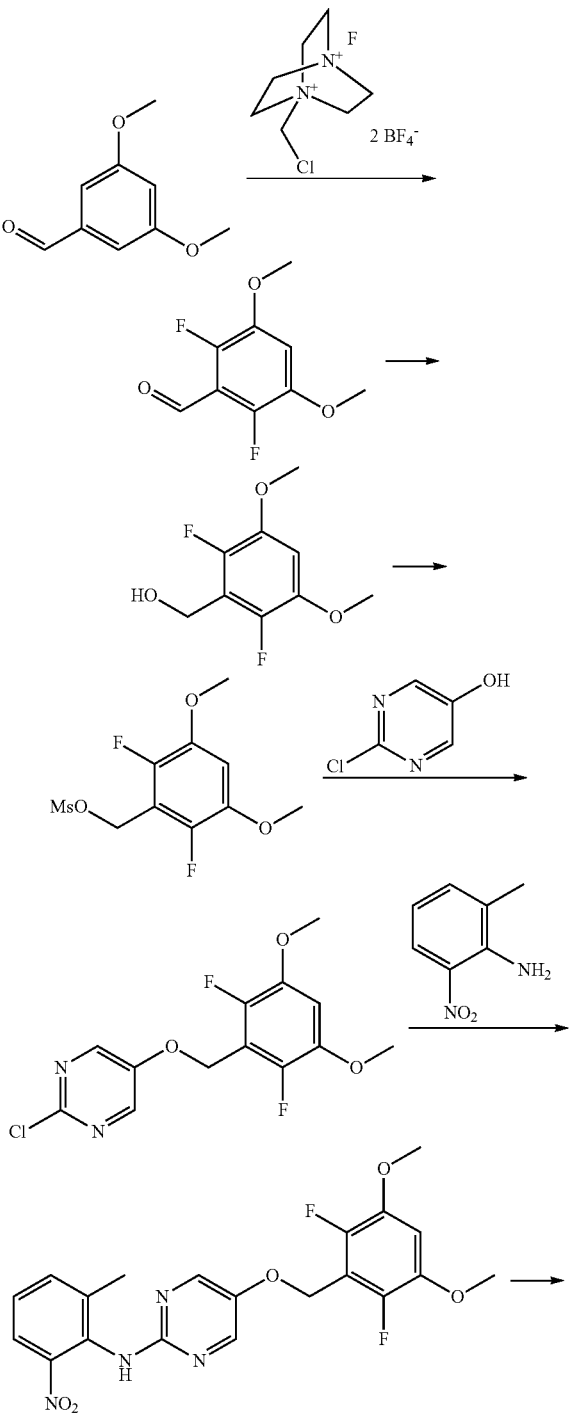

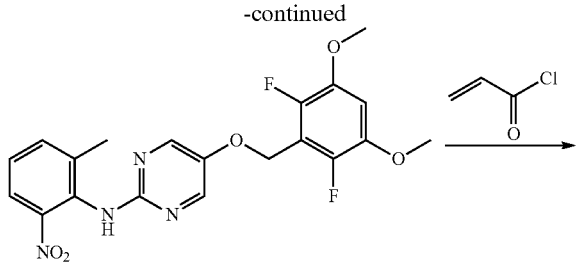

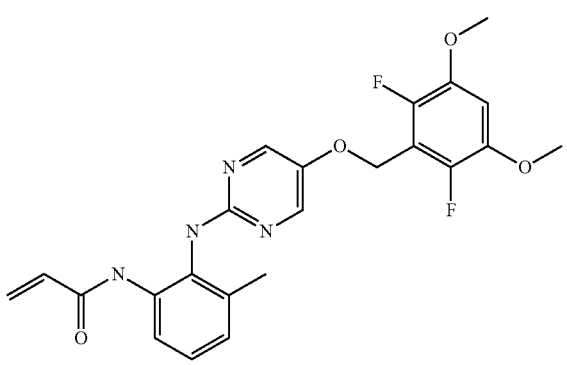 [SMILES: C=CC(=O)Nc1cccc(C)c1Nc1ncc(OCc2c(F)c(OC)cc(OC)c2F)cn1]

Control Example 6

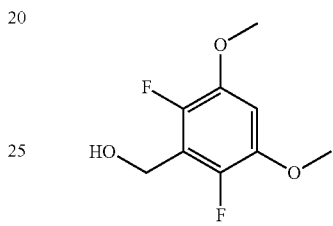

Control Example 6A

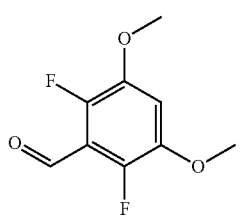

A solution of 3,5-dimethoxy benzaldehyde (1.00 g, 6.02 mmol) in CH₃CN (15 ml) was cooled to 0° C. in an ice-bath, into which was then added [2.2.2]octane di(tetrafluoroborate) salt (3.20 g, 9.03 mmol) batchwise. After the reaction solution was reacted at 0° C. for 1 hour, the temperature of the system rised slowly to 15° C., then kept on stirring for 16 hours. TLC showed that the raw materials disappeared, and there were primarily new spots generated. The reaction solution was concentrated at reduced pressure, obtaining an oily residue, which was diluted with water (10 ml), then adjusted to pH=7 with saturated NaHCO₃ (5%), and the mixture was extracted with ethyl acetate (3×10 ml). The ethyl acetate solution was combined and washed with saturated saline (10 ml), dried over anhydrous sodium sulfate, and filtered. The filtrate was concentrated at reduced pressure to give a residue. The crude product was purified over a flash silica gel column (mobile phase: 0-30% ethyl acetate/petroleum ether) to give a light yellow compound control example 6A (310 mg, yield: 25.5%).

LCMS (ESI) m/z: 202.8 [M+1]⁺

¹H NMR (400 MHz, CHLOROFORM-d) δ 10.36 (s, 1H), 6.89 (t, J=8.2 Hz, 1H), 3.92 (s, 6H).

Control Example 6B

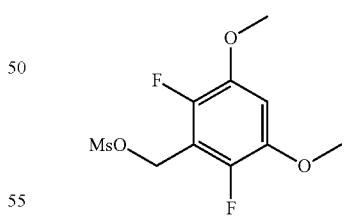

At 0° C., to a solution of the control example 6A (310 mg, 1.53 mmol) in ethanol (6.0 ml) was added sodium borohydride (116 mg, 3.06 mmol). The reaction solution was stirred continuously at 0° C. for 60 minutes (until no gas discharge). The reaction was quenched with a saturated aqueous solution of ammonium chloride (5 ml), concentrated at reduced pressure to remove most ethanol, diluted with water (20 ml), and then extracted with ethyl acetate (2×10 ml). The ethyl acetate solution was combined and washed with saturated saline (10 ml), dried over anhydrous sodium sulfate, and filtered. The filtrate was concentrated at reduced pressure to give the control example 6B (290 mg, yield: 92.8%) as a white solid.

Control Example 6C

At 0° C., to a solution of the control example 6B (290.00 mg, 1.42 mmol) and triethyl amine (287 mg, 2.84 mmol) in dichloromethane (6.0 ml) was dropwise added methane sulfonyl chloride (195 mg, 1.70 mmol) slowly, the reaction solution (N₂ protection) was reacted further at 0° C. for 1.5 hours. The reaction was quenched with water (5 ml), partitioned, and the aqueous phase was extracted with dichloromethane (2×5 ml). The organic phase was combined and washed with saturated saline (5 ml), dried over anhydrous sodium sulfate, and filtered. The filtrate was concentrated at reduced pressure to give the control example 6C (440 mg, crude), which was used directly in the next reaction step without being purified.

Control Example 6D

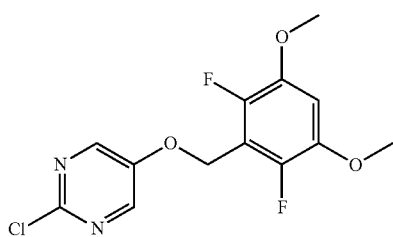 [SMILES: COc1cc(OC)c(F)c(COc2cnc(Cl)nc2)c1F]

To a solution of the crude control example 6C (440 mg, 1.56 mmol) and 2-chloro-5-hydroxypyridine (203.48 mg, 1.56 mmol) in CH$_3$CN (8.00 ml) was added Cs$_2$CO$_3$ (762.42 mg, 2.34 mmol) as a solid, then the reaction solution was heated to reflux and stirred for 2 hours. LCMS showed that the raw materials have been converted completely, with products being generated. When the reaction solution was cooled to room temperature, the reaction was quenched with (5 ml), partitioned, and the aqueous phase was extracted with ethyl acetate (2×10 ml). The organic phases were combined and washed with saturated saline (10 ml), dried over anhydrous sodium sulfate, and filtered. The filtrate was concentrated at reduced pressure to give a crude product, which was purified over a flash silica gel column (mobile phase: 0-20% ethyl acetate/petroleum ether) to give a white solid compound control example 6D (188.00 mg, yield: 33.87%).

LCMS (ESI) m/z: 316.9, 318.9[M+1]$^+$

Control Example 6E

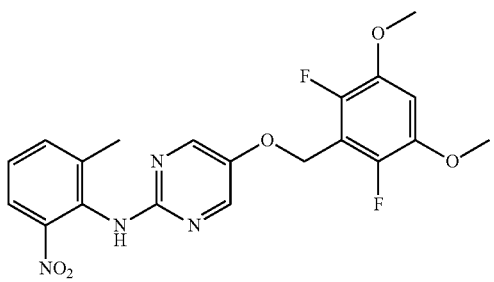 [SMILES: COc1cc(OC)c(F)c(COc2cnc(Nc3c(C)cccc3[N+](=O)[O-])nc2)c1F]

The control example 6D (188 mg, 594 μmol), 2-methyl-6-nitroaniline (135 mg, 890 μmol), Pd(dba)$_2$ (34 mg, 59 μmol), XPhos (56 mg, 118 μmol), Cs$_2$CO$_3$ (386.84 mg, 1.19 mmol) and DMA (4.0 ml) were placed into a 20 ml sealed tube successively. After replacement with nitrogen for three times, the reaction mixture was heated to 110° C. and reacted for 3 hours. TLC detection on the reaction showed that the raw materials have been converted completely. After being cooled to room temperature, the reaction was diluted with water (10 ml), and then extracted with ethyl acetate (3×10 ml). The organic phases were combined and washed with saturated saline (10 ml), dried over anhydrous sodium sulfate, and filtered. The filtrate was concentrated at reduced pressure to give a crude product, which was purified over a flash silica gel column (mobile phase: 0-40% ethyl acetate/petroleum ether) to give the yellow solid compound control example 6E (202 mg, yield: 78.70%).

LCMS (ESI) m/z: 433.0 [M+1]$^+$

Control Example 6F

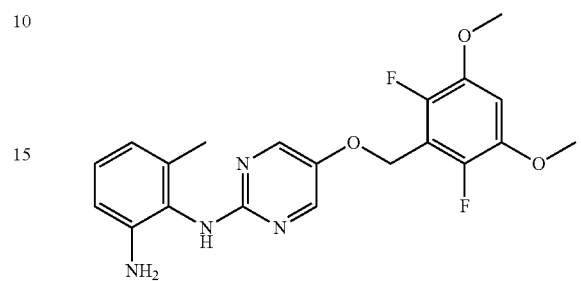

At room temperature, reduced ferrous powder (129 mg, 2.31 mmol) and NH$_4$Cl (124 mg, 2.31 mmol) were added into a mixed solution of the compound control example 6E (200 mg, 463 μmol) in EtOH (5.0 ml) and H$_2$O (1.0 ml), the reaction was then heated to reflux in an oil bath, stirred for 1.0 hours, and filtered. The filtrate was concentrated at reduced pressure to give a crude product. The solid was diluted with ethyl acetate (20 ml), and then adjusted to pH=8 with a saturated aqueous solution of sodium bicarbonate, the liquid was partitioned, the aqueous phase was extracted with ethyl acetate (10 ml×2). The ethyl acetate phases were combined and washed with saturated saline (10 ml), dried over anhydrous sodium sulfate, and filtered. The filtrate was concentrated at reduced pressure to give the control example 6F (180.00 mg, yield: 96.71%) as a yellow solid.

LCMS (ESI) m/z: 403.0[M+1]$^+$

Control Example 6

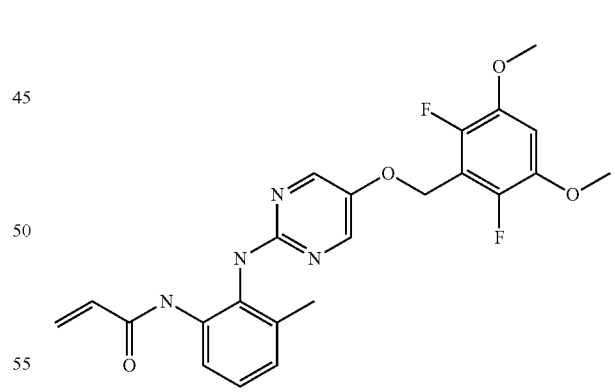

At 0° C., acryloyl chloride (40 mg, 448 μmol) was added to a solution of the control example 6F (180 mg, 447 μmol) and N-ethyldiisopropyl amine (116 mg, 895 μmol) in dichloromethane (5.0 ml), the reaction was stirred at 0° C. for 30 minutes. LCMS showed that the reaction was completed. The reaction was quenched with ice-water (2 ml), and then extracted with ethyl acetate (2×5 ml). The organic solvents were combined and washed with saturated saline (5 ml), dried over anhydrous sodium sulfate, and filtered. The filtrate was concentrated at reduced pressure to give a residue, which was separated over a flash silica gel column (mobile phase: 0~50% ethyl acetate/petroleum ether) to give a light yellow compound control example 6 (155 mg, yield: 74.4%).

LCMS (ESI) m/z: 457.1 [M+1]⁺

¹H NMR (400 MHz, CHLOROFORM-d) δ 8.22 (br. s., 1H), 8.16 (s, 2H), 8.04 (d, J=6.0 Hz, 1H), 7.22 (t, J=8.0 Hz, 1H), 7.06 (d, J=7.6 Hz, 1H), 6.67 (t, J=8.0 Hz, 1H), 6.45 (br. s., 1H), 6.36-6.28 (m, 1H), 6.20-6.11 (m, 1H), 5.68 (d, J=11.2 Hz, 1H), 5.12 (s, 2H), 3.88 (s, 6H), 2.22 (s, 3H).

Scheme D

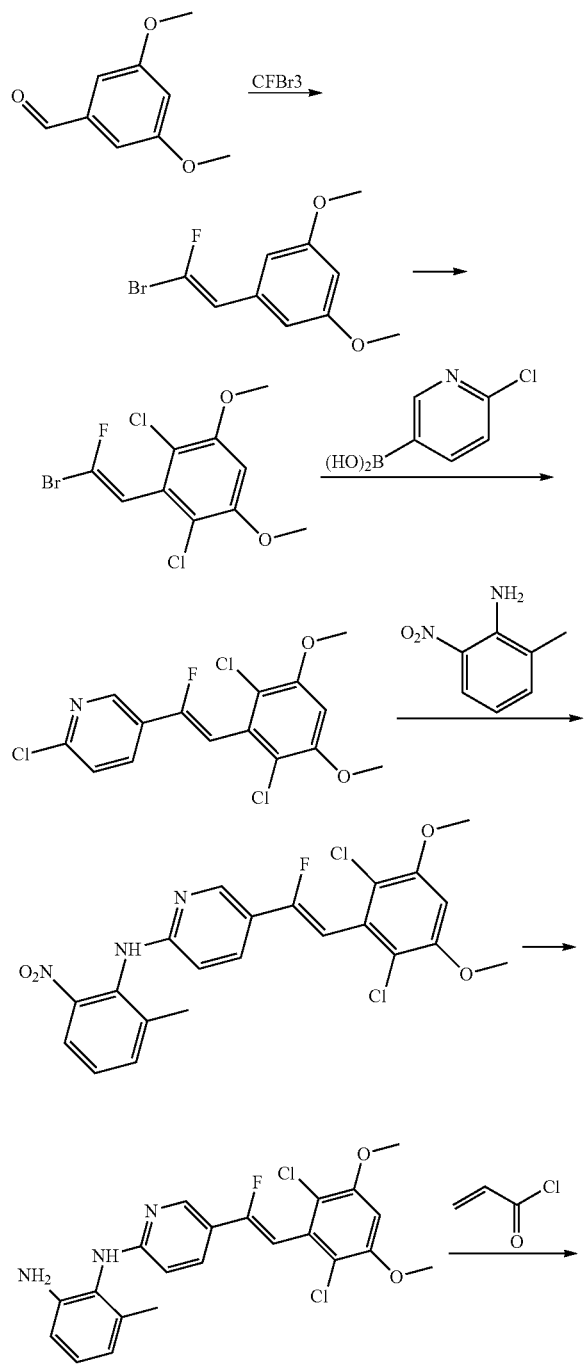

Example 1

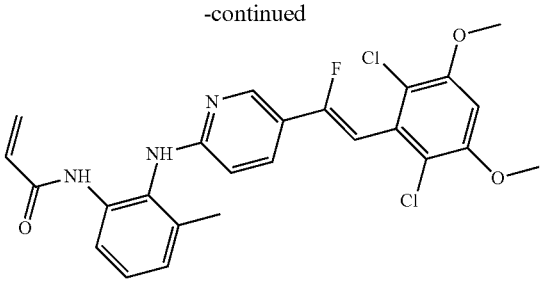

Example 1A

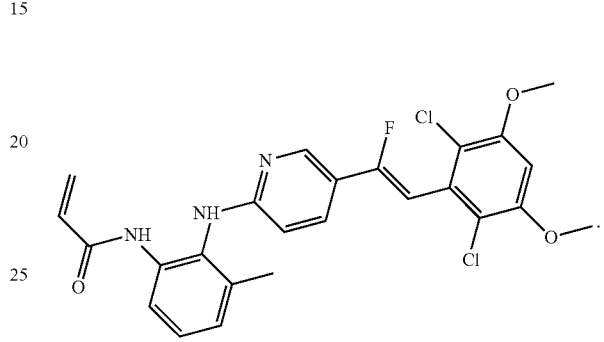

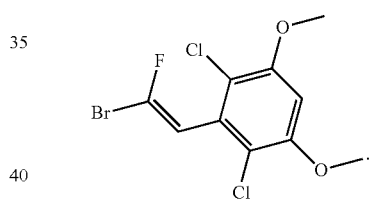

At room temperature (28° C.), hydrazine hydrate (18.1 g, 361 mmol) was dropwise added into 3,5-dimethoxy benzaldehyde (20 g, 120 mmol). At room temperature, after stirring for 2 hours, TLC detection showed that 3,5-dimethoxy benzaldehyde has not reacted completely, thus prolonging the reaction time. After continuously reacting for 16 hours, ethylenediamine (21.70 g, 361 mmol) and cuprous chloride (1.19 g, 12.04 mmol) were added to the reaction flask. After stirring for 30 minutes, the reaction solution was cooled to 0° C. in an ice-bath, then a solution of tribromofluoromethane (81.46 g, 301 mmol) in ethanol (30 ml) was dropwise added into the reaction solution through a constant pressure dropping funnel (with a little gas being released during the dropwise addition). Upon the completion of the dropwise addition, the reaction was stirred at 0° C. for 1 hour, then warmed slowly to room temperature (28° C.) and then reacted further for 1 hour. When the intermediate E-3,5-dimethoxy phenylhydrazone was completely reacted, the mixture was filtered, the solid was washed with ethyl acetate, the filtrate was concentrated at reduced pressure to evaporate off most of the solvents. The reaction was diluted with ethyl acetate (200 ml), and washed with an aqueous solution of citric acid (1M, 50 ml), partitioned, and the aqueous phase was then extracted with ethyl acetate (3×100 ml). The organic phases were combined and washed with saturated saline (150 ml), dried over anhydrous sodium sulfate, and filtered. The filtrate was concentrated at reduced pressure to give a crude product, which was purified over a flash silica gel column (mobile phase: 0-15% ethyl acetate/petroleum ether) to give the Example 1A (18.86 g, yield: 60%) as a light yellow liquid.

1H NMR (400 MHz, CHLOROFORM-d) δ 6.56 (d, J=2.4 Hz, 2H), 6.43-6.39 (m, 1H), 5.92 (d, J=32.4 Hz, 1H), 3.80 (s, 6H).

Example 1B

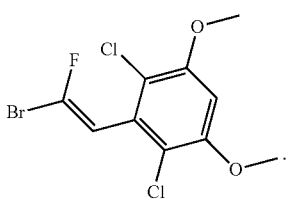 [SMILES: COc1cc(OC)c(Cl)c(/C=C(\F)Br)c1Cl]

A-A solution of Example 1A (18.86 g, 72.24 mmol) in anhydrous tetrahydrofuran (360 ml) was cooled to −20° C., into which was then dropwise added sulfonyl chloride (24.38 g, 180.6 mmol, 18.1 ml) slowly. Upon the completion of the dropwise addition, the reaction solution was further reacted at −20° C. for 1 hour. The reaction was quenched with water (20 ml), neutralized to pH=7 with a 5% aqueous solution of sodium bicarbonate. The reaction was then extracted with ethyl acetate (3×100 ml). The organic phases were combined and washed with saturated saline (150 ml), dried over anhydrous sodium sulfate, and filtered. The filtrate was concentrated at reduced pressure to give the Example 1B (21.64 g, yield: 91%) as a light yellow solid.

1H NMR (400 MHz, CHLOROFORM-d) δ 6.56 (s, 1H), 6.11-5.99 (d, J=31.6 Hz, 1H), 3.93 (s, 6H)

Example 1C

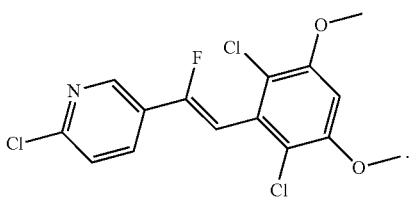 [SMILES: COc1cc(OC)c(Cl)c(/C=C(\F)c2ccc(Cl)nc2)c1Cl]

Example 1B (600 mg, 1.82 mmol), 3,5-dimethoxyphenylboronic acid (435 mg, 1.82 mmol), Pd(dppf)Cl$_2$ (133 mg, 182 μmol) and potassium phosphate (966 mg, 4.55 mmol) were placed in a 50 ml sealed tube, into which were added tetrahydrofuran (9.0 ml) and water (3.0 ml) respectively. After replacement with nitrogen for three times, the reaction solution was heated to 80° C. in an oil bath and then reacted for 2 hours. The reaction was cooled to room temperature, then diluted with water (5 ml), and then extracted with ethyl acetate (2×10 ml). The organic phases were combined and washed with saturated saline (10 ml), dried over anhydrous sodium sulfate, and filtered. The filtrate was concentrated at reduced pressure to give a crude product, which was purified over a flash silica gel column (mobile phase: 0-16% ethyl acetate/petroleum ether) to give the Example 1C (302 mg, yield: 42.6%) as a white solid.

LCMS (ESI) m/z: 363.8, 361.8[M+1]$^+$.

Example 1D

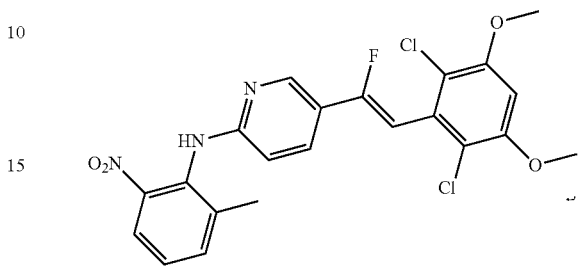

Example 1C (300 mg, 827 μmol), 2-methyl-6-nitroaniline (189 mg, 1.24 mmol), Pd$_2$(dba)$_3$ 76 mg, μmol), Xphos (79 mg, 165 μmol) and N,N-dimethyl acetamide (6.0 ml) were respectively placed in a 50 ml one-neck flask equipped with a reflux condensing tube successively. After replacement with nitrogen for three times, the reaction mixture was heated to 110° C. in an oil bath and reacted for 2 hours. After the reaction was cooled to room temperature, the reactants were poured into water (20 ml), and extracted with ethyl acetate (3×10 ml). The organic phases were combined and washed with water (3×15 ml) and saturated saline (15 ml) successively, dried over anhydrous sodium sulfate, and filtered. The filtrate was concentrated at reduced pressure to give a crude product, which was purified over a flash silica gel column (mobile phase: 0-25% ethyl acetate/petroleum ether) to give the Example 1D (243 mg, yield: 71%).

LCMS (ESI) m/z: 363.8, 361.8[M+1]$^+$.

Example 1E

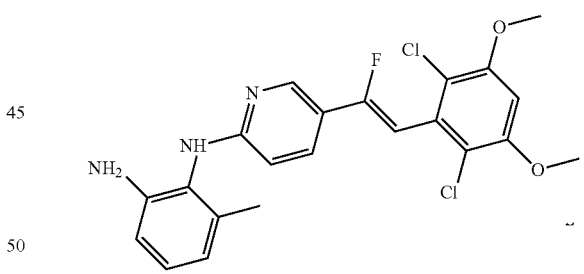

At room temperature, reduced ferrous powder (142 mg, 2.54 mmol) was added into a solution of Example 1D (243 mg, 508 μmol) and ammonium chloride (136 mg, 2.54 mmol) in ethanol (95%, 6.0 ml), the reaction was then heated to reflux in an oil bath. After stirring for 1.5 hours, the reaction solution was filtered while hot, the solid was rinsed with ethanol, and the filtrate was concentrated at reduced pressure to give a brown solid. The solid was partitioned between ethyl acetate (20 ml) and water (10 ml), and adjusted to pH=9 with saturated sodium bicarbonate. The water phase was then extracted with ethyl acetate (2×5.0 ml). The organic phases were combined and washed with saturated saline (10 ml), dried over anhydrous sodium sulfate, and filtered. The filtrate was concentrated at reduced pressure to give a crude product, which was purified over a flash silica gel column (mobile phase: 0-40% ethyl acetate/petroleum ether) to give a crude product Example 1E (41 mg).

LCMS (ESI) m/z: 448.0, 450.0 [M+1]⁺.

Example 1

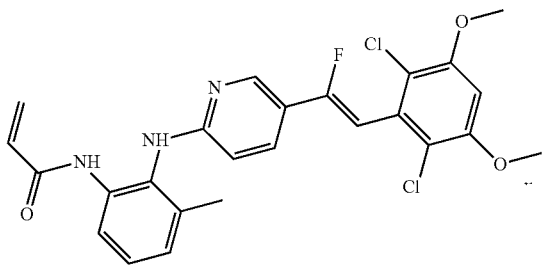 [SMILES: C=CC(=O)Nc1cccc(C)c1Nc1ccc(/C(F)=C/c2c(Cl)c(OC)cc(OC)c2Cl)cn1]

Example 1E (41 mg, 89 μmol), N,N-diisopropyl ethyl amine (23 mg, 178 μmol) and dichloromethane (2.0 ml) were added into a 50 ml round-bottom flask, and the solution was cooled to 0° C. in an ice-water bath. Acryloyl chloride (7.3 mg, 80 μmol) was dropwise added, the reaction solution was reacted at 0° C. for 30 minutes. When LCMS detection showed that the reaction has been completed, the reaction was quenched with ice-water (2.0 ml), diluted with 5.0 ml dichloromethane, and extracted with dichloromethane (2×5.0 ml). The dichloromethane solution was combined and washed with saturated saline (5.0 ml), and post-treated to give a crude product, which was separated by preparative high performance liquid chromatography (trifluoroacetic acid system) to give the target compound Example 1 (5.0 mg, yield: 11%).

LCMS (ESI) m/z: 502.1, 504.1 [M+1]⁺.

¹H NMR (400 MHz, CHLOROFORM-d) δ 11.30 (br. s., 1H), 8.31 (br. s., 1H), 8.21 (d, J=1.6 Hz, 1H), 8.00 (dd, J=8.8, 8.8 Hz, 2H), 7.34 (dd, J=8.0, 8.0 Hz, 1H), 7.13 (d, J=7.6 Hz, 1H), 6.61-6.57 (m, 1H), 6.53 (d, J=9.6 Hz, 1H), 6.42-6.36 (m, 1H), 6.32-6.20 (m, 2H), 5.75 (d, J=10.0 Hz, 1H), 3.98-3.93 (m, 6H), 2.24 (s, 3H).

The following examples were prepared according to the process as described in Example 1.

| Example | Structure | NMR Data | LCMS (ESI) m/z: (M + 1) |
|---|---|---|---|
| Example 5 | 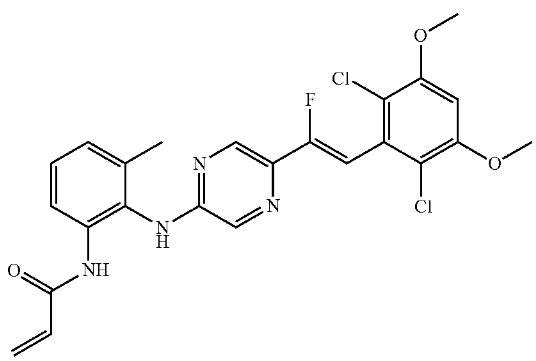 [SMILES: C=CC(=O)Nc1cccc(C)c1Nc1cnc(/C(F)=C/c2c(Cl)c(OC)cc(OC)c2Cl)cn1] | ¹H NMR (400 MHz, CHLOROFORM-d) δ8.14 (s, 1 H), 8.08 (s, 2 H), 7.79 (m, 1 H), 7.37 (m, 1 H), 7.22 (d, J = 7.6 Hz, 1 H), 6.89 (d, J = 38.0 Hz, 1 H), 6.60 (s, 1 H), 6.42 (d, J = 16.8 Hz, 1 H), 6.26 (d, J = 16.8, 10.0 Hz, 1 H), 5.82 (d, J = 10.0 Hz, 1 H), 3.96 (s, 6 H), 2.29 (s, 3 H). | 503.1, 505.1 |
| Example 6 | 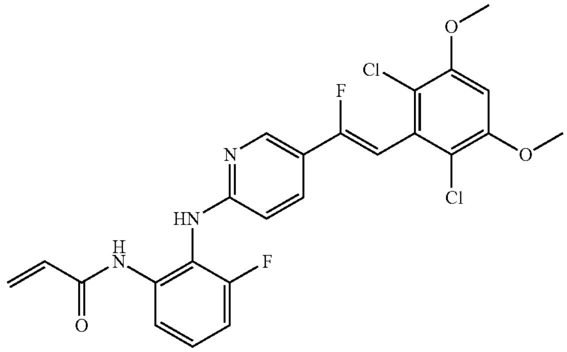 [SMILES: C=CC(=O)Nc1cccc(F)c1Nc1ccc(/C(F)=C/c2c(Cl)c(OC)cc(OC)c2Cl)cn1] | ¹H NMR (400 MHz, METHANOL-d₄) δ8.34 (d, J = 2.0 Hz, 1H), 7.85-7.94 (dd, J = 8.0, 2.0 Hz, 1H), 7.67 (d, J = 8.4 Hz, 1H), 7.26-7.40 (m, 1H), 7.11 (dd, J = 8.8, 8.8 Hz, 1H), 6.82 (s, 1H), 6.71 (d, J = 8.8 Hz, 1H), 6.23-6.51 (m, 3H), 5.73-5.84 (dd, J = 10.0, 2.0 Hz, 1H), 3.96 (s, 6H) | 506.1, 508.1 |

Scheme E

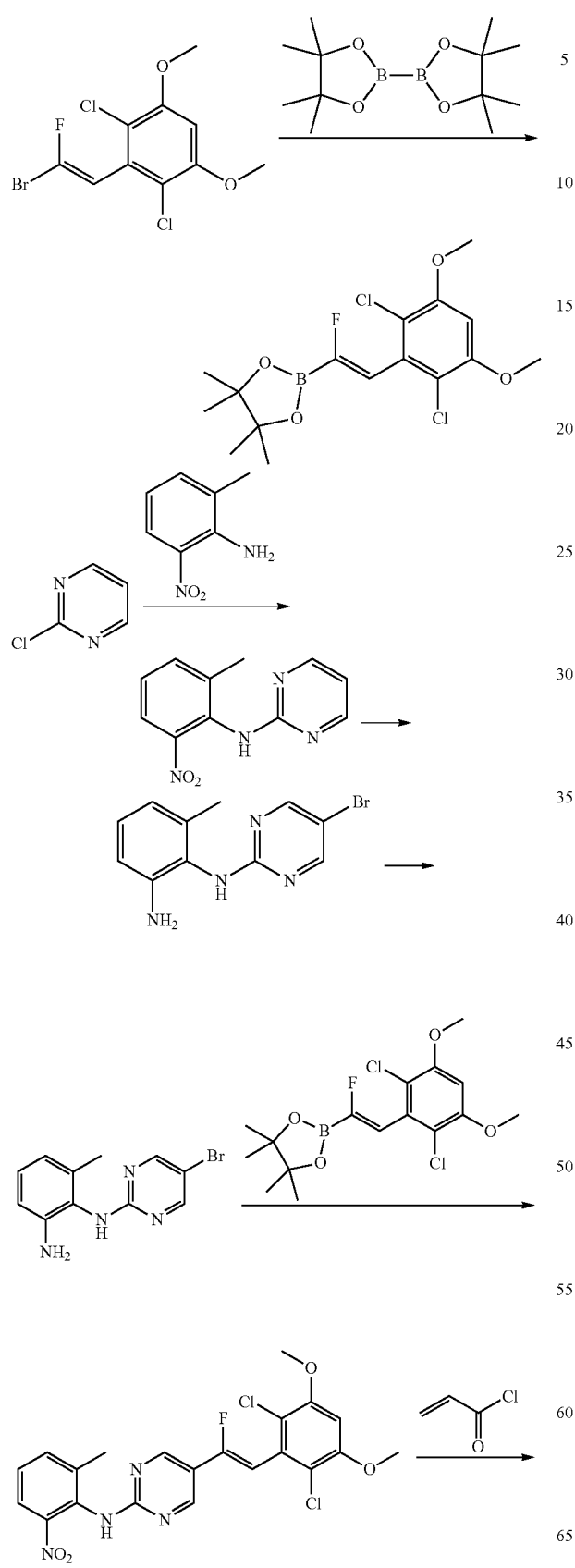

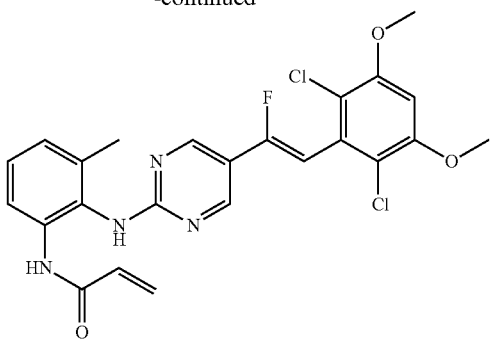

Example 2

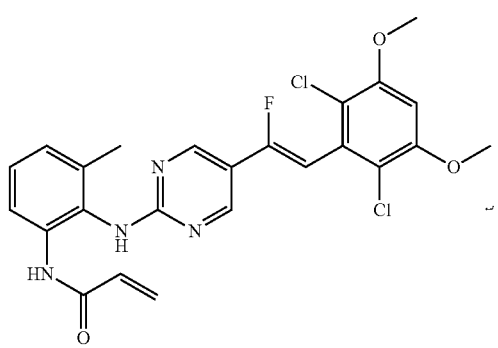 [SMILES: C=CC(=O)Nc1cccc(C)c1Nc1ncc(/C(F)=C/c2c(Cl)c(OC)cc(OC)c2Cl)cn1]

Example 2A

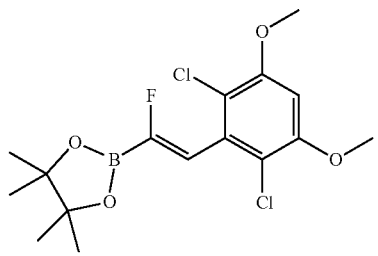

To a mixture of Example 1A (2.00 g, 6.06 mmol), bis(pinacolato)diboron (3.08 g, 12.12 mmol) and potassium acetate (1.78 g, 18.2 mmol) in dioxane (30 ml) was added Pd(dppf)Cl$_2$·CH$_2$Cl$_2$ (495 mg, 606 μmol). The reaction solution was replaced with nitrogen for 3 times, and then stirred at 90° C. for 16 hours under the atmosphere of nitrogen. When TLC detection showed that the reaction has been completed, after the reactants were cooled to room temperature, the mixture was diluted with ethyl acetate, and filtered. The filtrate was concentrated at reduced pressure to give a crude product, which was separated over a flash silica gel column (petroleum ether:ethyl acetate=0%-20%) to give the compound Example 2A (2.25 g, yield: 98.5%) as a white solid.

$^1$H NMR (400 MHz, CHLOROFORM-d) δ 6.57-6.41 (m, 2H), 3.92 (s, 6H), 1.36 (s, 12H).

Example 2B

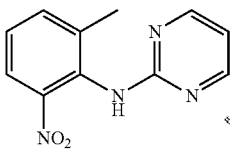

A mixed solution of 2-chloropyrimidine (3.00 g, 26.19 mmol), 2-methyl-6-nitroaniline (3.98 g, 26.2 mmol), Pd$_2$(dba)$_3$ (1.20 g, 1.31 mmol), Xphos (1.25 g, 2.62 mmol), cesium carbonate (17.07 g, 52.4 mmol) in N,N-dimethyl acetamide (100 ml) was replaced with nitrogen for 3 times, and then stirred at 100° C. for 3 hours under the atmosphere of nitrogen. The reaction was quenched with 100 ml water, extracted with ethyl acetate (100 ml×3). The organic layers were combined, washed with saturated saline (150 ml×2), dried over anhydrous sodium sulfate, filtered, and concentrated in vacuum, the residue of which was purified over a flash silica gel column (the proportion of petroleum ether/ethyl acetate: 5/1) to give the title compound Example 2B (4.50 g, yield: 74.6%) as a yellow solid.

LCMS (ESI) m/z: 231.0 [M+1]$^+$ $^1$H NMR (400 MHz, CHLOROFORM-d) δ 8.37 (d, J=4.8 Hz, 1H), 7.92 (br. s., 1H), 7.86 (d, J=8.4 Hz, 1H), 7.53 (d, J=7.2 Hz, 1H), 7.26-7.30 (m, 1H), 6.74 (m, 1H), 2.33 (s, 3H).

Example 2C

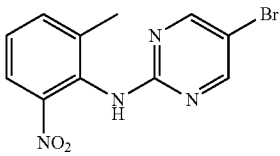

To a solution of Example 2B (500 mg, 2.17 mmol) in chloroform (5 ml) was added NBS (425 mg, 2.39 mmol), and the mixture was concentrated in vacuum, the residue of which was purified over a flash silica gel column (the proportion of petroleum ether/ethyl acetate: 5/1) to give the title compound Example 2C (640 mg, yield: 95.4%) as a brown solid.

LCMS (ESI) m/z: 310.9, 312.9 [M+1]$^+$

Example 2D

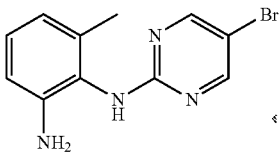 [SMILES: Cc1cccc(N)c1Nc1ncc(Br)cn1]

To a solution of Example 2C (640 mg, 2.07 mmol) in ethanol (10 ml) were added ferrous powder (578 mg, 10.4 mmol), ammonium chloride (554 mg, 10.4 mmol), the mixture was stirred at 90° C. for 2 hours, then filtered, and concentrated in vacuum, the residue of which was purified over a flash silica gel column (the proportion of petroleum ether/ethyl acetate: 3/1) to give the compound Example 2 D (423 mg, yield: 73.4%) as a yellow solid.

$^1$H NMR (400 MHz, DMSO-d6) δ 8.53 (s, 1H), 8.37 (br. s., 2H), 6.85 (dd, J=7.6, 7.6 Hz, 1H), 6.56 (d, J=7.6 Hz, 1H), 6.42 (d, J=7.2 Hz, 1H), 4.71 (s, 2H), 1.96-2.05 (m, 3H).

Example 2F

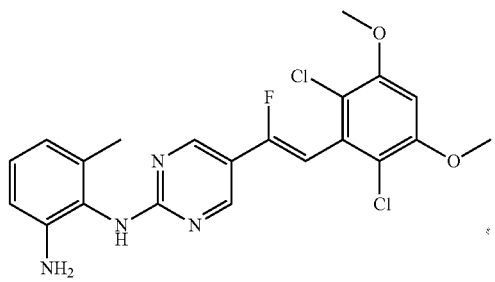 [SMILES: COc1cc(OC)c(Cl)c(/C=C(\F)c2cnc(Nc3c(C)cccc3N)nc2)c1Cl]

A mixed solution of Example 2D (373 mg, 1.34 mmol), Example 2A (606 mg, 1.34 mmol), Pd$_2$(dba)$_3$ (122 mg, 133 μmol), Xphos (127 mg, 267 μmol), potassium phosphate (567 mg, 2.67 mmol) in acetonitrile (3.0 ml) and water (1.0 ml) was replaced with nitrogen for 3 times and the mixture was stirred at 100° C. for 2 hours under the atmosphere of nitrogen. The reaction was quenched with 10 ml water, extracted with ethyl acetate (10 ml×3), the organic layers were combined and then washed with saturated saline (10 ml), dried over anhydrous sodium sulfate, filtered, and concentrated in vacuum, the residue of which was purified over a flash silica gel column (the proportion of petroleum ether/ethyl acetate: 3/1) to give the compound Example 2F (250 mg, yield: 41.5%) as a yellow oil.

LCMS (ESI) m/z: 449.2, 451.2 [M+1]$^+$ $^1$H NMR (400 MHz, DMSO-d6) δ 8.82 (s, 1H), 8.51-8.80 (m, 2H), 6.92 (s, 1H), 6.88 (dd, J=7.6, 7.6 Hz, 1H), 6.49-6.64 (m, 2H), 6.45 (d, J=7.2 Hz, 1H), 4.74 (br. s., 2H), 3.82-3.99 (m, 6H), 2.00-2.07 (m, 3H)

Example 2

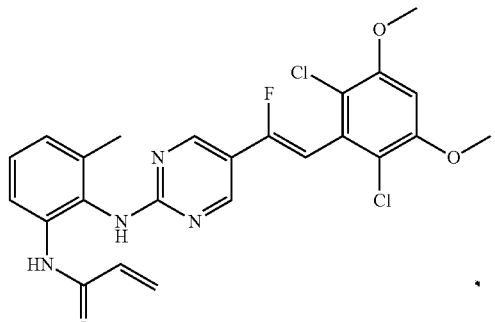

To a solution of Example 2F (250 mg, 556 μmol) in dichloromethane (5.0 ml) were added N,N-diisopropyl ethyl amine (180 mg, 1.39 mmol) and acryloyl chloride (50 mg, 556 μmol) at 0° C., and the mixture was stirred at 0° C. for 30 minutes. The reaction was quenched with 10 ml water, extracted with dichloromethane (10 ml×2), the organic layers were combined, and concentrated in vacuum, the residue of which was purified by preparative HPLC (trifluoroacetic acid system) to give the compound Example 2 (66 mg, yield: 23.1%).

LCMS (ESI) m/z: 503.1, 505.1 [M+1]+

$^1$H NMR (400 MHz, DMSO-d6) δ 9.47 (s, 1H), 8.86 (s, 1H), 8.70 (br. s., 1H), 7.72 (d, J=7.6 Hz, 1H), 7.15-7.25 (m, 1H), 7.09 (d, J=7.6 Hz, 1H), 6.88-6.96 (m, 1H), 6.64 (s, 1H), 6.47-6.59 (m, 1H), 6.22 (d, J=17.2 Hz, 1H), 5.71 (d, J=10.4 Hz, 1H), 3.93 (s, 6H), 2.13 (s, 3H).

The following example was prepared according to the process as described in Example 2.

| Example | Structure | NMR Data | LCMS (ESI) m/z: (M + 1) |
|---------|-----------|----------|-------------------------|
| Example 3 | | $^1$H NMR (400 MHz, METHANOL-d4) δ 8.35 (br. s., 1H), 7.54 (d, J = 7.6 Hz, 1H), 7.17-7.33 (m, 2H), 6.82 (s, 1H), 6.27-6.47 (m, 2H), 6.01-6.14 (m, 1H), 5.68-5.78 (m, 1H), 3.95 (s, 6H), 3.89 (d, J = 4.4 Hz, 1H), 2.54 (br. s., 2H), 2.21-2.30 (m, 3H) | 517.2, 519.2 |

Scheme F

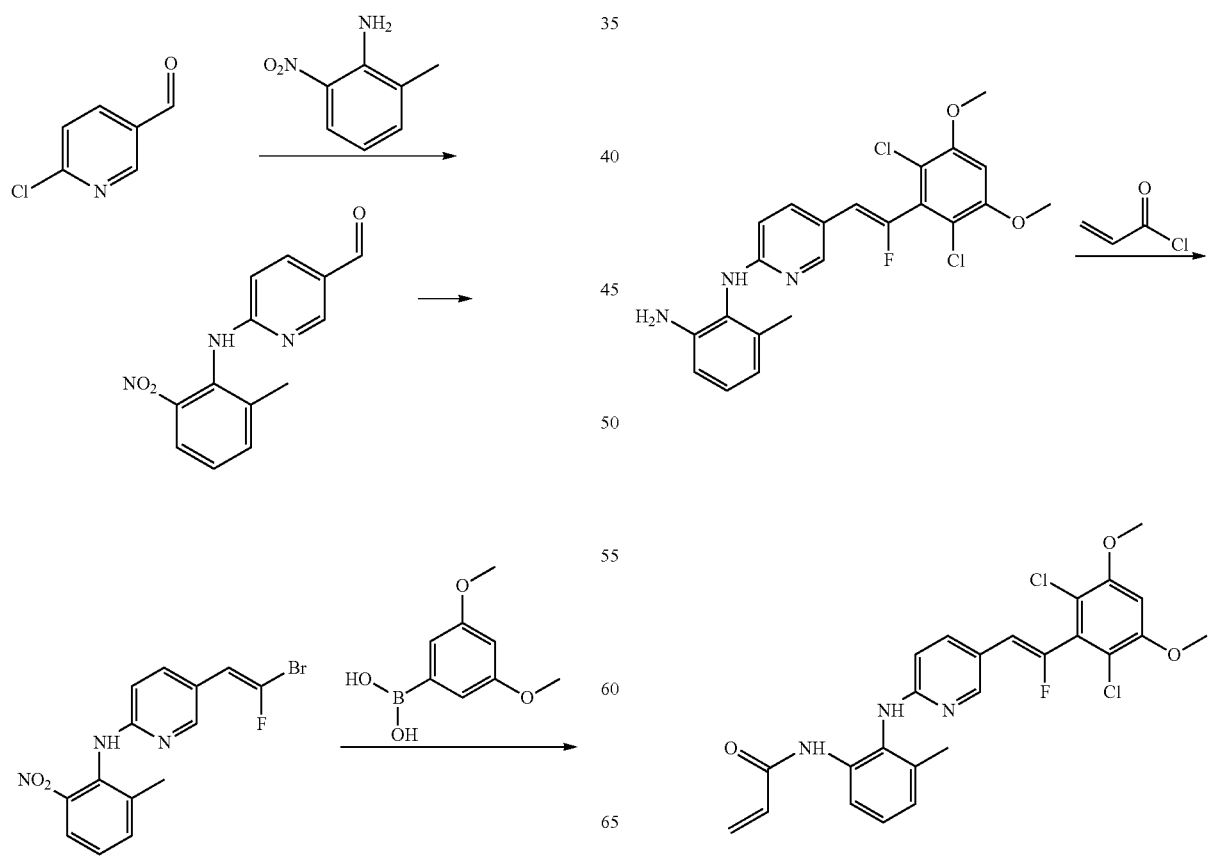
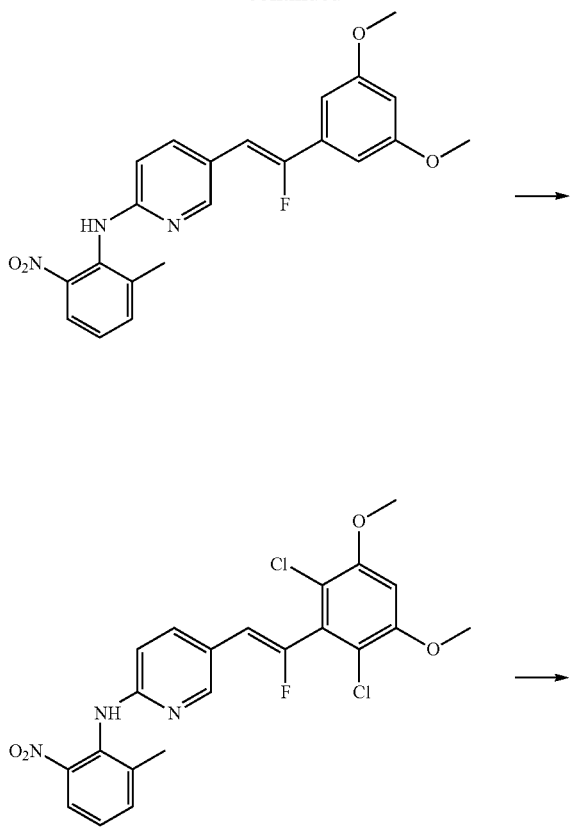

Example 7

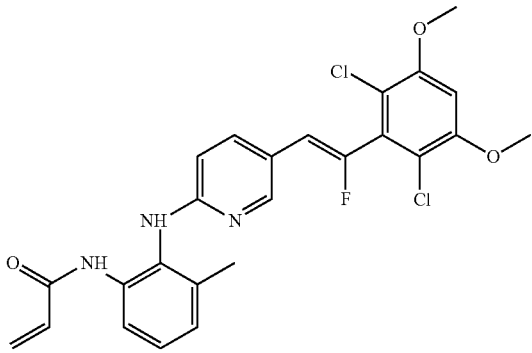 [SMILES: C=CC(=O)Nc1cccc(C)c1Nc1ccc(/C=C(\F)c2c(Cl)c(OC)cc(OC)c2Cl)cn1]

Example 7A

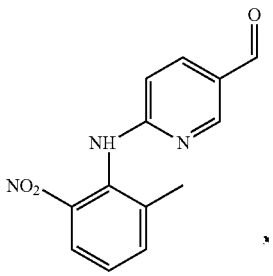 [SMILES: Cc1cccc([N+](=O)[O-])c1Nc1ccc(C=O)cn1]

A mixed solution of 2-chloro-5-pyridine carboxaldehyde (4.50 g, 31.8 mmol), 2-methyl-6-nitro-aniline (4.84 g, 31.8 mmol), Pd$_2$(dba)$_3$ (2.91 g, 3.18 mmol), Xphos (3.03 g, 6.36 mmol) and cesium carbonate (20.7 g, 63.6 mmol) in N,N-dimethylformamide (90 ml) was replaced with nitrogen for 3 times, and the mixture was stirred at 110° C. for 2 hours under the atmosphere of nitrogen. After cooled to room temperature, the reaction was diluted with water (200 ml), and then extracted with ethyl acetate (50 ml×3). The organic layers were combined and washed with water (50 ml×3), saturated saline (50 ml) successively, dried over anhydrous sodium sulfate, and filtered. The filtrate was concentrated at reduced pressure, the residue of which was purified over a flash silica gel column (the proportion of petroleum ether/ethyl acetate: 3/1) to give the compound Example 7A (4.00 g, yield: 48.9%) as a yellow oil.

LCMS (ESI) m/z: 257.9 [M+1]$^+$

Example 7B

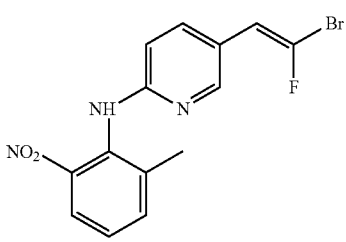 [SMILES: Cc1cccc([N+](=O)[O-])c1Nc1ccc(/C=C(\F)Br)cn1]

At 20° C., to a solution of Example 7A (4.00 g, 15.6 mmol) in ethanol (30 ml) was added hydrazine hydrate (2.34 g, 46.6 mmol), the reaction was stirred at 20° C. for 2 hours. TLC detection showed that the raw materials have been converted completely. Then ethylenediamine (2.80 g, 46.65 mmol) and cuprous chloride (154 mg, 1.55 mmol) were added to the reaction solution, and the resultant mixture was stirred at 20° C. for 30 minutes. The reaction solution was cooled to 0° C. in an ice bath, into which was then dropwise added tribromofluoromethane (10.52 g, 38.9 mmol), and the mixture was stirred at 20° C. for 16 hours. The reaction was diluted with water (100 ml), and then extracted with ethyl acetate (50 ml×3). The organic layers were combined and washed with saturated saline (50 ml), dried over anhydrous sodium sulfate, and filtered. The filtrate was concentrated at reduced pressure, the residue of which was purified over a flash silica gel column (the proportion of petroleum ether/ethyl acetate: 10/1) to give the compound Example 7B (1.56 g, yield: 28.5%) as a yellow solid.

LCMS (ESI) m/z: 352.0, 354.0 [M+1]$^+$ $^1$H NMR (400 MHz, CHLOROFORM-d) δ 8.11 (d, J=2.4 Hz, 1H), 7.98-8.08 (m, 1H), 7.90 (d, J=8.0 Hz, 2H), 7.66 (dd, J=2.4, 8.8 Hz, 1H), 7.51 (d, J=7.2 Hz, 2H), 7.22 (dd, J=8.0, 8.0 Hz, 2H), 6.49-6.58 (m, 2H), 5.86 (d, J=33.2 Hz, 1H), 2.23 (s, 3H).

Example 7C

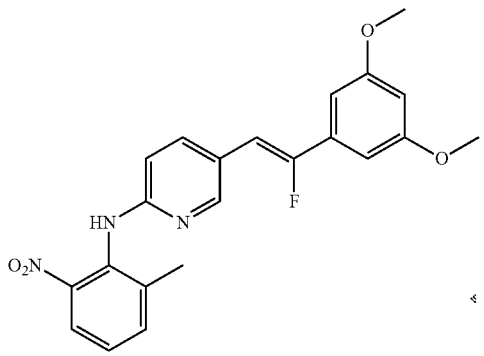 [SMILES: COc1cc(OC)cc(/C(F)=C/c2ccc(Nc3c(C)cccc3[N+](=O)[O-])nc2)c1]

A mixed solution of Example 7B (1.56 g, 4.43 mmol), 3,5-dimethoxyphenylboronic acid (802 mg, 4.43 mmol), Pd$_2$(dba)$_3$ (406 mg, 443 µmol), Sphos (3641 mg, 886 µmol) and potassium phosphate (2.35 g, 11.1 mmol) in acetonitrile (3.0 ml)/water (1.0 ml) was replaced with nitrogen for 3 times, and the mixture was stirred at 90° C. for 3 hours under the atmosphere of nitrogen. The reaction was diluted with water (30 ml), and extracted with ethyl acetate (30 ml×3). The organic layers were combined and washed with saturated saline (30 ml), dried over anhydrous sodium sulfate, and filtered. The filtrate was concentrated at reduced pressure, the residue of which was purified over a flash silica gel column (the proportion of petroleum ether/ethyl acetate: 3/1) to give the compound Example 7C (1.4 g, yield: 67.2%) as a brown oil.

LCMS (ESI) m/z: 410.1 [M+1]$^+$

Example 7D

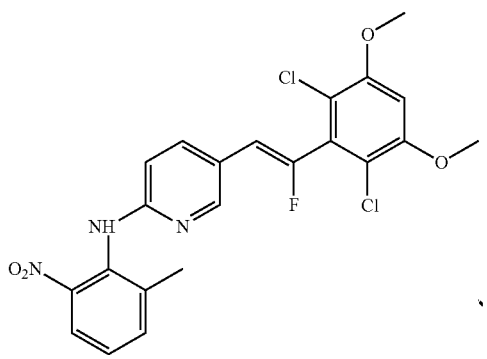 [SMILES: COc1cc(OC)c(Cl)c(/C(F)=C/c2ccc(Nc3c(C)cccc3[N+](=O)[O-])nc2)c1Cl]

At −78° C., to a solution of Example 7C (700 mg, 1.71 mmol) in tetrahydrofuran (7.0 ml) was dropwise added sulfonyl chloride (577 mg, 4.28 mmol), and the mixture was stirred at −78° C. for 1 hour. The reaction was quenched with 20 ml water at −20° C., extracted with ethyl acetate (30 ml×3), the organic layers were combined, and then washed with saturated saline (30 ml), dried over anhydrous sodium sulfate, filtered, and concentrated in vacuum, the residue of which has not been further purified to give a crude Example 7D (750 mg, crude) as a yellow oil.

LCMS (ESI) m/z: 478.2, 480.2 [M+1]$^+$

Example 7E

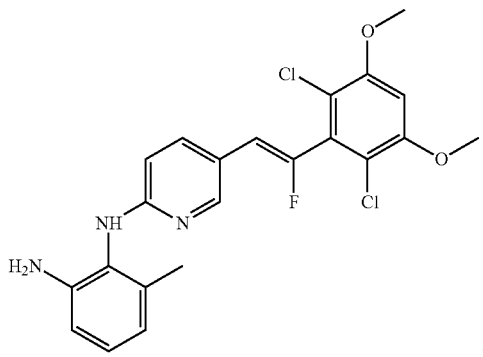

To a solution of Example 7D (750 mg, 1.57 mmol) in ethyl acetate (10 ml) was added stannous chloride dihydrate (1.77 g, 7.85 μmol), and the mixture was stirred at 80° C. for 1 hour. The reaction solution was adjusted to pH 8 with saturated sodium bicarbonate, and extracted with ethyl acetate (50 ml×3). The organic layers were combined, and then washed with saturated saline (100 ml×2), dried over anhydrous sodium sulfate, filtered, and concentrated in vacuum, the residue of which has not been further purified to give a crude Example 7E (500 mg, crude) as a yellow solid.

LCMS (ESI) m/z: 448.1, 450.1 [M+1]$^+$

Example 7

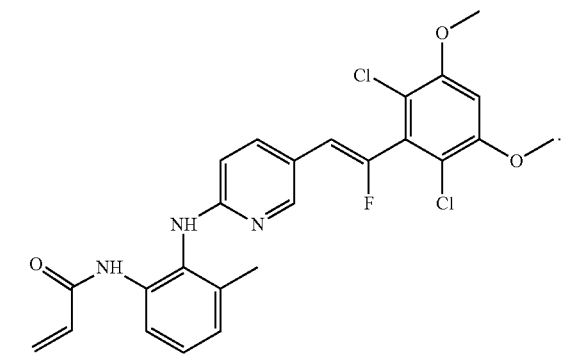 [SMILES: C=CC(=O)Nc1cccc(C)c1Nc1ccc(/C=C(\F)c2c(Cl)c(OC)cc(OC)c2Cl)cn1]

At 0° C., to a solution of Example 7E (500 mg, 1.12 mmol) in dichloromethane (5.0 ml) were added N,N-diisopropyl ethyl amine (362 mg, 2.80 mmol) and acryloyl chloride (101 mg, 1.12 mmol) successively. The reaction was stirred at 0° C. for 2 hours, quenched with 20 ml water, extracted with dichloromethane (20 ml×3). The organic layers were combined, and then washed with saturated saline (20 ml), dried over anhydrous sodium sulfate, filtered, and concentrated in vacuum, the residue of which was purified by preparative HPLC (TFA condition), and then purified by preparative thin layer chromatography (petroleum ether/ethyl acetate=1/1) to give the title compound Example 7 (24 mg, yield: 3.97%).

LCMS (ESI) m/z: 502.0, 504.0 [M+1]$^+$ $^1$H NMR (400 MHz, CHLOROFORM-d) δ 8.16-8.33 (m, 3H), 7.83 (dd, J=8.8, 2.0 Hz, 1H), 7.23-7.29 (m, 1H), 7.06 (d, J=7.6 Hz, 1H), 6.60-6.65 (m, 1H), 6.28-6.37 (m, 2H), 6.10-6.24 (m, 2H), 5.64-5.81 (m, 2H), 3.94 (s, 6H), 2.21 (s, 3H).

The following examples were prepared according to the process as described in Example 7.

| Example | Structure | NMR Data | LCMS (ESI) m/z: (M + 1) |
|---|---|---|---|
| Example 22 | 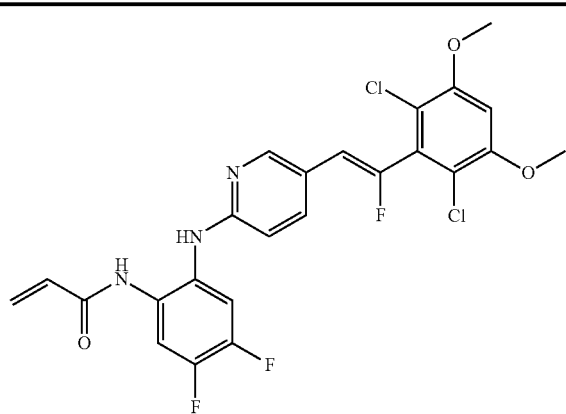 | 1H NMR (400 MHz, CHLOROFORM-d) δ 9.99-10.45 (m, 1H), 8.48 (br s, 1H), 8.14-8.27 (m, 2H), 8.07 (dd, J = 1.88, 9.41 Hz, 1H), 7.13-7.21 (m, 1H), 6.91 (d, J = 9.04 Hz, 1H), 6.66 (s, 1H), 6.39-6.48 (m, 1H), 6.22-6.34 (m, 1H), 5.69-5.83 (m, 2H), 3.96 (s, 6H) | 524.1 |

-continued

| Example | Structure | NMR Data | LCMS (ESI) m/z: (M + 1) |
|---|---|---|---|
| Example 23 | 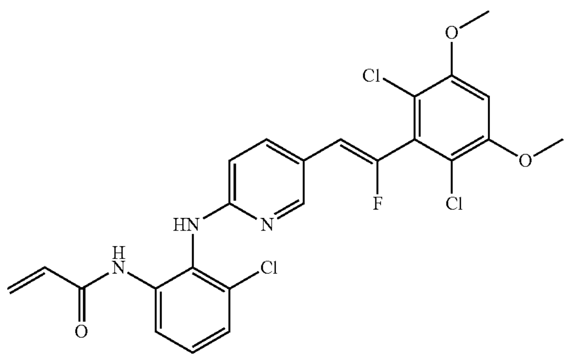 [SMILES: C=CC(=O)Nc1cccc(Cl)c1Nc1ccc(/C=C(\F)c2c(Cl)c(OC)cc(OC)c2Cl)cn1] | 1H NMR (400 MHz, CHLOROFORM-d) δ 8.82 (br s, 1H), 8.34 (s, 1H), 8.26 (br s, 1H), 7.94 (dd, J = 1.76, 8.54 Hz, 1H), 7.26-7.30 (m, 1H), 6.65 (s, 1H), 6.44-6.55 (m, 2H), 6.29-6.39 (m, 1H), 6.10-6.23 (m, 1H), 5.67-5.87 (m, 2H), 3.96 (s, 6H) | 524.1 |
| Example 28 | 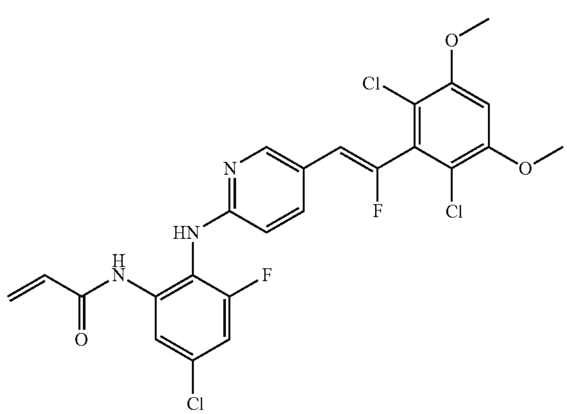 [SMILES: C=CC(=O)Nc1cc(Cl)cc(F)c1Nc1ccc(/C=C(\F)c2c(Cl)c(OC)cc(OC)c2Cl)cn1] | 1H NMR (400 MHz, DMSO-d6) δ 9.73 (s, 1H), 8.40 (s, 1H), 8.15 (d, J = 2.02 Hz, 1H), 7.98 (s, 1H), 7.86 (dd, J = 2.26, 8.78 Hz, 1H), 7.28 (dd, J = 2.52, 9.80 Hz, 1H), 7.05 (s, 1H), 6.71 (d, J = 8.78 Hz, 1H), 6.58 (dd, J = 10.16, 16.94 Hz, 1H), 6.26 (dd, J = 1.88, 16.94 Hz, 1H), 5.91-6.08 (m, 1H), 5.70-5.82 (m, 1H), 3.96 (s, 6H) | 540.1 |
| Example 35 | 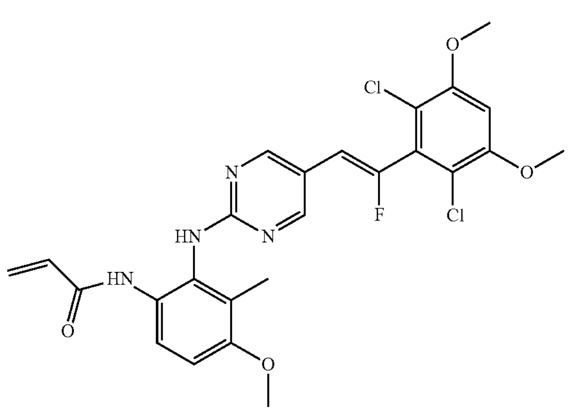 [SMILES: C=CC(=O)Nc1ccc(OC)c(C)c1Nc1ncc(/C=C(\F)c2c(Cl)c(OC)cc(OC)c2Cl)cn1] | $^1$H NMR (400 MHz, CHLOROFORM-d) δ 8.68 (br s, 2H), 8.10-8.37 (m, 2H), 7.71-7.89 (m, 1H), 7.82 (br s, 1H), 6.89 (br s, 1H), 6.65 (s, 1H), 6.35 (br s, 2H), 5.62-5.82 (m, 2H), 3.95 (s, 6H), 3.85 (s, 3H), 2.13 (br s, 3H) | 533.3 |

| Example | Structure | NMR Data | LCMS (ESI) m/z: (M + 1) |
|---|---|---|---|
| Example 29 | 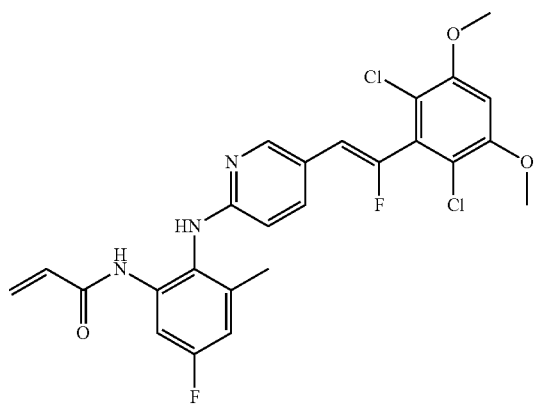 [SMILES: C=CC(=O)Nc1cc(F)cc(C)c1Nc1ccc(/C=C(\F)c2c(Cl)c(OC)cc(OC)c2Cl)cn1] | $^1$H NMR (400 MHz, METHANOL-d4) δ 8.25 (dd, J = 2.1, 9.3 Hz, 1H), 8.12 (d, J = 7.3 Hz, 1H), 8.07 (s, 1H), 7.27 (d, J = 11.5 Hz, 1H), 7.12 (d, J = 9.4 Hz, 1H), 6.95 (s, H), 6.60-6.50 (m, 1H), 6.43-6.35 (m, 1H), 5.98 (d, J = 9.4 Hz, 1H), 5.83-5.80 (m, 1H), 3.97 (s, 6H), 2.28 (s, 3H). | 520.1 |
| Example 24 | 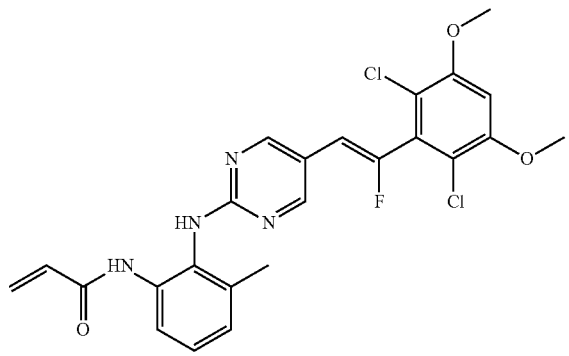 [SMILES: C=CC(=O)Nc1cccc(C)c1Nc1ncc(/C=C(\F)c2c(Cl)c(OC)cc(OC)c2Cl)cn1] | $^1$H NMR (400 MHz, CHLOROFORM-d) δ 8.64 (s, 2H), 7.92-8.16 (m, 2H), 7.28 (s, 1H), 7.10 (br d, J = 7.28 Hz, 1H), 6.99-7.07 (m, 1H), 6.65 (s, 1H), 6.30-6.42 (m, 1H), 6.13-6.23 (m, 1H), 5.63-5.77 (m, 2H), 3.95 (s, 6H), 2.27 (s, 3H) | 503.2 |
| Example 30 | 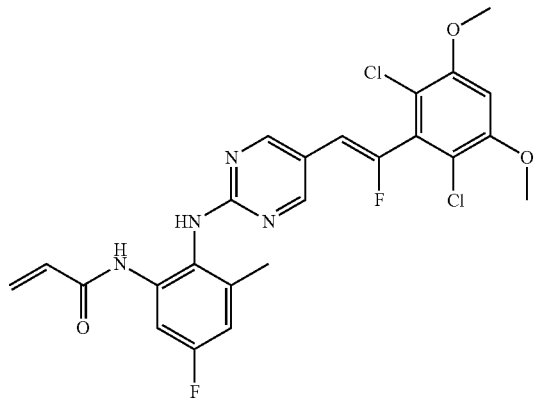 [SMILES: C=CC(=O)Nc1cc(F)cc(C)c1Nc1ncc(/C=C(\F)c2c(Cl)c(OC)cc(OC)c2Cl)cn1] | 1H NMR (400 MHz, METHANOL-d4) δ 8.59 (s, 2H), 8.17 (d, J = 7.5 Hz, 1H), 7.10 (d, J = 11.3 Hz, 1H), 6.94 (s, 1H), 6.60-6.48 (m, 1H), 6.41-6.30 (m, 1H), 5.85 (br d, 1H), 5.78 (dd, J = 1.4, 8.7 Hz, 1H), 3.97 (s, 6H), 2.26 (s, 3H) | 521.0 |
| Example 31 | 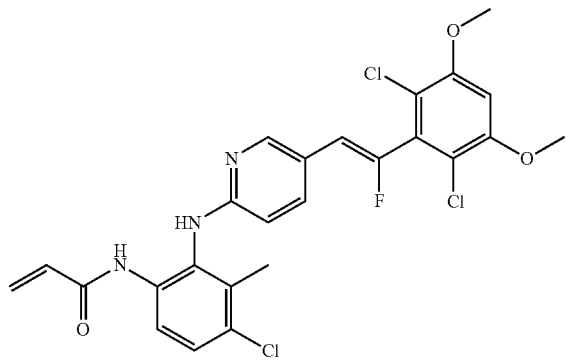 [SMILES: C=CC(=O)Nc1ccc(Cl)c(C)c1Nc1ccc(/C=C(\F)c2c(Cl)c(OC)cc(OC)c2Cl)cn1] | 1H NMR (400 MHz, CHLOROFORM-d) δ 11.14 (br s, 1H), 8.71 (br s, 1H), 8.18 (br s, 1H), 7.99 (br dd, J = 8.54, 18.32 Hz, 2H), 7.37 (br d, J = 8.04 Hz, 1H), 6.65 (br s, 1H), 6.17-6.49 (m, 3H), 5.59-5.86 (m, 2H), 3.94 (s, 6H), 2.22 (br s, 3H) | 538.0 |

-continued
| Example | Structure | NMR Data | LCMS (ESI) m/z: (M + 1) |
|---|---|---|---|
| Example 18 | 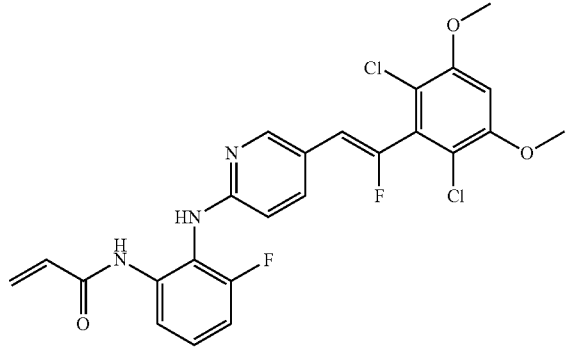 [SMILES: C=CC(=O)Nc1cccc(F)c1Nc1ccc(/C=C(\F)c2c(Cl)c(OC)cc(OC)c2Cl)cn1] | ¹H NMR 400 MHz, CHLOROFORM-d) δ 11.51 (s, 1H), 8.69 (s, 1H), 8.19 (s, 1H), 7.99-8.14 (m, 2H), 7.29-7.41 (m, 1H), 7.01 (t, J = 9.04 Hz, 1H), 6.73 (dd, J = 4.02, 9.29 Hz, 1H), 6.66 (s, 1H), 6.30-6.49 (m, 2H), 5.65-5.83 (m, 2H), 3.86-4.04 (m, 6H) | 506.2 |
Scheme G
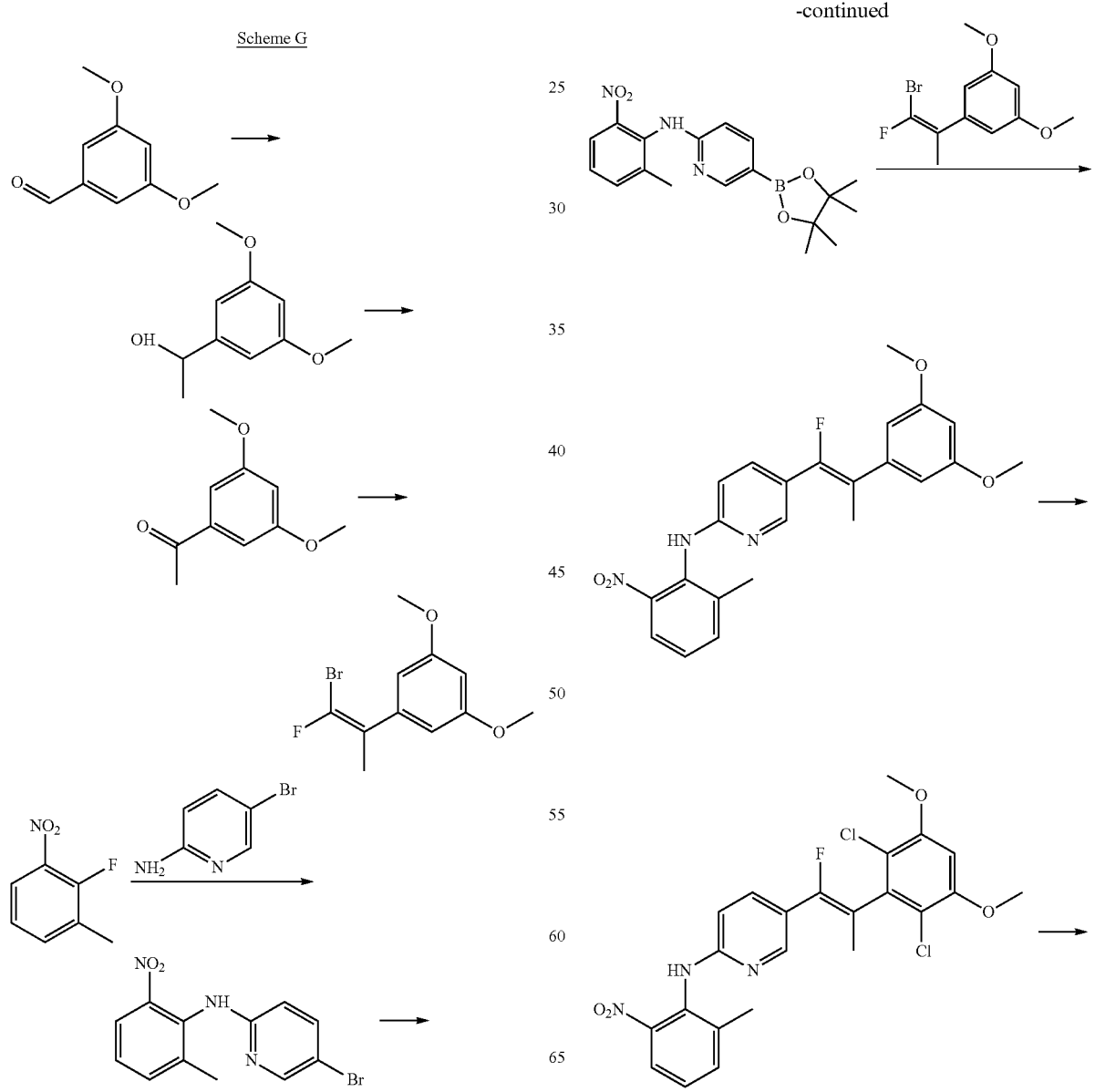

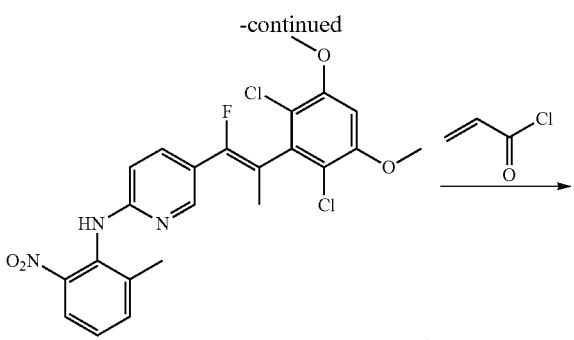

Example 10

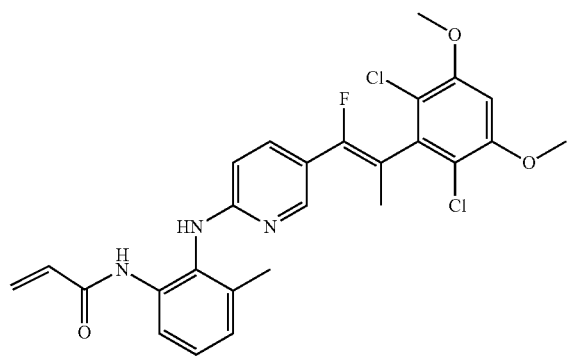 [SMILES: C=CC(=O)Nc1cccc(C)c1Nc1ccc(/C(F)=C(\C)c2c(Cl)c(OC)cc(OC)c2Cl)cn1]

Example 10A

Under the atmosphere of nitrogen, a solution of 3,5-dimethoxy-benzaldehyde (5.00 g, 30.1 mmol) in tetrahydrofuran (75 ml) was placed in a 250 ml three-neck flask, the solution was cooled to −10° C. in a dry ice salt bath, into which was dropwise added a solution of MeMgBr (3.0 M, 15.0 ml) in diethyl ether slowly, during the process of addition the temperature of the reaction solution was kept no more than 0° C. Upon the completion of the dropwise addition, the reaction was stirred at 0° C. for 1 hour, when the raw materials have been showed to be reacted completely based on LCMS detection, the mixture was stirred for 1 hour, a saturated solution of ammonium chloride was then added to the reaction solution, and then the resultant mixture was extracted with ethyl acetate (2×30 ml). The organic phases were combined and extracted with saturated saline (30 ml), dried over anhydrous sodium sulfate, and filtered. The filtrate was concentrated at reduced pressure to give the compound Example 10A as a light pink solid (5.48 g, yield: 63.6%). The compound was used directly in the next step without being purified.

LCMS (ESI) m/z: 164.9 [M−17]$^+$ $^1$H NMR (400 MHz, CHLOROFORM-d) δ 6.54 (d, J=2.0 Hz, 2H), 6.40-6.35 (m, 1H), 4.84 (q, J=6.4 Hz, 1H), 3.83-3.76 (m, 6H), 1.48 (d, J=6.4 Hz, 3H)

Example 10B

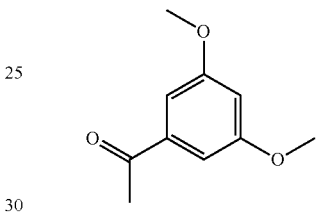

At room temperature (20° C.), active manganese dioxide (41.8 g, 481 mmol) was added into a solution of Example 9A (5.48 g, 30.1 mmol) in tetrahydrofuran (100 ml). The reaction was heated to reflux for 2 hours in an oil bath. Through TLC and LCMS detection, the reaction of Example 9A is complete and the product has generated, the mixture was filtered, and the solid was washed with tetrahydrofuran (2×30 ml). The filtrate was combined and concentrated at reduced pressure to give a crude product, which was purified over a flash silica gel column (petroleum ether:ethyl acetate=30:1-15:1) to give the Example 10B (4.55 g, yield: 84.0%) as a light yellow oil.

LCMS (ESI) m/z: 181.0 [M+1]$^+$ $^1$H NMR (400 MHz, CHLOROFORM-d) δ 7.09 (d, J=2.4 Hz, 2H), 6.65 (t, J=2.4 Hz, 1H), 3.84 (s, 6H), 2.58 (s, 3H).

Example 10C

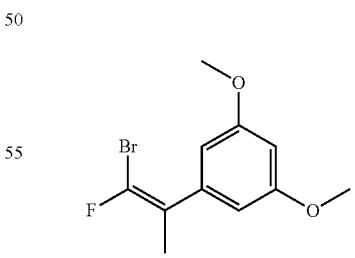

At room temperature (25° C.), hydrazine hydrate (4.17 g, 83.2 mmol, 4.05 ml) was dropwise added into a solution of Example 10B (5.00 g, 27.8 mmol) in ethanol (50 ml). At 28° C., the reaction was stirred for 16 hours, when TLC detection showed that 3,5-dimethoxy acetophenone has been reacted completely, ethylenediamine (5.51 g, 83.2 mmol) and cuprous chloride (275 mg, 2.78 mmol) were added into the reaction flask. After 30 minutes, the mixture was cooled to 0° C. in an ice bath, then a solution of tribromofluoromethane (18.8 g, 69.4 mmol) in ethanol (50 ml) was dropwise added into the reaction solution through a constant pressure dropping funnel (with a little gas being released during the dropwise addition). Upon the completion of the dropwise addition, the reaction was stirred at 0° C. for 1 hour, warmed to 25° C. and then reacted for another 72 hours. When the intermediate has been completely reacted, the reaction was filtered, the solid was washed with ethyl acetate, and the filtrate was concentrated at reduced pressure to evaporate off most of the solvents, then diluted with ethyl acetate (200 ml), and washed with an aqueous solution of citric acid (1 M, 50 ml), partitioned, and the aqueous phase was then extracted with ethyl acetate (3×100 ml). The organic phases were combined and washed with saturated saline (150 ml), dried over anhydrous sodium sulfate, and filtered. The filtrate was concentrated at reduced pressure to give a crude product, which was purified over a flash silica gel column (mobile phase: 0-30% ethyl acetate/petroleum ether) to give the Example 10C (1.27 g, yield: 16.6%) as a light yellow oil.

LCMS (ESI) m/z: 275.0, 277.0 [M+1]$^+$ $^1$H NMR (400 MHz, CHLOROFORM-d) δ 6.51 (s, 1H), 6.46-6.41 (m, 1H), 3.82 (s, 6H), 2.10-2.06 (m, 3H)

Example 10D

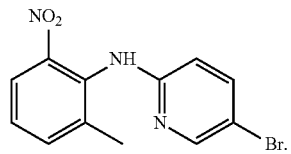 [SMILES: Cc1cccc([N+](=O)[O-])c1Nc1ccc(Br)cn1]

Under the atmosphere of nitrogen, a solution of 5-bromo-2-amino-aniline (10.0 g, 57.8 mmol) in tetrahydrofuran (200 ml) was placed in a 500 ml three-neck flask, the solution was cooled to 0° C. in a dry ice bath. Sodium hydrogen (3.47 g, 86.7 mmol, purity: 60%) was added into the reaction solution batchwise. After stirring for half an hour, a solution of 2-fluoro-3-methylnitroaniline (13.5 g, 86.7 mmol) in tetrahydrofuran (5.0 ml) was dropwise added into the reaction solution slowly. Upon the completion of the dropwise addition, the reaction was warmed to 25° C. and stirred for 16 hours. When LCMS detection showed that most of the raw materials have been reacted completely, water (40 ml) was added into the reaction solution to quench the reaction, and then the mixture was extracted with ethyl acetate (2×50 ml). The organic phases were combined and extracted with saturated saline (100 ml), dried over anhydrous sodium sulfate, and filtered. The filtrate was concentrated at reduced pressure to give a crude product, which was purified over a flash silica gel column (mobile phase: 0-15% ethyl acetate/petroleum ether) to give the Example 10D (10.0 g, yield: 56.3%) as a yellow solid.

LCMS (ESI) m/z: 307.8, 309.8 [M+1]$^+$ $^1$H NMR (400 MHz, CHLOROFORM-d) δ 8.21 (d, J=2.4 Hz, 1H), 7.98 (br. s., 1H), 7.92 (d, J=8.0 Hz, 1H), 7.60 (dd, J=8.8, 2.4 Hz, 1H), 7.52 (d, J=7.6 Hz, 1H), 7.23 (t, J=8.0 Hz, 1H), 6.48 (d, J=8.4 Hz, 1H), 2.27-2.20 (m, 3H).

Example 10E

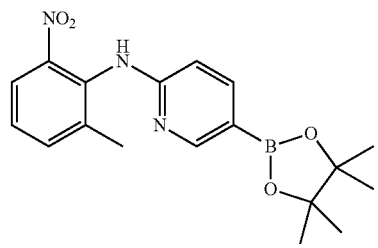 [SMILES: Cc1cccc([N+](=O)[O-])c1Nc1ccc(B2OC(C)(C)C(C)(C)O2)cn1]

Example 10D (1.00 g, 3.25 mmol), bis(pinacolato)diboron (990 mg, 3.90 mmol), Pd(dppf)Cl$_2$ (265 mg, 325 μmol) and potassium acetate (638 mg, 6.50 mmol) were placed in a 50 ml round-bottom flask, and dioxane (10.0 ml) was added respectively. After replacement with nitrogen for three times, the reaction solution was heated to 90° C. in an oil bath and reacted for 16 hours (nitrogen protection). TLC (petroleum ether:ethyl acetate=5:1) detection showed that the reactants have disappeared. The reaction was cooled to room temperature, and diluted with ethyl acetate (30 ml). The reaction was filtered, the filtrate was concentrated at reduced pressure to give a crude product, which was purified over a flash silica gel column (mobile phase: 0-30% ethyl acetate/petroleum ether) to give the compound Example 10E (1.52 g, yield: 92.2%, purity: 70%) as a yellow solid.

Example 10F

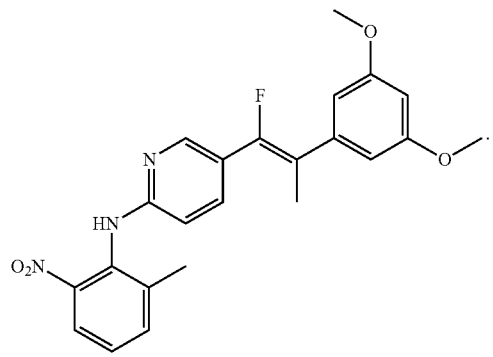 [SMILES: COc1cc(OC)cc(/C(C)=C(\F)c2ccc(Nc3c(C)cccc3[N+](=O)[O-])nc2)c1]

To a mixed solution of the compound Example 10C (580 mg, 2.11 mmol) and Example 10E (899 mg, 2.53 mmol) in dioxane solution (6.0 ml) and water (1.8 ml) were added Pd(dppf)Cl$_2$ (71 mg, 106 μmol) and potassium carbonate (583 mg, 4.22 μmol). Under the atmosphere of nitrogen, the mixture was reacted at 100° C. for 16 hours. TLC and LCMS detection showed that the reaction has been completed. After the reaction was cooled, the mixture was diluted with water (20 ml) and ethyl acetate (20 ml), partitioned, the aqueous phase was extracted with ethyl acetate (3×10 ml) for 3 times. The organic phases were combined and dried over anhydrous sodium sulfate, and filtered. The filtrate was concentrated at reduced pressure to give an oily residue, which was purified over a flash silica gel column (petroleum ether:ethyl acetate=7:3) to give the compound 10F (262 mg, yield: 29.3%) as a yellow solid.

$^1$H NMR (400 MHz, CHLOROFORM-d) δ 8.36 (s, 1H), 8.07 (br. s., 1H), 7.92 (d, J=8.0 Hz, 1H), 7.68 (dd, J=8.4, 2.0

Hz, 1H), 7.54 (d, J=7.6 Hz, 1H), 7.22-7.28 (m, 1H), 6.56-6.66 (m, 3H), 6.42 (t, J=2.0 Hz, 1H), 4.13 (q, J=7.2 Hz, 1H), 3.82 (s, 6H), 2.28 (s, 3H).

Example 10G

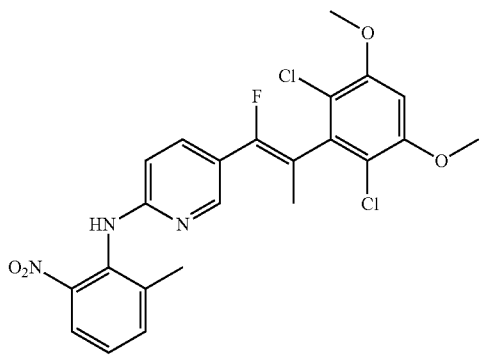 [SMILES: COc1cc(OC)c(Cl)c(/C(C)=C(\F)c2ccc(Nc3c(C)cccc3[N+](=O)[O-])nc2)c1Cl]

A solution of Example 1 OF (240 mg, 567 μmol) in anhydrous tetrahydrofuran (6.0 ml) was cooled to −20° C., into which was then dropwise added sulfonyl chloride (191 mg, 1.42 mmol) slowly. Upon the completion of the dropwise addition, the reaction solution was reacted at −20° C. for 1 h. Through TLC (petroleum ether:ethyl acetate=5:1), LCMS detection showed that the raw materials have completely converted to the product Example 26D. The reaction was quenched with water (2.0 ml), neutralized to pH=7 with a 5% aqueous solution of sodium bicarbonate, and then extracted with ethyl acetate (3×10 ml). The organic phases were combined and washed with saturated saline (10 ml), dried over anhydrous sodium sulfate, and filtered. The filtrate was concentrated at reduced pressure to give the Example 10G (280 mg) as a light yellow solid, which was directly used in the next step.

LCMS (ESI) m/z: 491.1, 493.9 [M+1]$^+$

Example 10H

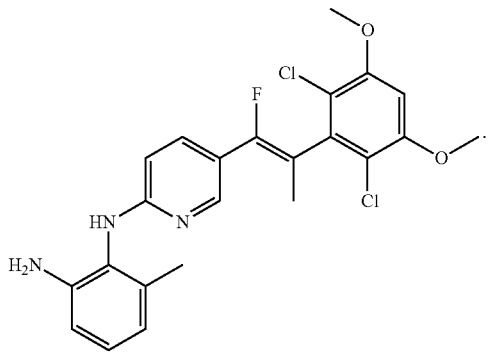 [SMILES: COc1cc(OC)c(Cl)c(/C(C)=C(\F)c2ccc(Nc3c(C)cccc3N)nc2)c1Cl]

At room temperature (20° C.), to a solution of Example 10G (260 mg, 528 μmol) in ethanol (15.0 ml) was added Raney-Ni (500 mg, 5.84 mmol) (nitrogen protection). The mixture was replaced with hydrogen for several times and then stirred at 20° C. for 4 hours (15 psi). LCMS detection showed that the reactants have disappeared. The reaction was filtered and concentrated at reduced pressure to give the compound Example 10 H (220 mg, yield: 90.1%) as a light yellow solid, which was directly used in the next step.

LCMS (ESI) m/z: 462.0, 464.0[M+1]$^+$

Example 10

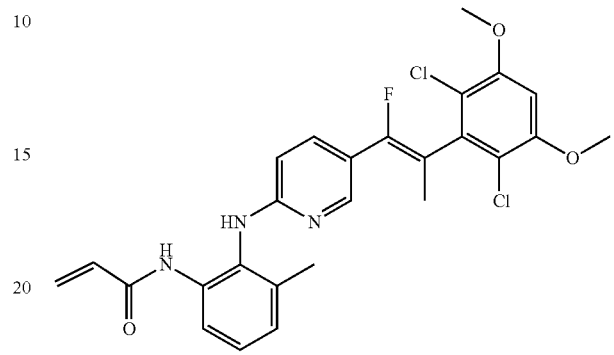

Example 10H (235 mg, 508 μmol), N,N-diisopropyl ethyl amine (131 mg, 1.02 μmol) and dichloromethane (5.0 ml) were added into a 50 ml round-bottom flask, and the solution was cooled to 0° C. in an ice-water bath. Acryloyl chloride (46 mg, 508 μmol) was dropwise added, the reaction solution was reacted at 0° C. for 30 minutes. When LCMS detection showed that the reaction has been completed, the reaction was quenched with ice-water (2 ml), diluted with 5 ml dichloromethane and extracted with dichloromethane (2×5 ml). The dichloromethane solution was combined and washed with saturated saline (5 ml), dried over anhydrous sodium sulfate, and filtered. The filtrate was concentrated at reduced pressure to give a residue. The crude product was then purified by preparative HPLC (trifluoroacetic acid system) to give the target compound Example 10 (45 mg, yield: 17.0%).

LCMS (ESI) m/z: 516.1, 518.1[M+1]$^+$ $^1$H NMR (400 MHz, CHLOROFORM-d) δ 11.18 (br. s., 1H), 8.49 (br. s., 1H), 8.15 (br. s., 1H), 7.99-7.87 (m, 2H), 7.31 (t, J=8.0 Hz, 1H), 7.13 (d, J=7.6 Hz, 1H), 6.56 (s, 2H), 6.45-6.35 (m, 1H), 6.34-6.23 (m, 1H), 5.75 (d, J=10.8 Hz, 1H), 3.94 (s, 6H), 2.23 (s, 3H), 2.04 (d, J=2.8 Hz, 3H).

Scheme H

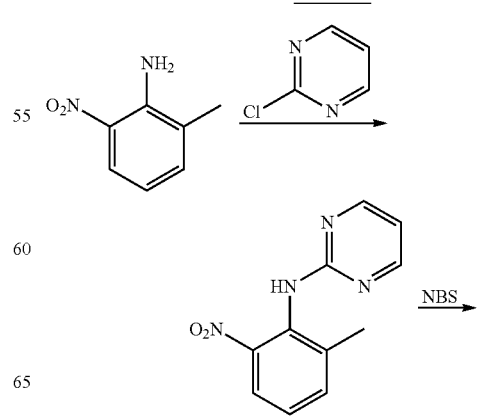

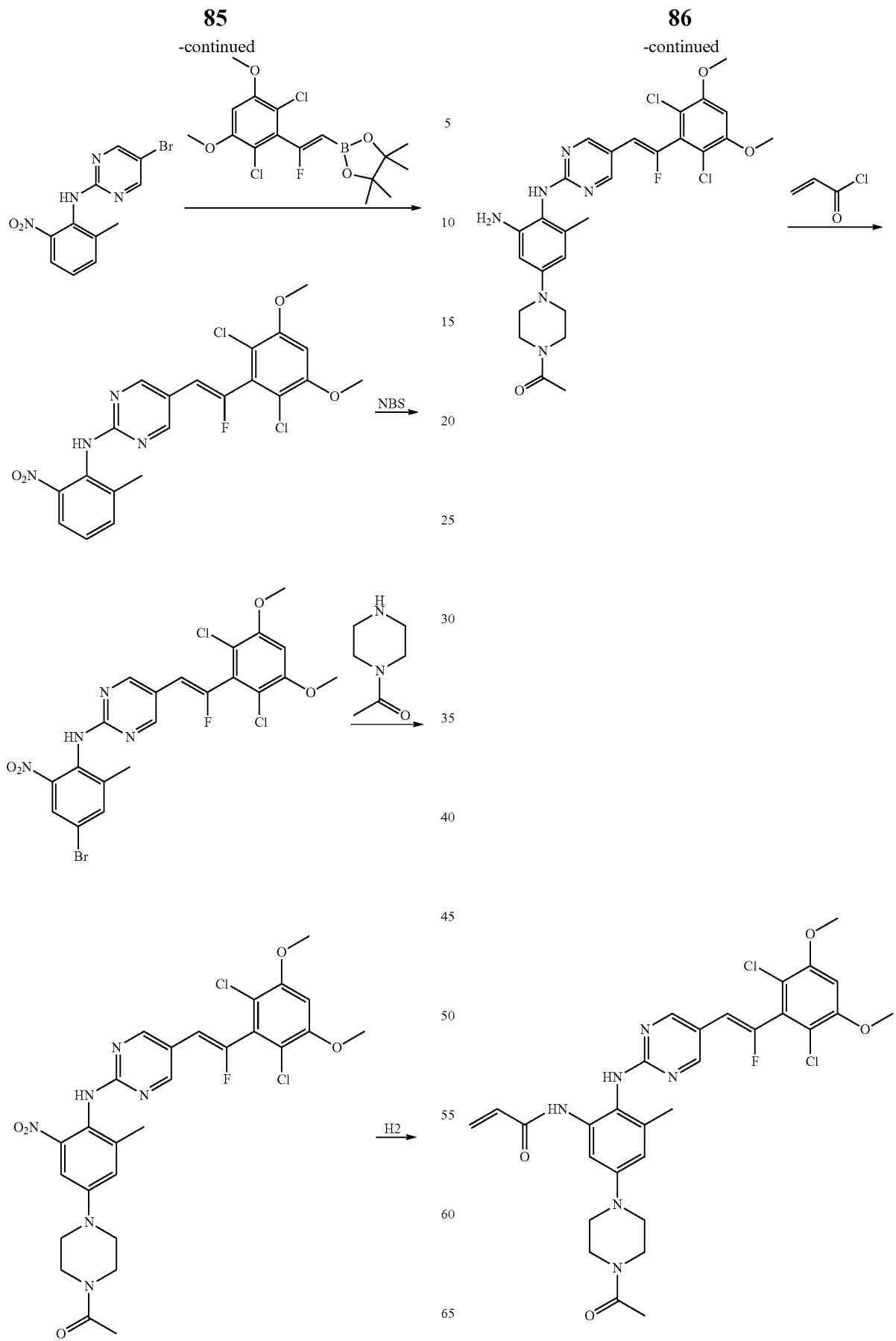

Example 26

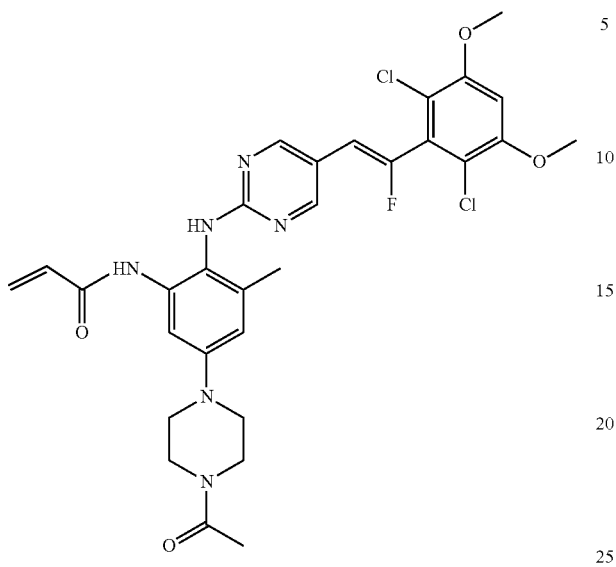

Example 26A

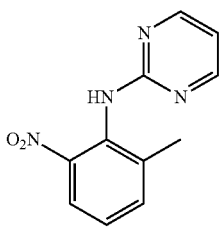 [SMILES: Cc1cccc([N+](=O)[O-])c1Nc1ncccn1]

2-Methyl-6-nitroaniline (13.28 g, 87.31 mmol), 2-chloropyrimidine (10.00 g, 87.31 mmol), Pd$_2$(dba)$_3$ (4.00 g, 4.37 mmol), XPhos (4.16 g, 8.73 mmol) and Cs$_2$CO$_3$ (56.90 g, 174.62 mmol) were added into DMA (250.00 mL), with nitrogen replacement for 3 times, and then the reaction solution was stirred at 100° C. for 3 hours under the atmosphere of nitrogen. The reaction solution was poured into 250 ml ice-water, extracted with EtOAc (200 ml×3). The organic layers were combined and then washed with water (50 ml×3) and saturated saline (50 ml), dried over anhydrous sodium sulfate, filtered, and concentrated in vacuum, the residue of which was purified over a flash silica gel column (petroleum ether/ethyl acetate: 5/1) to give the title compound Example 26A (11.00 g, 54.72% yield) as a brown solid.

LCMS (ESI) m/z: 230.9 [M+1]$^+$

Example 26B

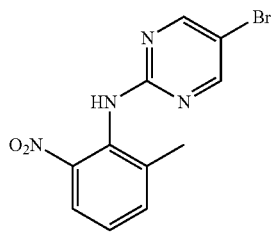 [SMILES: Cc1cccc([N+](=O)[O-])c1Nc1ncc(Br)cn1]

Example 26A (500.00 mg, 2.17 mmol), NBS (424.84 mg, 2.39 mmol) were added into chloroform (5.00 mL), and then the reaction solution was stirred at 30° C. for 16 hours. The reaction solution was directly concentrated in vacuum, the residue of which was purified over a flash silica gel column (the proportion of petroleum ether/ethyl acetate: 5/1) to give the Example 26B (540.00 mg, 80.50% yield) as a yellow solid.

LCMS (ESI) m/z: 310.8 [M+3]$^+$ $^1$H NMR (400 MHz, CHLOROFORM-d) δ 8.37 (s, 2H), 7.89 (br s, 1H), 7.83-7.88 (m, 1H), 7.54 (d, J=7.53 Hz, 1H), 7.28 (t, J=8.03 Hz, 1H), 2.32 (s, 3H).

Example 26C

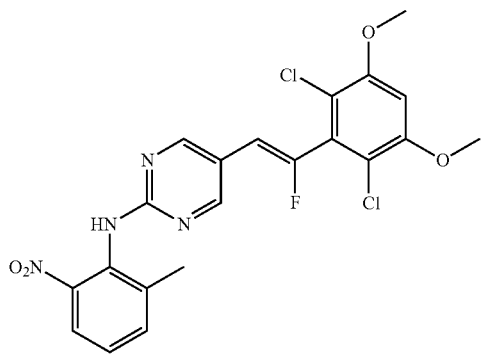 [SMILES: COc1cc(OC)c(Cl)c(/C(F)=C/c2cnc(Nc3c(C)cccc3[N+](=O)[O-])nc2)c1Cl]

Example 16D (2.00 g, 6.47 mmol), Example 26B (3.66 g, 9.71 mmol), potassium phosphate (2.75 g, 12.94 mmol), Pd(dppf)Cl$_2$ (473.41 mg, 647.00 μmol) were added into a mixed solution of dioxane (30.00 ml) and water (10.00 ml), with nitrogen replacement for 3 times, and then the reaction solution was stirred 100° C. for 16 hours under the atmosphere of nitrogen. The reaction solution was added into 50 ml ice-water, extracted with EtOAc (30 ml×3). The organic layers were combined and washed with saturated saline (20 ml), dried over anhydrous sodium sulfate, filtered, and concentrated in vacuum, the residue of which was purified over a flash silica gel column (the proportion of petroleum ether/ethyl acetate: 3/1) to give the Example 26C (2.40 g, 77.39% yield) as a yellow solid.

LCMS (ESI) m/z: 479.1 [M+1]+

$^1$H NMR (400 MHz, CHLOROFORM-d) δ 8.63 (s, 2H), 8.02 (s, 1H), 7.88 (d, J=7.53 Hz, 1H), 7.55 (d, J=7.53 Hz, 1H), 7.27-7.31 (m, 1H), 6.65 (s, 1H), 5.61-5.79 (m, 1H), 3.95 (s, 6H), 2.35-2.37 (m, 3H).

Example 26D

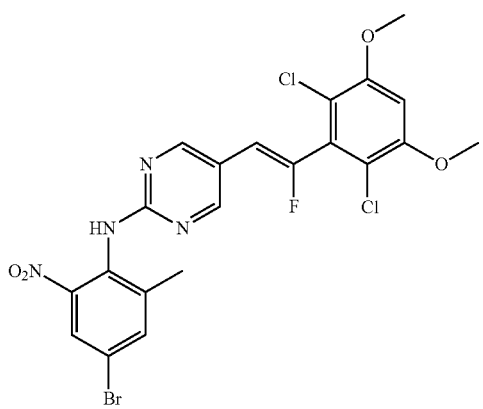 [SMILES: COc1cc(OC)c(Cl)c(/C(F)=C/c2cnc(Nc3c(C)cc(Br)cc3[N+](=O)[O-])nc2)c1Cl]

Example 26C (1.10 g, 2.30 mmol), NBS (1.23 g, 6.90 mmol) were added into acetic acid (10.00 mL), and the mixture was stirred at 60° C. for 16 hours. The reaction solution was adjusted to pH=7 with an aqueous solution of sodium carbonate, into which was added 30 ml ice-water, the mixture was extracted with EtOAc (20 ml×3). The organic layers were combined and washed with saturated saline (10 ml×2), dried over anhydrous sodium sulfate, filtered, and concentrated in vacuum, the residue of which was purified over a flash silica gel column (the proportion of petroleum ether/ethyl acetate: 3/1) to give the title compound Example 26D (370.00 mg, 28.82% yield).

LCMS (ESI) m/z: 558.9 [M+3]

Example 26E

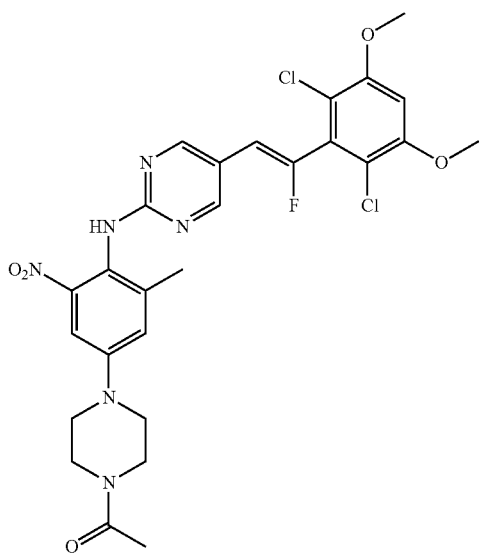 [SMILES: COc1cc(OC)c(Cl)c(/C(F)=C/c2cnc(Nc3c(C)cc(N4CCN(C(C)=O)CC4)cc3[N+](=O)[O-])nc2)c1Cl]

Example 26D (200.00 mg, 358.31 μmol), 1-acetyl-piperazine (91.85 mg, 716.62 μmol), Pd$_2$(dba)$_3$ (32.81 mg, 35.83 μmol), XPhos (34.16 mg, 71.66 μmol) and Cs$_2$CO$_3$ (233.49 mg, 716.62 μmol) were added into DMA (5.00 mL), with nitrogen replacement for 3 times, then the reaction solution was stirred 120° C. for 2 hours under the atmosphere of nitrogen. To the reaction solution was added 10 ml ice-water, the mixture was extracted with EtOAc (10 ml×3). The organic layers were combined and then washed with water (5 ml×3) and saturated saline (5 ml), dried over anhydrous sodium sulfate, filtered, and concentrated in vacuum, the residue of which was purified over a flash silica gel column (the proportion of petroleum ether/ethyl acetate: 1/1) to give the title compound Example 26 E (70.00 mg, 32.27% yield) as an off-white solid.

LCMS (ESI) m/z: 605.1 [M+1]

Example 26F

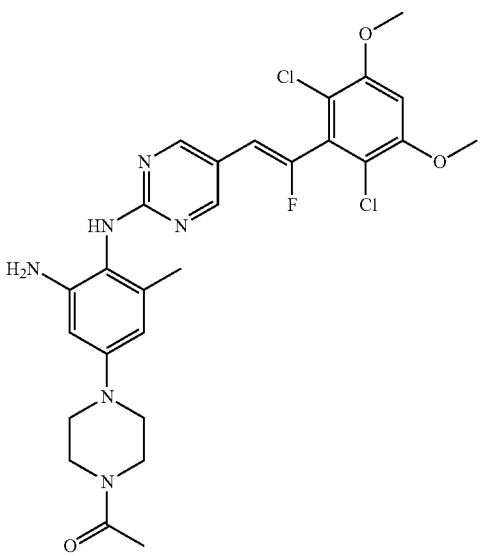

To a solution of Example 26E (80.00 mg, 132.13 μmol) in ethanol (1.00 ml) was added Raney-Ni (11.32 mg, 132.13 μmol), with hydrogen replacement for 3 times, then the mixture was stirred at 30° C. for 0.5 hours under the condition of hydrogen (15 psi). The reaction solution was filtered, and concentrated in vacuum, the residue of which was not further purified to give a solid crude product Example 26F (68.00 mg, crude).

LCMS (ESI) m/z: 575.0 [M+1]

Example 26

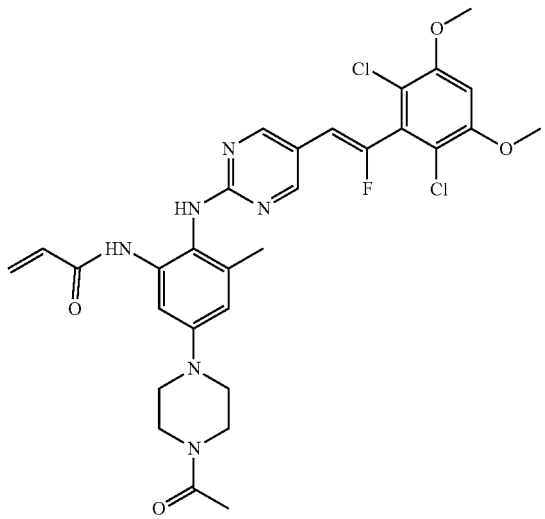 [SMILES: C=CC(=O)Nc1cc(N2CCN(C(C)=O)CC2)cc(C)c1Nc1ncc(/C=C(\F)c2c(Cl)c(OC)cc(OC)c2Cl)cn1]

To a solution of Example 26F (68.00 mg, 118.17 μmol) in dichloromethane (2 ml) were added DIEA (30.54 mg, 236.33 μmol) and acryloyl chloride (10.70 mg, 118.17 μmol) at 0° C., and the mixture was stirred at 0° C. for 20 minutes. The reaction was quenched with 10 ml water, and extracted with dichloromethane (10 ml×3). The organic layers were combined, and then washed with saturated saline (5 ml×2), dried over anhydrous sodium sulfate, filtered, and concentrated in vacuum, the residue of which was purified by preparative HPLC (basic) to give the title compound Example 26 (18 mg, 24.20% yield).

LCMS (ESI) m/z: 629.3 [M+1]

$^1$H NMR (400 MHz, CHLOROFORM-d) δ 8.63 (s, 2H), 8.04 (br s, 1H), 7.84 (br s, 1H), 6.65 (s, 1H), 6.62 (d, J=2.51 Hz, 1H), 6.47 (s, 1H), 6.38 (d, J=1.25 Hz, 1H), 6.12-6.21 (m, 1H), 5.72-5.75 (m, 1H), 5.64-5.71 (m, 1H), 3.95 (s, 6H), 3.72-3.78 (m, 2H), 3.57-3.63 (m, 2H), 3.23 (td, J=5.11, 15.87 Hz, 4H), 2.20 (s, 3H), 2.14 (s, 3H)

The following examples were prepared according to the process as described in Example 26.

| Example | Structure | NMR Data | LCMS (ESI) m/z: (M + 1) |
|---|---|---|---|
| Example 11 | 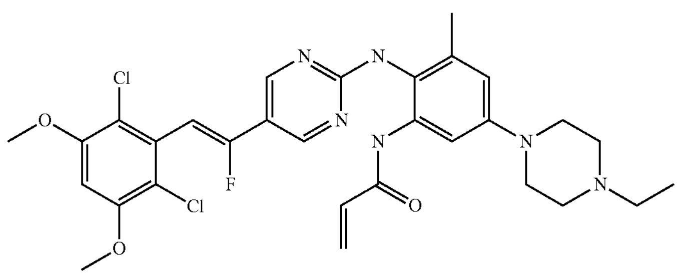 [SMILES: C=CC(=O)Nc1cc(N2CCN(CC)CC2)cc(C)c1Nc1ncc(/C(F)=C/c2c(Cl)c(OC)cc(OC)c2Cl)cn1] | $^1$H NMR (400 MHz, CHLOROFORM-d) δ13.48 (br s, 1H), 8.67 (s, 2H), 7.99 (br s, 1H), 7.80 (br s, 1H), 6.71 (s, 1H), 6.65-6.56 (m, 2H), 6.38 (d, J = 16.8 Hz, 1H), 6.28-6.13 (m, 2H), 5.75 (d, J = 10.4 Hz, 1H), 3.95 (s, 6H), 3.83-3.63 (m, 4H), 3.40 (br s, 2H), 3.15 (q, J = 7.2 Hz, 2H), 2.92 (br s, 2H), 2.21 (s, 3H), 1.41 (t, J = 7.2 Hz, 3H). | 615.3, 617.3 |
| Example 12 | 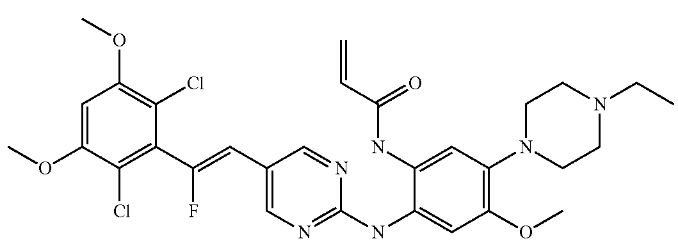 [SMILES: C=CC(=O)Nc1cc(N2CCN(CC)CC2)c(OC)cc1Nc1ncc(/C=C(\F)c2c(Cl)c(OC)cc(OC)c2Cl)cn1] | $^1$H NMR (400 MHz, CHLOROFORM-d) δ8.67 (s, 2 H) 8.63 (br s, 1 H) 8.34 (s, 1 H) 7.29 (s, 1 H) 7.17 (s, 1 H) 6.66 (s, 1 H) 6.40-6.47 (m, 1 H) 6.25-6.35 (m, 1 H) 5.65-5.80 (m, 2 H) 3.96 (s, 6 H) 3.86 (s, 3 H) 3.63 (br d, J = 11.29 Hz, 2 H) 3.51 (br d, J = 12.55 Hz, 2 H) 3.11-3.24 (m, 4 H) 2.96-3.06 (m, 2 H) 1.36-1.41 (m, 3 H) | 631.1 |
| Example 15 | 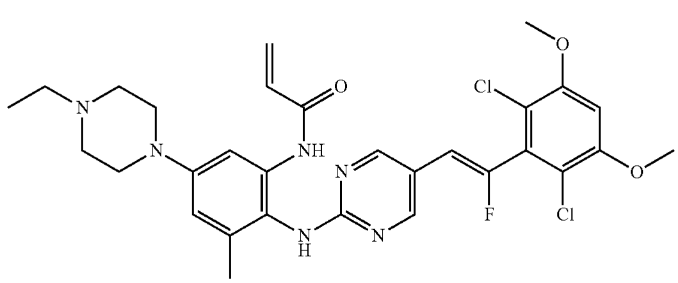 [SMILES: C=CC(=O)Nc1cc(N2CCN(CC)CC2)cc(C)c1Nc1ncc(/C=C(\F)c2c(Cl)c(OC)cc(OC)c2Cl)cn1] | $^1$H NMR (400 MHz, CHLOROFORM-d) δ8.62 (s, 2H), 8.03 (s, 1H), 7.79 (s, 1H), 6.83-6.49 (m, 3H), 6.36 (d, J = 16.8 Hz, 1H), 6.25-6.05 (m, 1H), 5.79-5.60 (m, 2H), 3.95 (s, 6H), 3.29 (s, 4H), 2.60 (s, 4H), 2.48 (d, J = 7.0 Hz, 2H), 2.19 (s, 3H), 1.14 (s, 3H). | 615.1 |

Scheme I
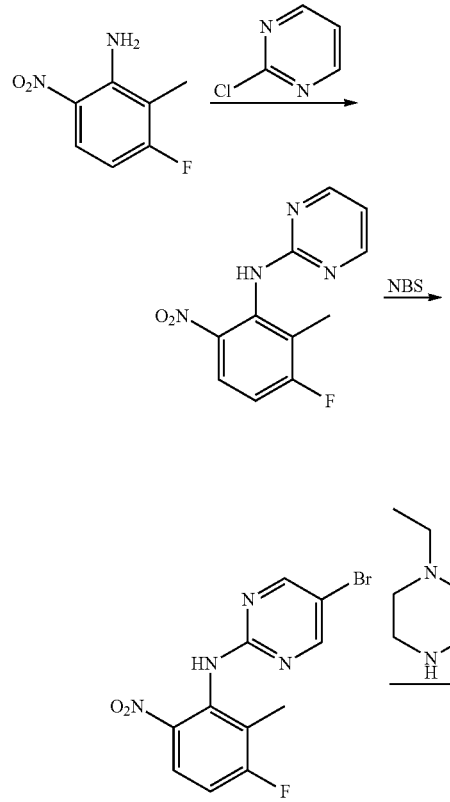
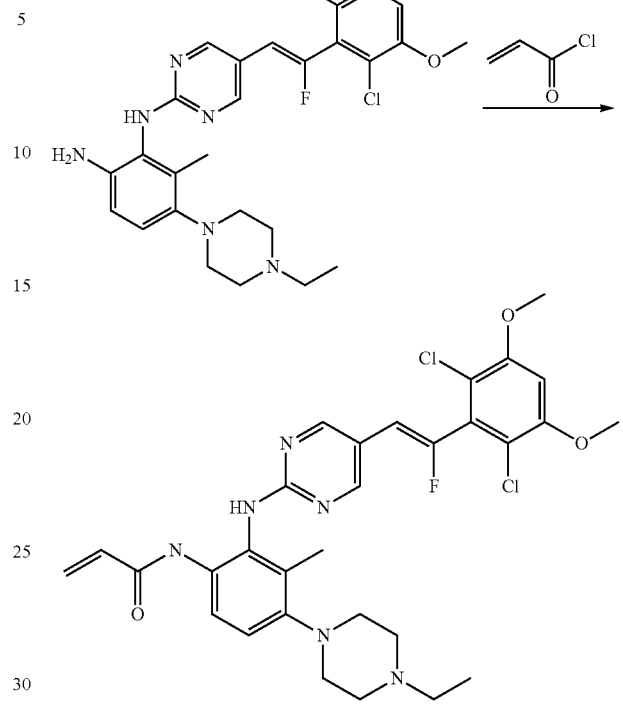
Example 13
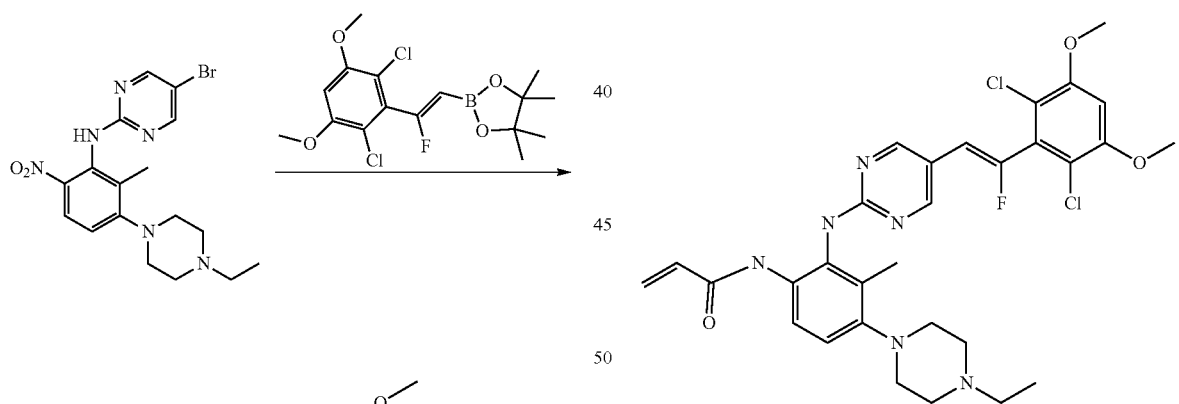
Example 13A
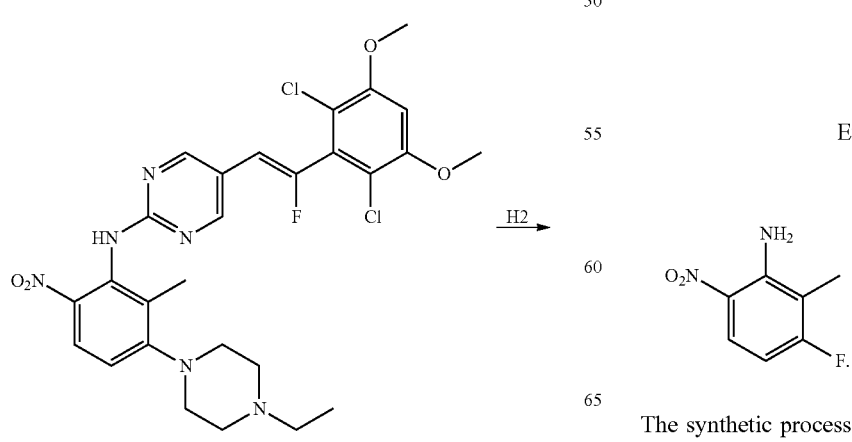
The synthetic process of Example 13A was as described in the control example 2H.

Example 13B

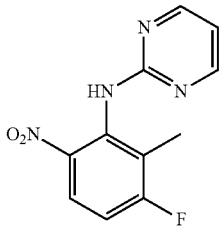

A solution of Example 13A (400 mg, 2.35 mmol), 2-chloropyrimidine (269 mg, 2.35 mmol), Pd2(dba)3 (107 mg, 0.12 mmol), Xphos (112 mg, 0.24 mmol), K₂CO₃ (974 mg, 7.05 mmol) in toluene (4 mL), after the replacement of nitrogen for 3 times, was heated to 110° C. and stirred for 12 hours. The TLC showed that the raw materials have been completely consumed. To the reaction solution was added 20 mL water, the mixture was extracted with ethyl acetate (20 ml×3) for 3 times. The organic phases were combined, and rotatory evaporated until dry to give a crude product, which was purified by column chromatography to give the Example 13B (470 mg, 80.58% yield).

¹H NMR (400 MHz, CHLOROFORM-d) δ 8.40 (d, J=5.0 Hz, 2H), 8.30 (br s, 1H), 7.97 (dd, J=5.6, 9.2 Hz, 1H), 7.12-7.00 (m, 1H), 6.80 (t, J=4.9 Hz, 1H).

Example 13C

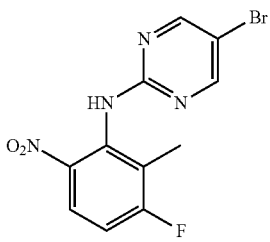 [SMILES: Cc1c(F)ccc([N+](=O)[O-])c1Nc1ncc(Br)cn1]

Example 13B (530 mg, 2.14 mmol) was dissolved in chloroform solution (7 mL), into which was added NBS (419 mg, 2.35 mmol) and the mixture was stirred at room temperature for 16 hours. The TLC showed that the raw materials have been completely consumed. The reaction solution was concentrated to give a crude product, which was purified over a flash silica gel column (petroleum ether:ethyl acetate=5:1) to give the Example 13C (460 mg, 65.71% yield) as a yellow solid.

¹H NMR (400 MHz, CHLOROFORM-d) δ 8.40 (s, 2H), 8.25 (br s, 1H), 7.98 (dd, J=5.5, 9.3 Hz, 1H), 7.11-6.98 (m, 1H).

Example 13D

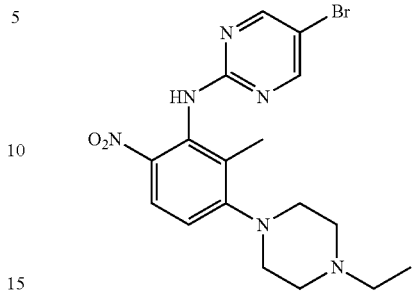

To a solution of Example 13C (1.15 g, 3.52 mmol) in DMSO (10 ml) was added ethylpiperazine (4.02 g, 35.20 mmol) batchwise, and the mixture was stirred at 130° C. for 16 hours. To the reaction solution was added 200 ml water, and the mixture was extracted with ethyl acetate (200 ml×3). The organic layers were combined and then washed with saturated saline (300 ml×2), dried over anhydrous sodium sulfate, filtered, and concentrated in vacuum, the residue of which was purified over a flash silica gel column (dichloromethane/methanol:10/1) to give the title compound Example 13D (1.30 g, 87.66% yield) as a yellow oil.

¹H NMR (400 MHz, CHLOROFORM-d) δ 8.38 (s, 2H), 8.36 (s, 1H), 7.96 (d, J=9.04 Hz, 1H), 6.89 (d, J=9.04 Hz, 1H), 3.12 (t, J=4.64 Hz, 4H), 2.63 (br s, 4H), 2.50 (q, J=7.28 Hz, 2H), 2.18 (s, 3H), 1.13 (t, J=7.16 Hz, 3H).

Example 13E

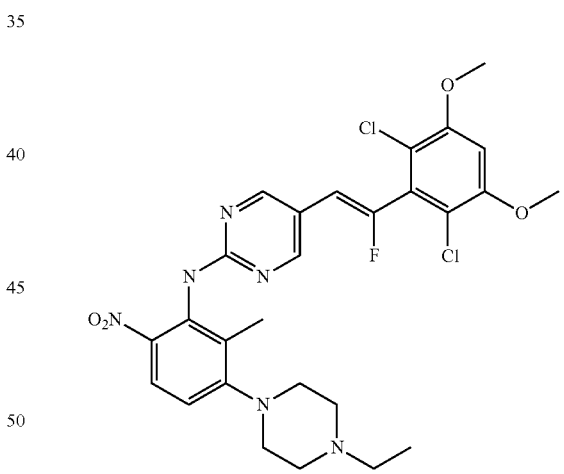

A mixed solution of Example 13D (350 mg, 830.786 µmol), Example 16 D (313.24 mg, 830.78 µmol), Pd(dppf)Cl₂ (60.79 mg, 83.08 µmol) and potassium phosphate (352.70 mg, 1.66 mmol) in dioxane (9 ml)/water (3 ml) was swept with nitrogen for 3 times, and the mixture was stirred at 100° C. for 1 hour under the atmosphere of nitrogen. The reaction was quenched with 20 ml water, and extracted with ethyl acetate (20 ml×3). The organic layers were combined, washed with saturated saline (50 ml×2), dried over anhydrous sodium sulfate, filtered, and concentrated in vacuum, the residue of which was purified over a flash silica gel column (dichloromethane/methanol:10/1) to give the title compound Example 13E (400 mg, 81.40% yield) as a yellow oil.

¹H NMR (400 MHz, CHLOROFORM-d) δ 8.63 (s, 2H), 8.50 (s, 1H), 7.97 (d, J=9.04 Hz, 1H), 6.89 (d, J=9.04 Hz, 1H), 6.64 (s, 1H), 5.60-5.77 (m, 1H), 3.94 (s, 6H), 3.09-3.18 (m, 4H), 2.65 (br s, 4H), 2.51 (q, J=7.20 Hz, 2H), 2.21 (s, 3H), 1.10-1.17 (m, 3H).

Example 13F

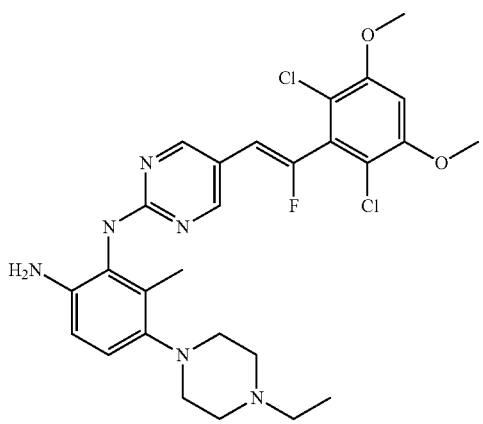 [SMILES: CCN1CCN(c2ccc([N+](=O)[O-])c(Nc3ncc(/C=C(\F)c4c(Cl)c(OC)cc(OC)c4Cl)cn3)c2C)CC1]

To a mixed solution of Example 13E (200 mg, 338.15 μmol) in ethanol (10 ml)/tetrahydrofuran (10 ml) was added Raney-Ni (28.97 mg, 338.15 μmol) under the atmosphere of nitrogen, and the mixture was stirred at 20° C. for 0.5 hours under the condition of hydrogen balloon (15 psi). The reaction was filtered, and concentrated in vacuum, the residue of which was not further purified to give the title compound Example 13F (200 mg, crude) as a yellow solid.
LCMS (ESI) m/z: 561.0 (M+1)

Example 13

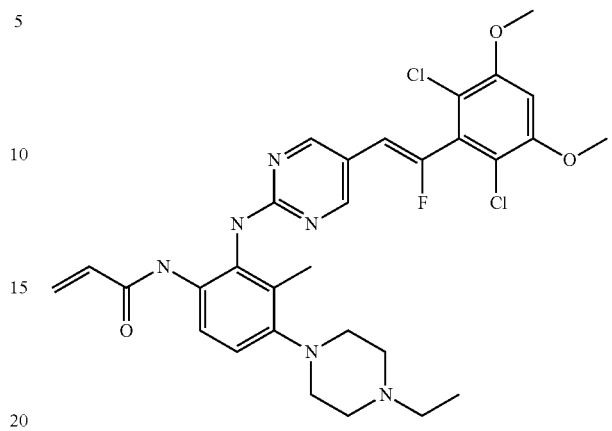

At 0° C., to a solution of Example 13F (200 mg, 356.20 μmol) in tetrahydrofuran (5 ml)/water (0.5 ml) was added chloropropionyl chloride (47.49 mg, 374.01 μmol), the mixture was stirred at 25° C. for 1 hour, into which was then added sodium hydroxide (56.99 mg, 1.42 mmol), and the mixture was stirred at 65° C. for 5 hours. The reaction was quenched with 20 ml water, and extracted with ethyl acetate (20 ml×3). The organic layers were combined, and then washed with saturated saline (50 ml×2), dried over anhydrous sodium sulfate, filtered, and concentrated in vacuum, the residue of which was purified by preparative HPLC to give the title compound Example 13 (30 mg, 11.90% yield).
LCMS (ESI) m/z: 615.1 (M+1)
¹H NMR (400 MHz, CHLOROFORM-d) δ 8.63 (s, 2H), 7.99 (br s, 1H), 7.81 (br d, J=8.54 Hz, 1H), 7.08 (d, J=8.78 Hz, 1H), 6.80 (s, 1H), 6.64 (s, 1H), 6.28-6.39 (m, 1H), 6.08-6.22 (m, 1H), 5.61-5.76 (m, 2H), 3.95 (s, 6H), 2.96 (t, J=4.64 Hz, 4H), 2.62 (br s, 3H), 2.50 (q, J=7.28 Hz, 2H), 2.22 (s, 3H), 1.14 (t, J=7.28 Hz, 3H).

The following one example was prepared according to the process as described in Example 13.

| Example | Structure | NMR Data | LCMS (ESI) m/z: (M + 1) |
| --- | --- | --- | --- |
| Example 14 | 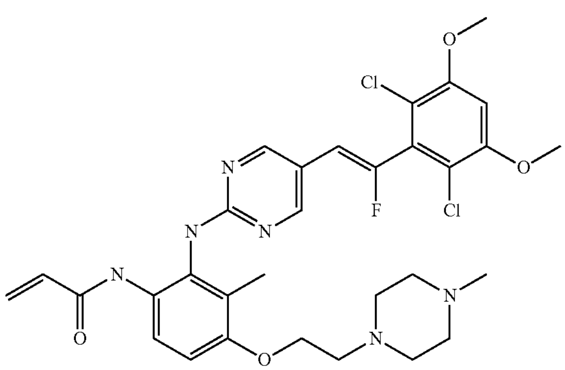 [SMILES: C=CC(=O)Nc1ccc(OCCN2CCN(C)CC2)c(C)c1Nc1ncc(/C=C(\F)c2c(Cl)c(OC)cc(OC)c2Cl)cn1] | ¹H NMR (400 MHz, CHLOROFORM-d) δ 8.62 (s, 2H), 7.96 (br s, 1H), 7.75 (br d, J = 9.04 Hz, 1H), 6.88-6.92 (m, 1H), 6.84 (d, J = 9.04 Hz, 1H), 6.64 (s, 1H), 6.27-6.37 (m, 1H), 6.08-6.20 (m, 1H), 5.61-5.75 (m, 2H), 4.12 (t, J = 5.78 Hz, 2H), 3.95 (s, 6H), 2.84 (t, J = 5.78 Hz, 2H), 2.34-2.74 (m, 8H), 2.29 (s, 3H), 2.13 (s, 3H) | 645.1 |

Scheme J
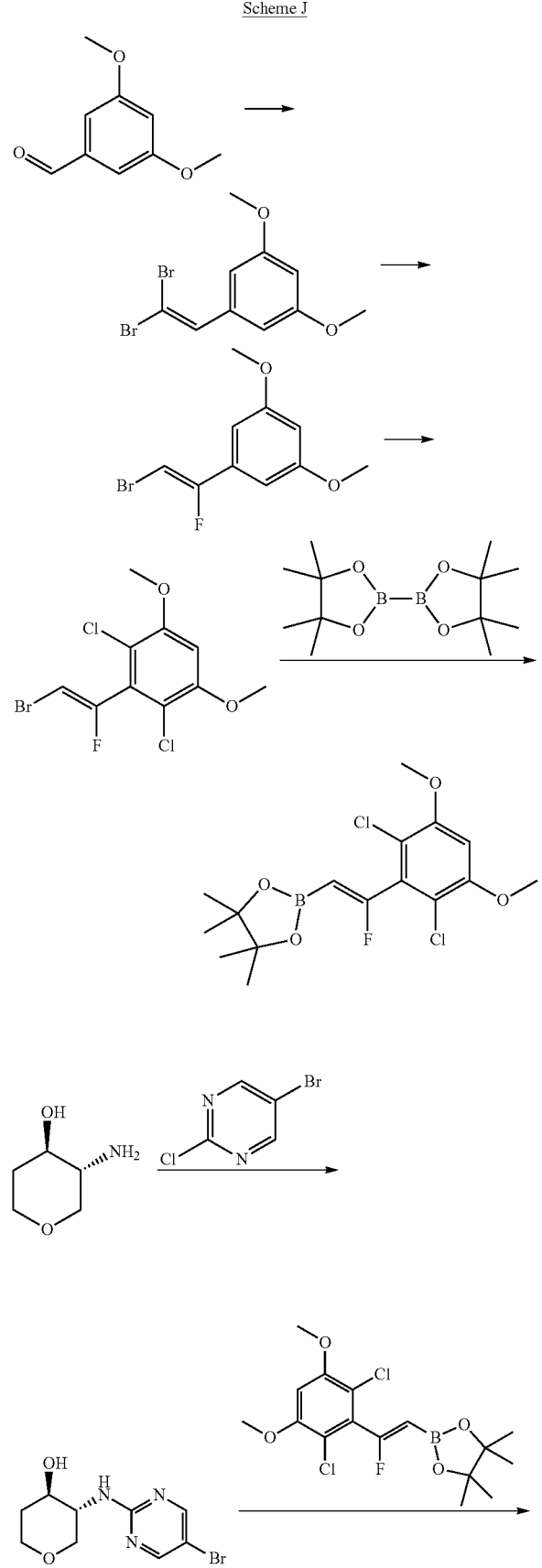
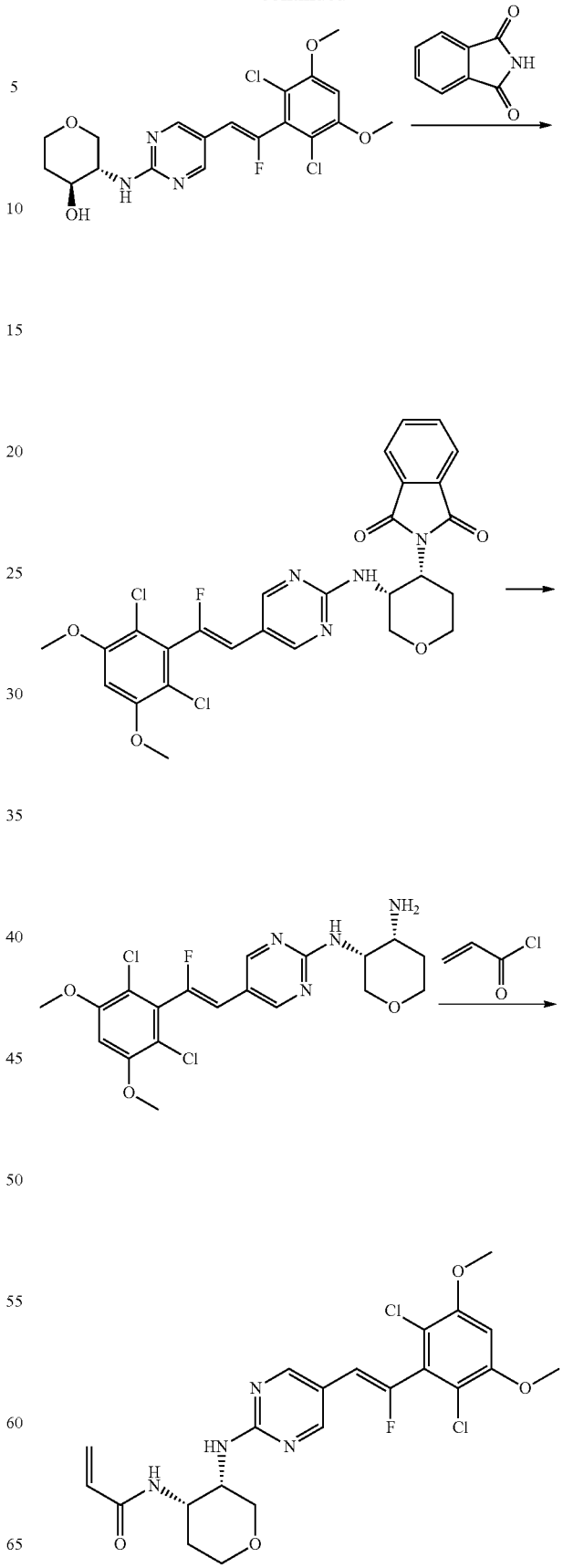

Example 16

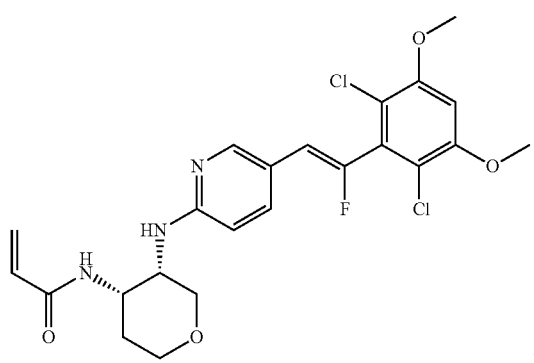

Example 16A

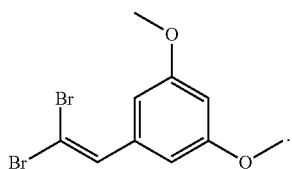

At 0° C., under the atmosphere of nitrogen, to a solution of triphenylphosphine (126.28 g, 481.43 mmol, 4.00 eq.) in dichloromethane (400.00 ml) was added carbon tetrabromide (79.83 g, 240.72 mmol, 2.00 eq.), and the mixture further reacted at 0° C. for 5 minutes. To the reaction solution was added 3,5-dimethoxy benzaldehyde (20.00 g, 120.36 mmol, 1.00 eq.), and the mixture was stirred at 0° C. for 4 hours. Thin layer chromatography detected that the raw materials have been reacted completely, and there was a new point with higher polarity. The two batches of reaction solution were combined, filtered, concentrated in vacuum, washed with 600 ml ethyl acetate, filtered, and concentrated in vacuum, the residue of which was purified over a flash silica gel column (petroleum ether/ethyl acetate=20/1) to give the Example 16A (39.92 g, yield: 84.20%) as a white solid.

$^1$H NMR (400 MHz, CHLOROFORM-d) δ 7.42 (s, 1H), 6.69 (d, J=2.26 Hz, 2H), 6.46 (t, J=2.26 Hz, 1H), 3.80 (s, 6H).

Example 16B

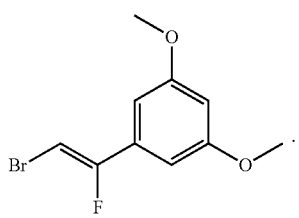

To a solution of Example 16A (20.00 g, 62.11 mmol, 1.00 eq.) in toluene (600 ml) was added tetrabutylammonium fluoride trihydrate (195.96 g, 621.10 mmol, 10.00 eq.) and the mixture was reacted at 110° C. for 16 hours. When thin layer chromatography detected that the raw materials have been reacted completely, the reaction solution was diluted with 1200 ml water, and extracted with 900 ml ethyl acetate. The organic phase was dried over anhydrous sodium sulfate, filtered, and concentrated in vacuum, the residue of which was purified over a flash silica gel column (petroleum ether/ethyl acetate=20/1) to give the Example 16B (12.84 g, yield: 79.18%) as a yellow liquid.

$^1$H NMR (400 MHz, CHLOROFORM-d) δ 6.65 (d, J=2.26 Hz, 1H), 6.62 (d, J=2.26 Hz, 2H), 6.07-6.16 (m, 1H), 3.80 (s, 6H).

Example 16C

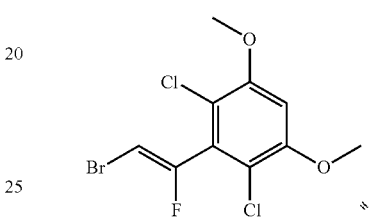

To a solution of Example 16B (24.80 g, 94.99 mmol, 1.00 eq.) in tetrahydrofuran (500.00 ml) was dropwise added a solution of sulfonyl chloride (32.05 g, 237.48 mmol, 23.74 ml, 2.50 eq.) in tetrahydrofuran (15 ml) at −5° C. The reaction solution was reacted between −5° C. and 5° C. for 3 hours, into which was supplemented a solution of sulfonyl chloride (1 ml) in tetrahydrofuran (10 ml), and the mixture further reacted between −5° C. and 5° C. for 1 hour. When thin layer chromatography detected that the reaction has been completed, the reaction solution was quenched with a saturated aqueous solution of sodium bicarbonate (150 ml), extracted with ethyl acetate (70 ml for each time) for three times. The organic phase was dried over anhydrous sodium sulfate, filtered, dried and concentrated, the residue of which was purified over a flash silica gel column (petroleum ether/ethyl acetate=9/1) to give the Example 16C (27.75 g, yield: 88.53%) as a yellow solid.

$^1$H NMR (400 MHz, CHLOROFORM-d) δ 6.57 (s, 1H), 5.78-5.87 (m, 1H), 3.94 (s, 6H)

Example 16D

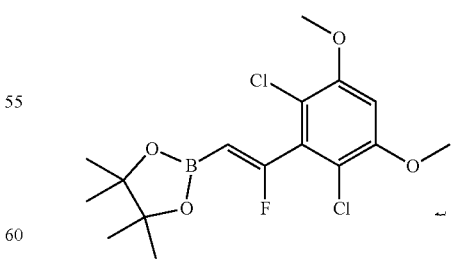

To a solution of Example 16C (20.00 g, 60.61 mmol, 1.00 eq.) and bis(pinacolato)diboron (30.78 g, 121.22 mmol, 2.00 eq.) in dioxane (300 ml) were added tri(dibenzylidene acetone)dipalladium (5.55 g, 6.06 mmol, 0.10 eq.), tricyclohexyl phosphine (6.80 g, 24.24 mmol, 0.40 eq.), potassium acetate (23.79 g, 242.44 mmol, 4.00 eq.), and the mixture reacted at 90° C. for 16 hours under the atmosphere of nitrogen. When thin layer chromatography detected that the reaction has been completed, the reaction solution was filtered, and concentrated in vacuum, the residue of which was purified over a flash silica gel column (petroleum ether/ethyl acetate=4/1) to give the Example 16D (16.82 g, yield 73.60%) as a yellow solid.

¹H NMR (400 MHz, CHLOROFORM-d) δ 6.59 (s, 1H), 4.82-4.97 (m, 1H), 3.92 (s, 6H), 1.25-1.28 (m, 12H), 1.17-1.19 (m, 1H).

Example 16E

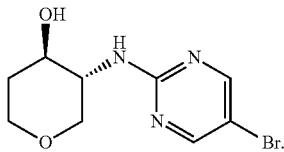 [SMILES: O[C@@H]1CCOC[C@H]1Nc1ncc(Br)cn1]

To a solution of (3R, 4R)-3-amino-tetrahydro-2H-pyran-4-ol (2.02 g, 17.25 mmol, 1.51 eq.) and 2-chloro-5-bromopyrimidine (2.21 g, 11.43 mmol, 1.00 eq.) in dioxane (40.00 ml) was added N,N-diisopropyl ethyl amine (4.45 g, 34.43 mmol, 6.01 ml, 3.01 eq.), the mixture was reacted at 105° C. for 16 hours. When thin layer chromatography detected that the reaction has been completed, the reaction solution was diluted with 30 ml water, extracted with ethyl acetate (50 ml for each time) for 3 times. The organic phase was dried over anhydrous sodium sulfate, filtered, concentrated in vacuum, purified over a column by employing the proportion of petroleum ether/ethyl acetate=1/1 and then a proportion of dichloromethane/methanol=10/1, to give the Example 16E (2.60 g, yield 83.06%) as a yellow oil.

¹H NMR (400 MHz, CHLOROFORM-d) δ 8.28 (s, 2H), 5.47 (br d, J=7.28 Hz, 1H), 4.05-4.18 (m, 1H), 3.95 (td, J=4.48, 11.60 Hz, 1H), 3.84 (dq, J=4.14, 7.82 Hz, 1H), 3.70-3.79 (m, 1H), 3.42-3.55 (m, 4H), 3.25 (dd, J=8.02, 11.28 Hz, 1H), 2.08 (ddd, J=2.26, 4.58, 6.71 Hz, 1H), 2.02-2.11 (m, 1H), 1.70 (dtd, J=4.26, 9.24, 13.64 Hz, 1H).

Example 16F

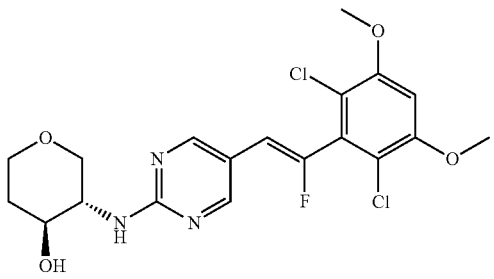 [SMILES: COc1cc(OC)c(Cl)c(/C(F)=C/c2cnc(N[C@H]3COCC[C@@H]3O)nc2)c1Cl]

To a mixed solution of Example 16E (795.00 mg, 2.90 mmol, 1.00 eq.) and Example 16D (1.44 g, 3.83 mmol, 1.32 eq.) in dioxane (12.00 ml) and water (4.00 ml) were added 1,1-bis(diphenylphosphine)ferrocene palladium dichloride (254.64 mg, 348.00 μmol, 0.12 eq.), potassium phosphate (1.54 g, 7.25 mmol, 2.50 eq.), and the mixture was reacted at 100° C. for 1.5 hours under the atmosphere of nitrogen. When thin layer chromatography and liquid chromatography-mass spectrometer detected that the reaction has been completed, the reaction solution was filtered, diluted with 30 ml water, extracted with ethyl acetate (15 ml for each time) for 3 times. The organic phase was dried over anhydrous sodium sulfate, filtered, and concentrated in vacuum, the residue of which was purified over a flash silica gel column (petroleum ether/ethyl acetate=2/3) to give Example 16F (513.00 mg, yield: 39.82%) as a yellow solid.

LCMS (ESI): 444.2 [M+H]⁺.

¹H NMR (400 MHz, CHLOROFORM-d) δ 8.56 (s, 2H), 6.64 (s, 1H), 5.60-5.73 (m, 1H), 5.33 (br d, J=7.02 Hz, 1H), 4.14-4.17 (m, 1H), 3.94-3.97 (m, 6H), 3.77 (dt, J=4.38, 8.72 Hz, 1H), 3.44-3.54 (m, 1H), 3.27 (dd, J=8.78, 11.04 Hz, 1H), 2.06-2.12 (m, 1H), 1.65-1.79 (m, 2H).

Example 16G

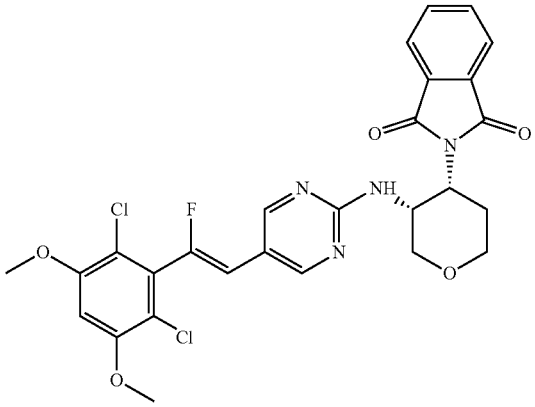 [SMILES: COc1cc(OC)c(Cl)c(/C(F)=C/c2cnc(N[C@H]3COCC[C@H]3N3C(=O)c4ccccc4C3=O)nc2)c1Cl]

To a solution of Example 16F (513.00 mg, 1.15 mmol, 1.00 eq.), phthalimide (203.04 mg, 1.38 mmol, 1.20 eq.) and triphenylphosphine (44.28 mg, 168.81 μmol, 1.50 eq.) in tetrahydrofuran (6.00 ml) was added diisopropyl azodicarboxylate (348.81 mg, 1.73 mmol, 335.40 pd, 1.50 eq.), and the mixture was reacted at 20° C. for half an hour. When thin layer chromatography and liquid chromatography-mass spectrometer detected that the reaction has been completed, the reaction solution was filtered, and concentrated in vacuum, the residue of which was purified over a flash silica gel column (petroleum ether/ethyl acetate=1/1) to give Example 16G (659.00 mg, yield 100.00%) as a yellow gel.

LCMS (ESI): 573.4 [M+H]⁺.

¹H NMR (400 MHz, CHLOROFORM-d) δ 8.74 (s, 1H), 7.72-7.76 (m, 2H), 7.51-7.58 (m, 6H), 6.62 (s, 1H), 5.34-5.47 (m, 1H), 5.34-5.47 (m, 1H), 4.16-4.25 (m, 1H), 4.07-4.15 (m, 2H), 3.93-3.96 (m, 6H), 3.77 (dd, J=1.76, 12.04 Hz, 1H), 3.39-3.67 (m, 2H), 1.77-1.82 (m, 1H), 1.77-1.82 (m, 1H).

105
Example 16H

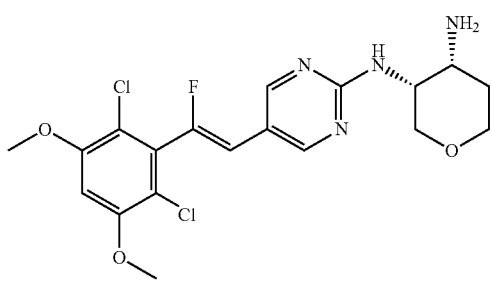 [SMILES: COc1cc(OC)c(Cl)c(/C(F)=C/c2cnc(N[C@H]3COCC[C@H]3N)nc2)c1Cl]

106
Example 16

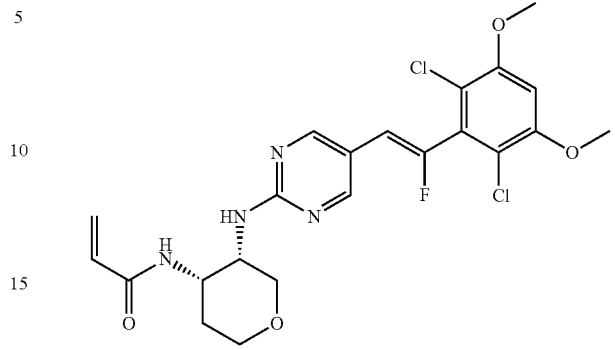

At 0° C., to a solution of Example 16H (246.00 mg, 554.93 μmol, 1.00 eq.) and N,N-diisopropyl ethyl amine (222.33 mg, 1.72 mmol, 300.45 μl, 3.10 eq.) in dichloromethane (20.00 ml) was added acryloyl chloride (44.40 mg, 490.55 μmol, 40.00 μl, 0.88 eq.), and the mixture was reacted at 0° C. for 1 hour. When liquid chromatography-mass spectrometer detected that the reaction has been completed, the reaction solution was quenched with 20 ml saturated aqueous solution of sodium bicarbonate, extracted with ethyl acetate (10 ml for each time) for 3 times. The organic phase was dried over anhydrous sodium sulfate, filtered, and concentrated in vacuum, the crude product of which was purified by high performance liquid chromatography (trifluoroacetic acid system) to give Example 16 (150.00 mg, yield 54.35%).

LCMS (ESI): 497.4 [M+H]$^+$.

$^1$H NMR (400 MHz, CHLOROFORM-d) δ 8.72 (br s, 1H), 8.54 (br s, 1H), 6.80 (br d, J=7.52 Hz, 1H), 6.59 (s, 1H), 6.18 (dd, J=1.00, 17.06 Hz, 1H), 5.94-6.03 (m, 1H), 5.58-5.70 (m, 1H), 5.54-5.58 (m, 1H), 4.27-4.40 (m, 2H), 4.06-4.14 (m, 1H), 3.97 (br d, J=10.04 Hz, 1H), 3.89 (s, 6H), 3.46-3.60 (m, 2H), 1.93-2.06 (m, 1H), 1.82 (br d, J=10.54 Hz, 1H).

To a solution of Example 16G (659.00 mg, 1.15 mmol, 1.00 eq.) in ethanol (10.00 ml) was added hydrazine hydrate (230.13 mg, 4.60 mmol, 223.43 μl, 4.00 eq.), and the mixture was reacted at 80° C. for 1 hour. When thin layer chromatography detected that the reaction has been completed, the reaction solution was filtered, and concentrated in vacuum, the residue of which was purified over a flash silica gel column (dichloromethane/methanol=9/1) to give Example 16H (312.00 mg, yield 61.20%) as a yellow gel.

$^1$H NMR (400 MHz, CHLOROFORM-d) δ 8.47 (s, 2H), 6.57 (s, 1H), 5.52-5.64 (m, 1H), 4.22-4.32 (m, 1H), 4.05 (q, J=7.02 Hz, 1H), 3.93 (br s, 1H), 3.87-3.91 (m, 6H), 3.82 (dd, J=3.64, 11.66 Hz, 1H), 3.55 (dd, J=2.12, 11.66 Hz, 1H), 3.44 (dt, J=2.88, 11.10 Hz, 1H), 3.10 (td, J=4.10, 10.34 Hz, 1H), 1.66-1.75 (m, 1H), 1.54-1.63 (m, 1H).

Scheme K

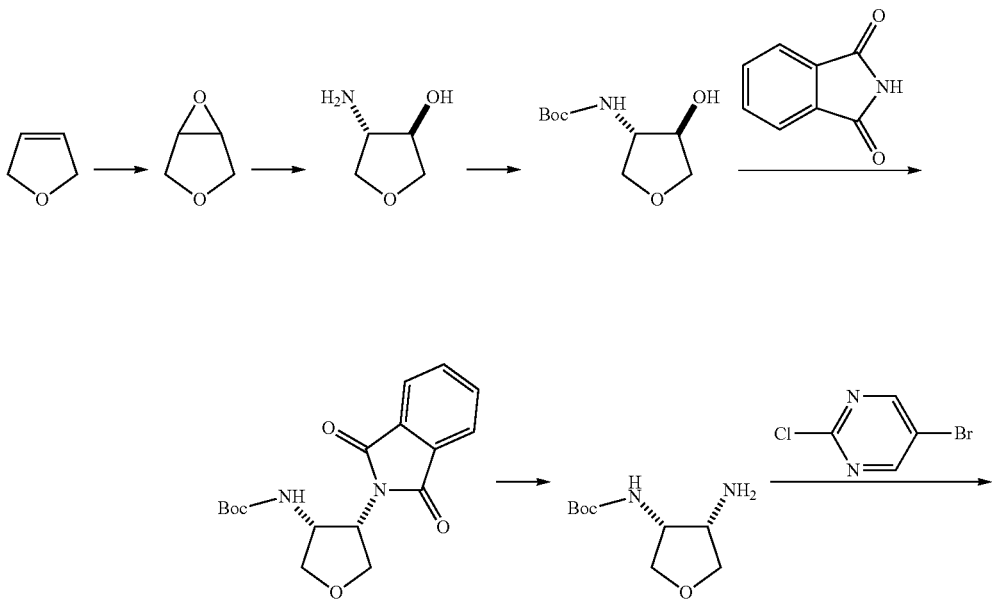

107 108
-continued
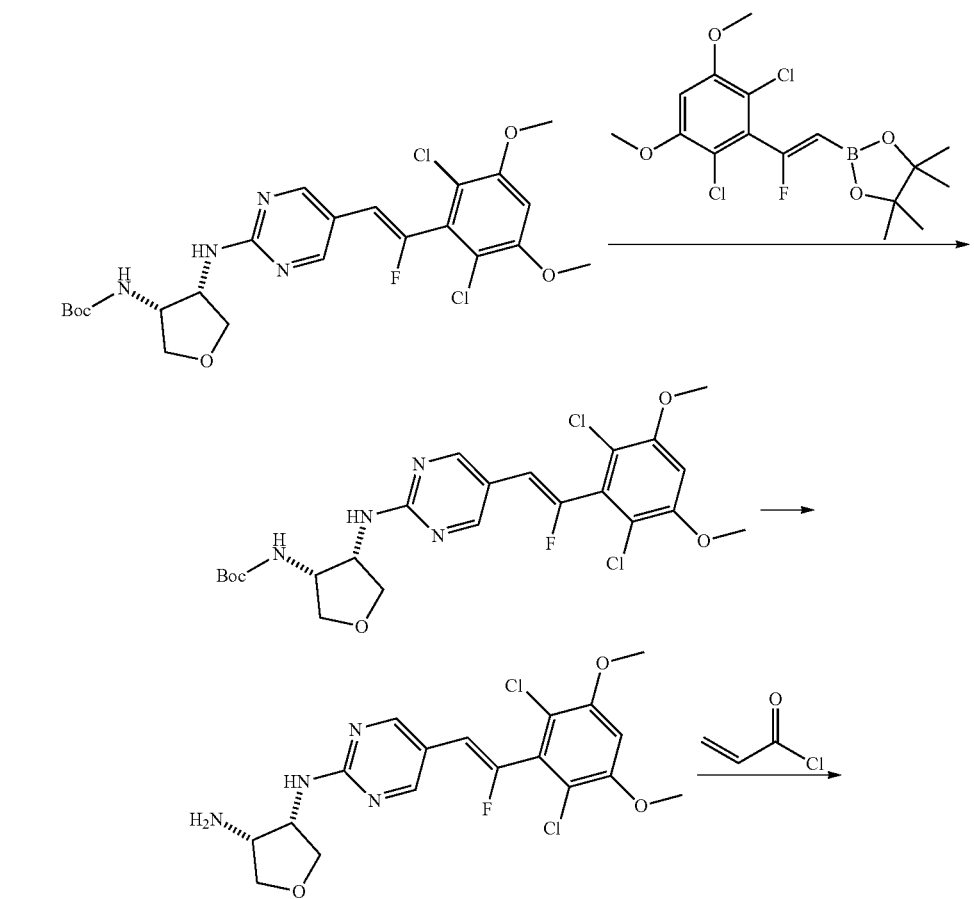
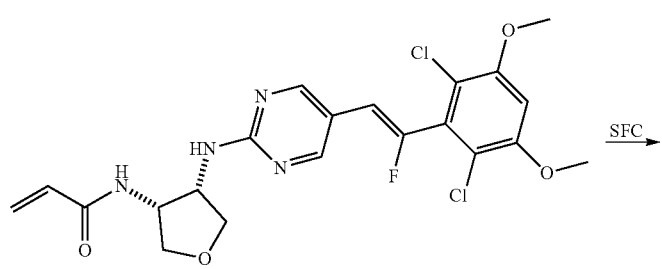
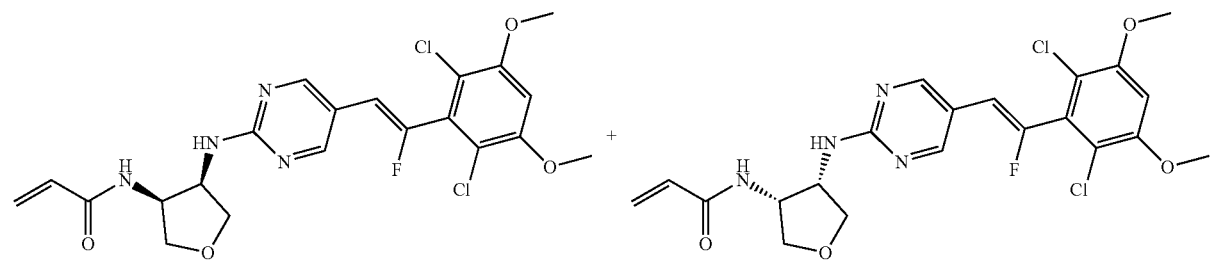 [SMILES: C=CC(=O)N[C@@H]1COC[C@@H]1Nc1ncc(/C=C(\F)c2c(Cl)c(OC)cc(OC)c2Cl)cn1 ; C=CC(=O)N[C@H]1COC[C@H]1Nc1ncc(/C=C(\F)c2c(Cl)c(OC)cc(OC)c2Cl)cn1]

Example 19

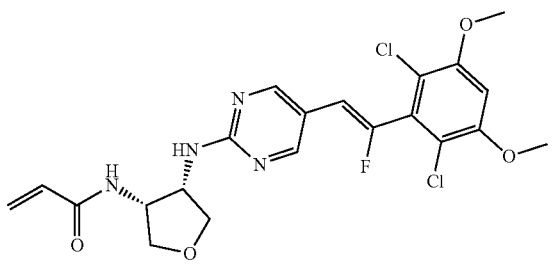 [SMILES: C=CC(=O)N[C@H]1COC[C@H]1Nc1ncc(/C=C(\F)c2c(Cl)c(OC)cc(OC)c2Cl)cn1]

Example 19A

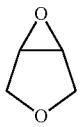

2,5-dihydrofuran (80.00 g, 1.14 mol, 86.02 ml) was dissolved in 1000 ml dichloromethane, into which was then added m-chloroperoxybenzoic acid (277.74 g, 1.37 mol) batchwise, and the mixture was reacted at room temperature for 14 h. When TLC detected that the reaction has been completed, the solid was filtered off, the filtrate was washed with a saturated solution of sodium sulfite until the starch-KI paper didn't become blue anymore, and then washed with a saturated solution of sodium bicarbonate until the PH of the solution=7~8. The organic phase was dried over anhydrous sodium sulfate, filtered and the solvent was removed by rotatory evaporation to give 48.50 g yellow product Example 19A without being further purified, with a yield of 49.4%.

$^1$HNMR (400 MHz, CHLOROFORM-d) δ 3.99 (d, J=10.29 Hz, 2H), 3.77 (s, 2H), 3.63 (d, J=10.54 Hz, 2H).

Example 19B

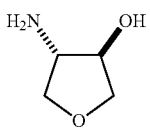

To a reaction flask were added Example 19A (24.00 g, 278.78 mmol) and ammonia water (218.40 g, 1.74 mol, 240.00 ml), and the mixture was reacted at 100° C. for 14 hours. When TLC detected that the reaction has been completed, the solvent was removed by rotatory evaporation to give 23.70 g crude Example 19B as a brown oil, with a yield of 82.4%.

$^1$HNMR (400 MHz, CHLOROFORM-d) δ 4.00-4.16 (m, 3H), 3.63-3.81 (m, 1H), 3.48-3.59 (m, 1H), 3.34-3.45 (m, 1H).

Example 19C

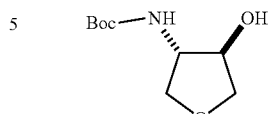

Example 19B (23.70 g, 229.83 mmol) was dissolved in 200 ml methanol, into which was added triethyl amine (4.65 g, 45.97 mmol, 6.37 ml), and then dropwise added Boc-anhydride (65.21 g, 298.78 mmol, 68.64 ml), and the mixture was reacted at room temperature for 3 hours. When TLC detected that the reaction has been completed, the solvent was removed by rotatory evaporation, and then 100 ml methyl tert-butyl ether was added, and the mixture was stirred for 15 minutes. The filter cake after being filtered was the product, which need not to be further purified to give 38.78 g Example 19C as a light yellow solid, with a yield of 83.0%.

$^1$HNMR (400 MHz, CHLOROFORM-d) δ 4.78 (br s, 1H), 4.24-4.31 (m, 1H), 3.98-4.13 (m, 2H), 3.94 (br s, 1H), 3.66-3.73 (m, 1H), 3.62 (dd, J=2.76, 9.29 Hz, 1H), 1.44 (s, 9H).

Example 19D

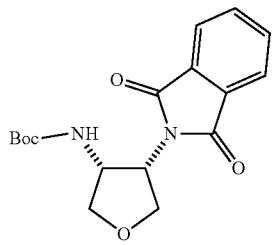 [SMILES: CC(C)(C)OC(=O)N[C@H]1COC[C@H]1N1C(=O)c2ccccc2C1=O]

Example 19C (38.78 g, 190.82 mmol), phthalimide (33.69 g, 228.98 mmol) and triphenylphosphine (60.06 g, 228.98 mmol) were dissolved in 500 ml tetrahydrofuran, into which was added diisopropyl azodicarboxylate (46.30 g, 228.98 mmol, 44.52 ml), and the mixture was reacted at room temperature for 14 hours. When TLC detected that the reaction has been completed, the solvent was removed by rotatory evaporation, and the mixture was purified over a flash silica gel column (petroleum ether/ethyl acetate=3/1) to give 85.50 g product Example 19D as a white solid.

$^1$HNMR (400 MHz, CHLOROFORM-d) δ 7.85-7.88 (m, 2H), 7.74-7.76 (m, 2H), 4.88 (br d, J=9.54 Hz, 1H), 4.44-4.55 (m, 1H), 4.37 (br t, J=8.16 Hz, 1H), 4.12-4.21 (m, 2H), 3.78-3.90 (m, 1H), 1.10 (s, 9H).

Example 19E

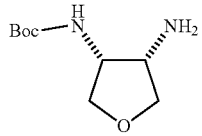 [SMILES: CC(C)(C)OC(=O)N[C@H]1COC[C@H]1N]

Example 19D (85.50 g, 257.26 mmol) was dissolved in 850 ml absolute ethanol, into which was added hydrazine hydrate (75.76 g, 2572.6 mmol, 73.55 ml), and the mixture was reacted at 80° C. for 1 hour. When TLC detected that the reaction has been completed, the resulting white solid was filtered off, and the solvent was removed by rotatory evaporation, into the residue was further added 200 ml dichloromethane. The undissolved solid was filtered off, and the solvent was removed by rotatory evaporation, 49.6 g crude product Example 19E was given as a yellowish solid which needs not to be further purified.

$^1$HNMR (400 MHz, CHLOROFORM-d) δ 5.32 (br s, 1H), 4.06-4.17 (m, 1H), 3.94-4.05 (m, 2H), 3.52-3.62 (m, 2H), 3.47 (dd, J=5.02, 9.03 Hz, 1H), 1.36-1.50 (m, 9H).

Example 19F

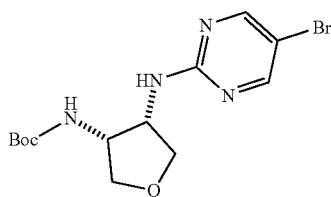

Example 19E (14.00 g, 69.22 mmol) and 2-chloro-5-bromopyrimidine (11.38 g, 58.84 mmol) were dissolved in 100 ml NMP, into which was added sodium bicarbonate (17.45 g, 207.66 mmol), and the mixture was reacted at 110° C. for 14 hours. When TLC detected that the reaction has been completed, 300 ml ethyl acetate was added, then the mixture was washed with saturated saline solution (200 ml*3). The organic phase was dried over with anhydrous sodium sulfate, filtered and the solvent was removed by rotatory evaporation, then purified over a flash silica gel column (petroleum ether/ethyl acetate=3/1), to give 15.66 g Example 19F as a yellow solid, with a yield of 62.97%.

$^1$HNMR (400 MHz, CHLOROFORM-d) δ 8.30 (s, 2H), 5.71 (br s, 1H), 4.58-4.70 (m, 1H), 4.44 (br s, 1H), 4.03-4.11 (m, 2H), 3.63-3.73 (m, 2H), 2.04 (s, 4H), 1.38 (s, 9H).

Example 19G

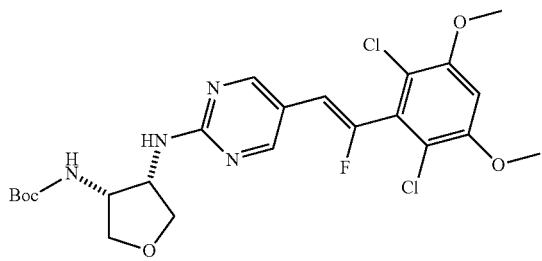 [SMILES: COc1cc(OC)c(Cl)c(/C(F)=C/c2cnc(N[C@@H]3COC[C@@H]3NC(=O)OC(C)(C)C)nc2)c1Cl]

Example 19F (15.62 g, 43.47 mmol), Example 16D (14.90 g, 39.52 mmol) were dissolved in 150 ml 1,4-dioxane and 75 ml water, into which were added Pd(dppf)Cl$_2$ (2.89 g, 3.95 mmol) and anhydrous potassium phosphate (16.78 g, 79.04 mmol) and the mixture was reacted at 95° C. for 14 hours under the atmosphere of nitrogen. When TLC detected that the reaction has been completed, 300 mL ethyl acetate was added, then the mixture was washed with saturated saline solution (200 ml*3). The organic phase was dried over anhydrous sodium sulfate, filtered and the solvent was removed by rotatory evaporation, the residue of which was purified over a flash silica gel column (petroleum ether/ethyl acetate=1/1) to give 4.6 g Example 19G as a yellow solid, with a yield of 21.99%.

$^1$HNMR (400 MHz, CHLOROFORM-d) δ 8.57 (s, 2H), 6.64 (s, 1H), 5.79 (br d, J=6.53 Hz, 1H), 5.58-5.72 (m, 1H), 5.09 (br s, 1H), 4.70-4.80 (m, 1H), 4.47 (br s, 1H), 4.12-4.23 (m, 2H), 3.72 (br d, J=6.78 Hz, 2H), 1.39 (s, 9H).

Example 19H

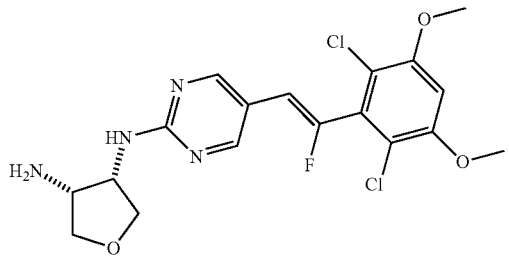 [SMILES: COc1cc(OC)c(Cl)c(/C(F)=C/c2cnc(N[C@@H]3COC[C@@H]3N)nc2)c1Cl]

Example 19G (4.60 g, 8.69 mmol) was dissolved in 30 ml DCM, into which was dropwise added trifluoroacetic acid (15.40 g, 135.04 mmol, 10.00 ml), and the mixture was reacted at room temperature for 30 min. When LC-MS detected that the reaction has been completed, the solvent was removed by rotatory evaporation, 7.20 g crude product Example 19H was given as a tan solid which needs not to be further purified.

LCMS (ESI): 429 (M+1)$^+$

Example 19

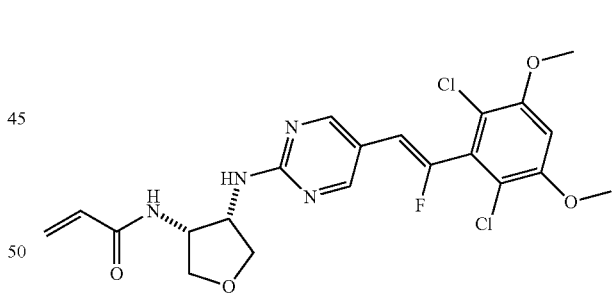

Example 19H (7.20 g, 13.25 mmol) was dissolved in 40 mL DCM, into which was added DIEA (6.85 g, 53.00 mmol). The reaction solution was cooled to 0° C., into which was added acryloyl chloride (599.63 mg, 6.63 mmol μL), then warmed to room temperature and reacted for 20 mins. When LC-MS detected that the reaction has been completed, the reaction was quenched with 30 ml water and then extracted with dichloromethane (15 ml*3). The organic phases were combined, then washed with 40 mL saturated saline, dried over anhydrous sodium sulfate, filtered and rotatory evaporated, and purified over a flash silica gel column (first petroleum ether/ethyl acetate=1/1, then dichloromethane/methanol=10/1) to give 2.7 g Example 19 (yield in two steps, 64.3%).

Examples 20, 21

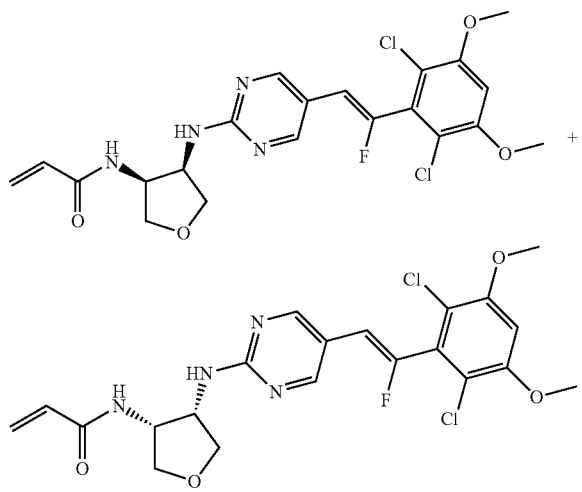

Example 19 (2.7 g, 5.59 mmol) was resolved by SFC (column: OD (250 mm*30 mm, 5 μm); mobile phase: [0.1% NH₃H₂O EtOH]; B %: 40%-40%, 10 min) to give 830 mg Example 20 (purity: 98.43%) with a retention time of 5.204, and 610 mg Example 21 (purity: 99.22%) with a retention time of 7.294.

Example 20: ¹H NMR (400 MHz, CHLOROFORM-d) δ 8.57 (s, 2H), 6.65 (s, 1H), 6.38 (br d, J=6.53 Hz, 1H), 6.25 (dd, J=1.13, 16.94 Hz, 1H), 5.98-6.11 (m, 1H), 5.59-5.78 (m, 3H), 4.70-4.85 (m, 2H), 4.20 (ddd, J=6.02, 9.47, 12.36 Hz, 2H), 3.92-3.98 (m, 6H), 3.70-3.83 (m, 2H).

Example 21: ¹H NMR (400 MHz, CHLOROFORM-d) δ 8.58 (s, 2H), 6.65 (s, 1H), 6.35 (br d, J=6.27 Hz, 1H), 6.21-6.29 (m, 1H), 5.99-6.10 (m, 1H), 5.59-5.74 (m, 3H), 4.69-4.82 (m, 2H), 4.20 (ddd, J=6.02, 9.47, 13.11 Hz, 2H), 3.95 (s, 6H), 3.77 (ddd, J=4.52, 9.54, 16.56 Hz, 2H).

The following 3 examples were prepared according to the process as described in Example 19.

| Examples | Structure | NMR Data | LCMS (ESI) m/z: (M + 1) |
|---|---|---|---|
| Example 32 | 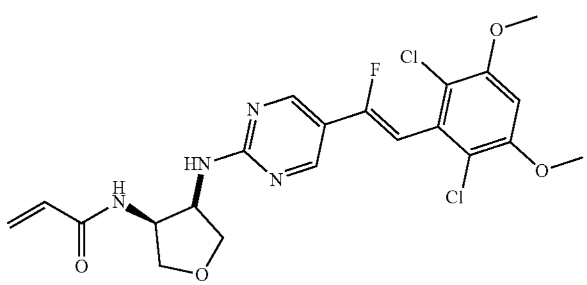 [SMILES: C=CC(=O)N[C@@H]1COC[C@@H]1Nc1ncc(/C(F)=C/c2c(Cl)c(OC)cc(OC)c2Cl)cn1] | 1H NMR (400 MHz, CHLOROFORM-d) δ 9.25 (br d, J = 5.27 Hz, 1H), 8.63 (br d, J = 4.02 Hz, 2H), 6.52-6.62 (m, 2H), 6.27-6.32 (m, 1H), 6.21-6.26 (m, 1H), 6.06-6.14 (m, 1H), 5.66 (dd, J = 1.38, 10.16 Hz, 1H), 4.87-4.98 (m, 2H), 4.14-4.22 (m, 2H), 3.94 (s, 6H), 3.81-3.89 (m, 2H) | 483.3 |
| Example 25 | 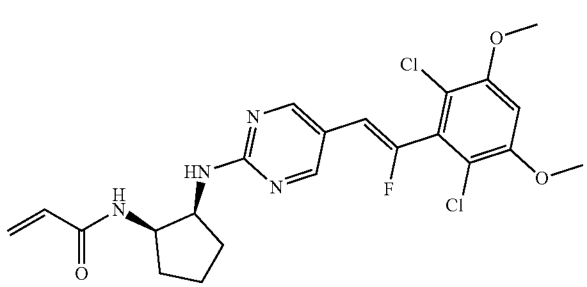 [SMILES: C=CC(=O)N[C@@H]1CCC[C@@H]1Nc1ncc(/C=C(\F)c2c(Cl)c(OC)cc(OC)c2Cl)cn1] | ¹H NMR (400 MHz, CHLOROFORM-d) δ 8.49 (s, 2H), 6.58 (s, 1H), 6.35 (br d, J = 7.1 Hz, 1H), 6.15 (dd, J = 1.3, 17.0 Hz, 1H), 6.03-5.92 (m, 1H), 5.57-5.49 (m, 1H), 3.88 (s, 6H), 2.82-2.68 (m, 1H), 2.74 (br s, 1H), 2.21-1.98 (m, 2H), 1.84-1.56 (m, 4H). | 481.0 |

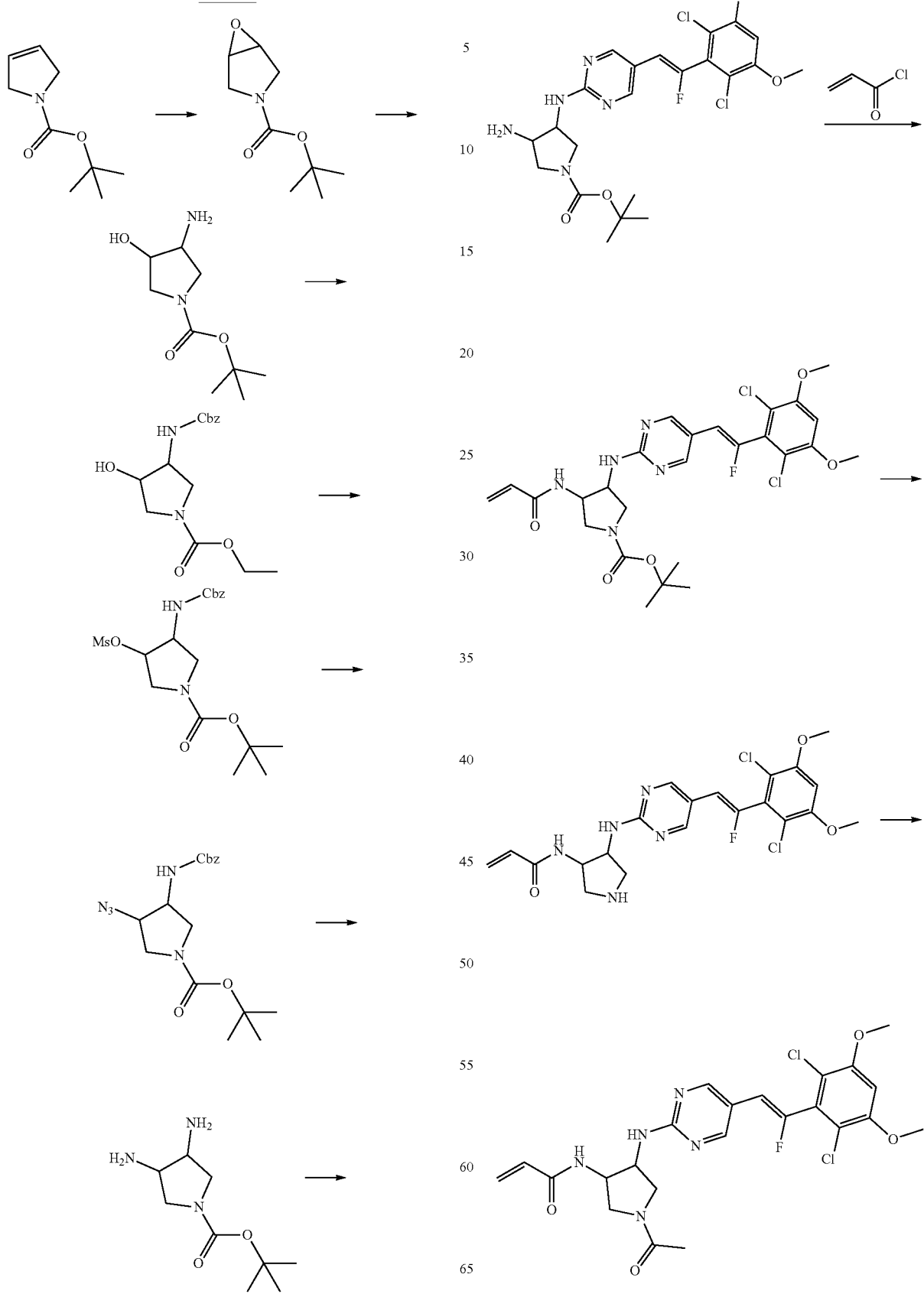

Example 34

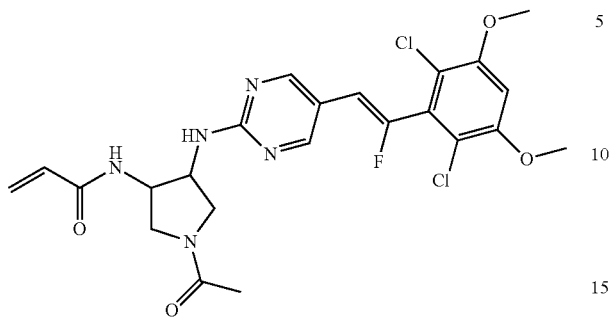

Example 34A

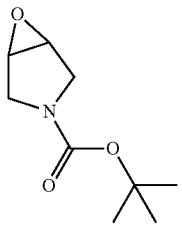

To a solution of N-Boc-2,5-dihydropyrrole (25 g, 147.74 mmol) in 200 ml dichloromethane was added m-chloroperoxybenzoic acid (38.24 g, 221.61 mmol) batchwise, the reaction solution was stirred at 25° C. for 16 hours. The TLC (phosphomolybdic acid) showed that there was a primarily new spot generated. The reaction solution was quenched with a saturated solution of sodium sulfite (500 ml), and extracted with dichloromethane (150 ml×2) for 2 times. The organic phase was layered, washed with an aqueous solution of sodium carbonate (300 ml×2) for 2 times, and washed with saline (300 ml×2) for two times, dried over anhydrous sodium sulfate, filtered, and concentrated to give the product Example 34A (22.5 g, 82.22% yield) as a light yellow oil, which was used directly in the next step.

$^1$H NMR (400 MHz, CHLOROFORM-d) δ=3.78 (d, J=6.4 Hz, 1H), 3.71 (d, J=6.4 Hz, 1H), 3.65-3.63 (m, 2H), 3.31-3.26 (m, 2H), 1.41 (s, 9H).

Example 34B

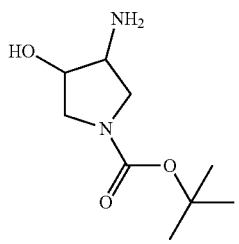

A solution of Example 34A (9.0 g, 48.59 mmol) in 90 ml ammonia water was heated to 90° C. and stirred for 4 hours. The reaction solution became reddish brown. The reaction solution was rotatory evaporated until dry, into which were added dichloromethane 200 ml and methanol 20 ml, the mixture was dried over anhydrous sodium sulfate, and filtered. The filtrate was concentrated to give the product Example 34B (8 g) as a reddish brown oil, which was used directly in the next step.

Example 34C

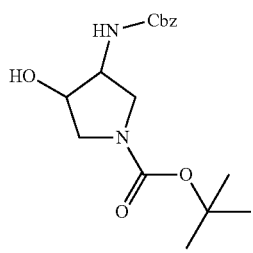 [SMILES: CC(C)(C)OC(=O)N1CC(O)C(NC(=O)OCc2ccccc2)C1]

To a mixed solution of Example 34B (2 g, 9.89 mmol) in 20 ml toluene and 10 ml water were added sodium carbonate (5.24 g, 49.45 mmol), and dropwise added benzyl chloroformate (2.53 g, 14.84 mmol) slowly. The reaction solution was stirred for 4 hours while the temperature was controlled at 10-20° C. The TLC detected the completely consumption of raw materials. To the reaction solution was added water 30 ml, the mixture was extracted with ethyl acetate (30 ml×2) for 2 times. The organic phases were combined, washed with saline (40 ml), and dried over anhydrous sodium sulfate. The filtrate was concentrated to give a crude product, which was purified over a flash silica gel column (dichloromethane:methanol=10:1) to give the product Example 34C (1.45 g, 43.59% yield) as a yellow oil.

$^1$HNMR (400 MHz, CHLOROFORM-d) δ=7.45-7.30 (m, 5H), 5.19-4.87 (m, 3H), 4.27 (br s, 1H), 4.00 (br s, 1H), 3.88-3.75 (m, 1H), 3.72-3.65 (m, 1H), 3.37-3.07 (m, 2H), 1.47 (s, 9H).

Example 34D

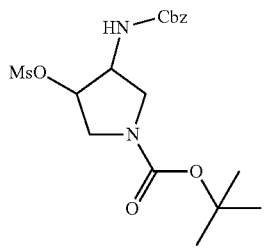 [SMILES: CC(C)(C)OC(=O)N1CC(NC(=O)OCc2ccccc2)C(OS(C)(=O)=O)C1]

To a solution of Example 34C (500 mg, 1.49 mmol) in 10 ml dichloromethane was added triethyl amine (0.41 ml, 2.98 mmol), to the reaction solution was then dropwise added methane sulfonyl chloride (256 mg, 2.24 mmol), the reaction solution was stirred at 10-20° C. for 1 hour. The TLC detected the completely consumption of raw materials. The reaction solution was quenched with 10 ml water, extracted with dichloromethane (20 ml×2) for 2 times. The organic phases were combined, washed with saline (20 ml), dried over anhydrous sodium sulfate, filtered and concentrated at reduced pressure to give Example 34D (670 mg, crude) as a yellow solid.

$^1$H NMR (400 MHz, METHANOL-d4) δ=7.31-7.13 (m, 5H), 5.06-4.87 (m, 3H), 4.15 (br s, 1H), 3.63-3.51 (m, 2H), 3.50-3.42 (m, 1H), 3.28-3.25 (br d, J=11.8 Hz, 1H), 3.07 (s, 3H), 1.42 (s, 9H)

Example 34E

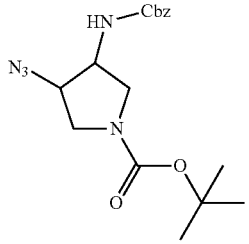 [SMILES: CC(C)(C)OC(=O)N1CC(N=[N+]=[N-])C(NC(=O)OCc2ccccc2)C1]

To a solution of Example 34D (600 mg, 1.45 mmol), sodium acetate (237.89 mg, 2.90 mmol) in 5 ml DMF was added sodium azide (282.79 mg, 4.35 mmol), the reaction solution was stirred at 100° C. for 3 hours. The TLC detected the completely consumption of raw materials. To the reaction solution was added 20 ml water, the mixture was extracted with ethyl acetate (20 ml×2) for 2 times. The organic phases were combined, washed with saline (30 ml), dried over anhydrous sodium sulfate to give about 35 ml a solution of Example 34E in ethyl acetate which was used directly in the next step.

Example 34F

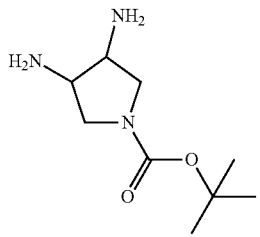

To a solution of Example 34E (00 mg, 35 ml ethyl acetate solution) in 30 ml methanol was added Pd/C (200 mg, dry) under the atmosphere of N2. The reaction solution was swept with hydrogen for 3 times, finally stirred at H$_2$ (40 psi) for 16 hours. The TLC detected the completely consumption of raw materials. The reaction solution became green, filtered and rotatory evaporated until dry to give 450 mg Example 34F (crude) as a light green oil.

$^1$HNMR (400 MHz, METHANOL-d4) δ=3.60-3.49 (m, 2H), 3.42-3.35 (m, 2H), 3.23-3.14 (m, 2H), 1.47 (s, 9H).

Example 34G

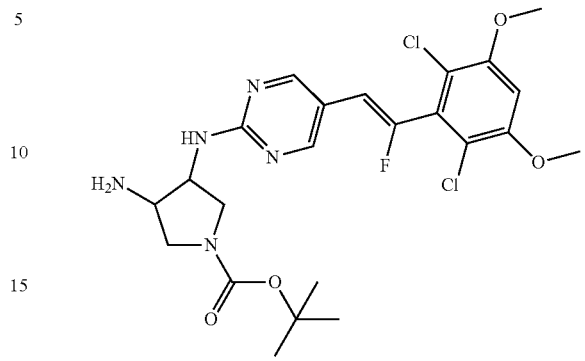

To a solution of Example 34F (166 mg, 0.83 mmol) in 3 ml dioxane were added DIEA (106.63 mg, 0.083 mmol), 2-chloro-5-[(Z)-2-(2,6-dichloro-3,5-dimethoxy-benzene)-2-fluoro-ethylene] pyridine (100 mg, 0.28 mmol). The reaction solution was reacted at 90-100° C. for 8 hours under the atmosphere of N$_2$. It was found from LCMS detection that product was generated, and the raw materials have been reacted completely. To the reaction solution was added 20 ml water, the mixture was extracted with ethyl acetate (20 ml×2) for 2 times. The organic phases were combined, washed with saline (20 ml), dried over anhydrous sodium sulfate, and filtered. The filtrate was rotate evaporated until dry to give a crude product, which was purified over a thin layer chromatography plate (petroleum ether:ethyl acetate=1:1) to give the product Example 34G (45 mg, 30.96% yield) as a colorless oil.

LCMS (ESI) m/z: 528.0 (M+1)$^+$

Example 34H

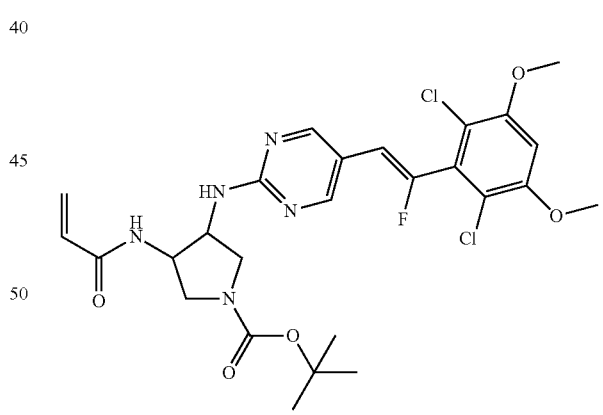

To a solution of Example 34G (30 mg, 56.78 μmol) in anhydrous dichloromethane (2 ml) were added DIEA (14.68 mg, 113.56 μmol), then added acryloyl chloride (0.23 ml, a dichloromethane solution at 0.25 mol/liter), and the mixture was stirred at 0-10° C. for 30 minutes. LCMS showed that the generation of the product and the completely consumption of raw materials. The reaction solution was quenched with water (5 ml), filtered, extracted with dichloromethane (20 ml), dried over anhydrous sodium sulfate, and then concentrated to give the crude product Example 34H (30 mg, crude) as a yellow oil.

LCMS (ESI) m/z: 582.1 (M+1)$^+$

Example 341

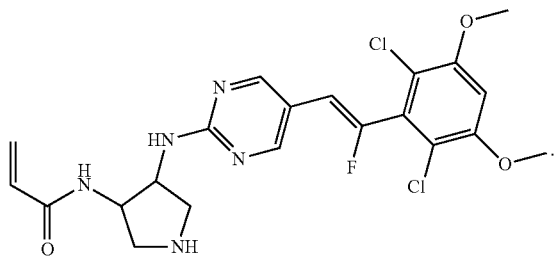 [SMILES: C=CC(=O)NC1CNCC1Nc1ncc(/C=C(\F)c2c(Cl)c(OC)cc(OC)c2Cl)cn1]

To Example 34H (30 mg, 51.51 μmol) was added HCl/EA (4 ml, 4 mol/l), and the mixture was stirred at 25-32° C. for 1 hour under the atmosphere of N2. LCMS showed that the generation of the product and the completely consumption of raw materials. The reaction solution was directly concentrated to give the product Example 341 as a colorless oil. LCMS (ESI) m/z: 482.1 (M+1)+

Example 34

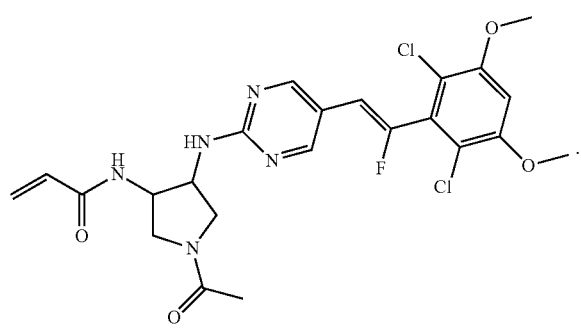 [SMILES: C=CC(=O)NC1CN(C(C)=O)CC1Nc1ncc(/C=C(\F)c2c(Cl)c(OC)cc(OC)c2Cl)cn1]

To a solution of Example 341 (20 mg, 41.47 μmol) in anhydrous dichloromethane (2 ml) were added DIEA (16.08 mg, 124.41 μmol), then added acetyl chloride (0.13 ml, a dichloromethane solution at 0.25 mol/l), and the mixture was stirred at 0-10° C. for 30 minutes. LCMS showed that the generation of the product and the completely consumption of raw materials. The reaction solution was quenched with water (10 ml), filtered, extracted with dichloromethane (20 ml), dried over anhydrous sodium sulfate, and concentrated to give a crude product as a yellow oil, which was purified over a chromatography plate (petroleum ether:ethyl acetate=1:1) to give the product Example 34 (2 mg, 8.35% yield). LCMS (ESI) m/z: 524.1 (M+1)+

Experiment Example 1: In Vitro Enzyme Activity Test of the Compounds of the Present Invention

Experiment Objectives

The inhibitory effects of the compounds on FGFR4 kinases were assessed by detecting the enzymatic activities through Z'-LYTE® Assay, with the $IC_{50}$ value of the compound as the indicator. This activity test was performed by Life technology.

Experimental Method

The test compounds were diluted in a concentration gradient of 3-times, the final concentrations were 10 concentrations ranging from 10 μM to 0.5 nM, with double hole for each concentration; the content of DMSO in the detection reaction was 1%.

FGFR4 Enzymatic Reaction:

1.94 to 84 ng FGFR1 protein kinase, 2 μM Tyr4 substrate, 150 μM ATP, 50 mM HEPES (pH 7.5), 0.01% BRIJ-35, 10 mM MgCl$_2$, 2 mM MnCl$_2$, 1 mM EGTA, 1 mM DTT. The detection plate was Bar-coded Corning, low volume NBS, black 384-well plate, reaction conducted at room temperature for 60 minutes, and the reaction system was 10μμL.

FGFR1 Enzymatic Reaction:

1 nM FGFR1 protein kinase, 2 μM Tyr4 peptide, 25 μM ATP, 50 mM HEPES (pH 7.5), 10 mM MgCl$_2$, 1 mM EGTA, 0.01% BRIJ-35, 2 mM MnCl$_2$, 1 mM DTT. The detection plate was Black Proxiplate 384-Plus plate (PerkinElmer), reaction conducted at room temperature for 60 minutes, and the reaction system was 10μμL.

Reaction Detection:

To the kinase reaction solution was added 5 μL Development reagent B (1:64) to stop the reaction and incubated at 23° C. for 60 minutes, reading the plate with Envision instrument.

Data Analysis

Data was transformed into the phosphorylation rate and the inhibitory rate by curve fitting with Model 205 in XLFIT (iDBS) to obtain the $IC_{50}$ data of the compounds. It was set as 0% if the bottom of the curve was not in the range of −20% to 20%; otherwise it was set as 100% if the top of the curve was not in the range of 70% to 130%.

TABLE 1

$IC_{50}$ test results of Z'-LYTE ™ detection

| Samples for test (the title compound) | FGFR4 | FGFR1 |
|---|---|---|
| Control example 1 | 8060 | >10,000 |
| Control example 2 | 14 | 2972 |
| Control example 3 | 408 | NA |
| Example 1 | 112 | >10,000 |
| Example 2 | 84 | >10,000 |
| Example 3 | 993 | >10,000 |
| Example 5 | 203 | N/A |
| Example 6 | 124 | >10,000 |
| Example 7 | 31 | >10,000 |
| Example 10 | 544 | N/A |
| Example 11 | 20.1 | 4,983.0 |
| Example 12 | 10.9 | 25.8 |
| Example 13 | 30.1 | 613.2 |
| Example 14 | 17.7 | 182.0 |
| Example 15 | 1.58 | 813.1 |
| Example 16 | 67.5 | 2,516.0 |
| Example 18 | 105 | 1,899.8 |
| Example 19 | 47 | 3,102.7 |
| Example 21 | 17 | 1,460.0 |
| Example 22 | 575 | N/A |
| Example 23 | 387 | N/A |
| Example 24 | 10 | 2,100.0 |
| Example 25 | 476 | 355.0 |
| Example 26 | 13 | N/A |
| Example 28 | 263 | 3,210.0 |
| Example 29 | 268 | N/A |
| Example 30 | 238 | N/A |
| Example 31 | 560 | >10,000 |
| Example 32 | 361 | N/A |
| Example 34 | 199 | N/A |
| Example 35 | 23 | 174.0 |

Note:
the unit was nM,
N/A indicates not detected.

Conclusion: A series of compounds of the present invention with high FGFR4 selectivity could be derived form the mother nuclear structure of acrylamide and fluorinated olefinic bond, which have superior inhibitory activities on FGFR4 kinases, while without activities on subtype FGFR1 kinases, the selectivity on FGFR4 kinases is at least more than ten or a hundred times than that on FGFR1 kinases. It was further found that in the structure of dimethoxy dichlorobenzene ring, the dichloro could enhance the inhibitory activity of FGFR4 greatly; for embodiment 1, the activity was enhanced by 70 times compared with the control example 1; a fluorine atom was introduced into the olefinic bond, and the fluorine atom was close to dichloroaniline, which could enhance the target activity of FGFR4, for example, the activity in embodiment 15 was enhanced by near 9 times compared with that in the control example 2, and the activity in embodiment 19 was enhanced by near 9 times compared with that in the control example 3.

Experiment Example 2: Pharmacokinetic Evaluation on the Compounds of the Present Invention Experimental process: A 1 mg/ml clear solution of the test compound in a solvent (see Table 2) was injected into the body of female Balb/c nude mice (ShangHai LingChang Biological Technology Co., Ltd.) via tail vein, with a dosage of 2 mg/kg. The test compound suspended in the corresponding solvent at 1 mg/ml was administered by gavage to female Balb/c nude mice (fasted overnight, at an age of 7-9 weeks), with a dosage of 10 mg/kg. Two groups of animals were both blood sampled about 30 μL from jugular vein or tail vein at 0.0833, 0.25, 0.5, 1.0, 2.0, 4.0, 6.0, 8.0 and 24 h post-administration, which was placed into an anticoagulant tube charged with EDTA-K2, and plasma was separated by centrifugation. Plasma concentrations were determined by LC-MS/MS process using WinNonlin™ Version 6.3 (Pharsight, Mountain View, Calif.) pharmacokinetic software, calculating the related pharmacokinetic parameters with a linear logarithmic trapezoidal method for non-atrioventricular models. The solvents used and the corresponding dosages were as shown in Table 2.

Experimental data results were as shown in Table 3:

TALBE 3

Pharmacokinetic experimental results of mice for each compound

| | IV | | | | PO | | | |
|---|---|---|---|---|---|---|---|---|
| | Cl (mL/min/kg) | Vdss (L/kg) | $T_{1/2}$ (h) | $AUC_{0-last}$ (nM · h) | $C_{max}$ (nM) | $T_{max}$ (h) | $AUC_{0-last}$ (nM · h) | F % |
| Example 16 | 23.9 | 1.2 | 0.676 | 2796 | 3290 | 0.5 | 5640 | 40.7 |
| Control example 4 | 77.1 | 0.533 | 0.114 | 958 | ND | ND | ND | ND |
| Example 24 | 50.0 | 1.82 | 0.549 | 1317 | 282 | 0.500 | 962 | 14.8 |
| Control example 5 | 127 | 1.28 | 0.221 | 528 | ND | ND | ND | ND |
| Control example 6 | 186 | 2.44 | 0.235 | 388 | ND | ND | ND | ND |
| Example 21 | 48.2 | 0.723 | 0.291 | 1423 | 1123 | 0.25 | 1073 | 20.4 |
| Control example 7 | 65 | 0.581 | 0.109 | 113 | ND | ND | 0 | 0 |
| Control example 8 | 39.7 | 0.407 | 0.154 | 1798 | 2710 | 0.25 | 1104 | 12.3 |

Note:
Plasma clearance (CL) mL/min/kg,
Steady-state apparent volume of distribution (Vdss) L/kg,
Elimination half-life ($T_{1/2}$) and
Area under plasma concentration curve from point 0 to the last quantifiable time point ($AUC_{0-last}$)
Bioavailability F %,
Peak concentration ($C_{max}$) nM,
Time to peak Tmax (h)
ND: Not detected.

TABLE 2

Pharmacokinetic experimental conditions of mice for each compound

| | Tail Vein Administration (IV) | | Oral Gavage (PO) | |
|---|---|---|---|---|
| | Dosage | Solvent | Dosage | Solvent |
| Example 16 | 2 mg/kg | 1 mg/ml in dimethyl sulfoxide: polyoxyethylene castor oil: water = 5:5:90, supernatant | 10 mg/kg | 1 mg/ml in dimethyl sulfoxide: polyoxyethylene castor oil: water = 5:5:90, supernatant |
| Control example 4 | 2 mg/kg | 1 mg/ml in dimethyl sulfoxide: polyoxyethylene castor oil: water = 5:5:90, supernatant | 10 mg/kg | 1 mg/ml in dimethyl sulfoxide: polyoxyethylene castor oil: water = 5:5:90, supernatant |
| Example 24 | 2 mg/kg | 1 mg/ml in dimethyl sulfoxide: castor oil: water = 5:5:90, supernatant | 10 mg/kg | 1 mg/ml, a uniform suspension of 0.5% sodium methyl celluose + 1% Tween 80 |
| Control example 5 | 2 mg/kg | 1 mg/ml in dimethyl sulfoxide: polyoxyethylene castor oil: water = 5:15:80, supernatant | 10 mg/kg | 1 mg/ml, a uniform suspension of 0.5% sodium methyl celluose + 0.2% Tween 80 |
| Control example 6 | 2 mg/kg | 1 mg/ml in dimethyl sulfoxide: polyoxyethylene castor oil: water = 10:40:50, supernatant | 10 mg/kg | 1 mg/ml, a uniform suspension of 0.5% sodium methyl celluose + 1% Tween 80 |
| Example 21 | 2 mg/kg | 1 mg/ml in dimethyl sulfoxide: polyoxyethylene castor oil: water = 05:5:90, supernatant | 10 mg/kg | 1 mg/ml, a uniform suspension of 0.5% sodium methyl celluose + 1% Tween 80 |
| Control example 7 | 0.2 mg/kg | 1 mg/ml in dimethyl sulfoxide: 20% cyclodextrin = 5:95, supernatant | 1.0 mg/kg | 1 mg/ml, a uniform suspension of 0.5% sodium methyl celluose + 1% Tween 80 |
| Control example 8 | 2 mg/kg | 1 mg/ml in dimethyl sulfoxide: polyoxyethylene castor oil: water = 5:5:90, supernatant | 10 mg/kg | 1 mg/ml, a uniform suspension of 0.5% sodium methyl celluose + 0.2% Tween 80 |

125

Experimental Conclusion

It can be seen from the experimental results that compared with the control example 4 with a benzyl ether structure, the plasma clearance (CL) of Example 16 with a fluorine olefin structure was 23.9 mL/min/kg, with the stability enhanced by 3 times, meanwhile the oral absorption ratio of the drug was increased from 0% to more than 40%; compared with the control example 5 and the control example 6 with a benzyl ether structure, the plasma clearance (CL) of Example 24 with a fluorine olefin structure was 50 mL/min/kg, with the stabilities enhanced by 2 to more than 3 times respectively, meanwhile the oral absorption ratio of the drug was increased from 0% to 14.8%. Compared with the control example 7 and the control example 8, Example 21 also exhibited a great enhancement in terms of bioavailability. Above all, the fluorine olefin structure of the compound of the present invention, compared with the benzyl ether structure, was capable of greatly enhancing the metabolic stability of the drugs, while also greatly enhancing the oral absorption bioavailability of the drugs.

Experiment Example 3: Analysis on Tumor Growth Inhibition (TGI)

The evolutionary growth potential of a tumor was assessed by the relationship between the volume of the tumor and time. The long axis (L) and short axis (W) of a subcutaneous tumor were determined by a caliper twice a week, the tumor volume (TV) was calculated by the formula of $((L \times W^2)/2)$. TGI was calculated by the difference value between the median of tumor volumes of mice in the solvent group and the median of tumor volumes of mice in the drug group, and represented by the percentage accounting for the median of tumor volumes in the solvent control group, Calculated by the following formula:

% TGI=((the median of tumor volume (control group)−the median of tumor volume (dosing group))/the median of tumor volume (control group))×100%

The original statistical analysis was completed by the analysis of repeated variance determination. Subsequently, multiple comparisons were performed by a Scheffe psot hoc experimental method. Single solvent (0.5% methylcellulose+1% aqueous solution of Tween) was the negative control. The experimental results were as seen in Table 4:

TABLE 4

Results of Antitumor Activity Test of Mice in Vivo

| | Hep3B Transplantation Models | TGI % (dosing on Day 21 for the last time) |
|---|---|---|
| Example 7 | 30 mg/kg BID | 108% |
| Example 16 | 100 mg/kg, BID | 89% |
| Example 21 | 100 mg/kg, BID | 106% |

Note:
BID: twice a day.

Conclusion: The compounds of the present invention could be used as small molecule tyrosine kinase inhibitors due to their excellent in vitro inhibitory activities on FGFR4 enzymes, which have superior antitumor activities and have good effects on treating neoplastic diseases of various mammals (including human), such as liver cancer, gastric cancer, etc.

126

The invention claimed is:

1. A compound as shown in formula (I), a pharmaceutically acceptable salt or a tautomer thereof,

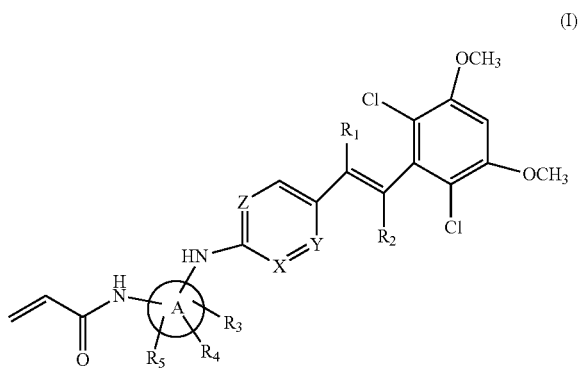

(I)

wherein, each of X, Y, Z is independently selected from the group consisting of C(R) and N;

one of $R_1$ and $R_2$ is F, and the other is H or $CH_3$;

A-ring is selected from the group consisting of phenyl, 5-6 membered cycloalkyl, 5-6 membered heterocycloalkyl;

each of $R_3$, $R_4$, $R_5$ is independently selected from the group consisting of H, F and Cl, or selected from the group consisting of $C_{1-3}$ alkyl, $C_{1-3}$ alkoxy, $C_{1-3}$ alkyl-C(=O)—, 5-6 membered heterocycloalkyl which are optionally substituted with 1, 2 or 3 R;

R is H, or selected from the group consisting of $C_{1-3}$ alkyl, $C_{1-3}$ alkyl-C(=O)— and 5-6 membered heterocycloalkyl which are optionally substituted with 1, 2 or 3 R';

R' is selected from the group consisting of $CH_3$ and —$CH_2CH_3$;

the 5-6 membered heterocycloalkyl comprises heteroatoms selected from the group consisting of —NH—, —O— and N;

in any one of the above cases, the number of heteroatoms is independently selected from the group consisting of 1, 2 and 3.

2. The compound, the pharmaceutically acceptable salt or the tautomer thereof according to claim 1, wherein R is H, or selected from the group consisting of $CH_3$, —$CH_2CH_3$,

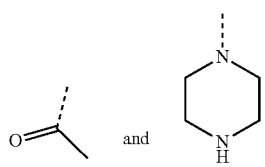

which are optionally substituted with 1, 2 or 3 R'.

3. The compound, the pharmaceutically acceptable salt or the tautomer thereof according to claim 2, wherein R is selected from the group consisting of H, $CH_3$, —$CH_2CH_3$,

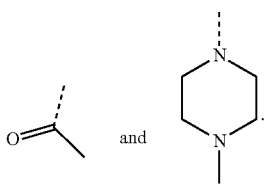 and

4. The compound, the pharmaceutically acceptable salt or the tautomer thereof according to claim 1, wherein A-ring is selected from the group consisting of phenyl, cyclohexyl, cyclopentyl, tetrahydropyranyl, tetrahydrofuryl and pyrrolidinyl.

5. The compound, the pharmaceutically acceptable salt or the tautomer thereof according to claim 4, wherein A-ring is selected from the group consisting of

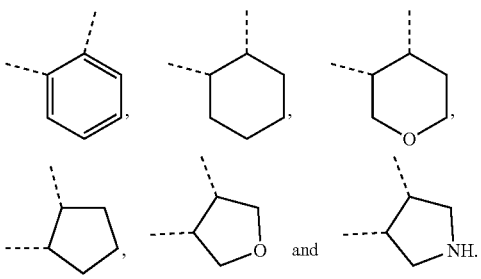

6. The compound, the pharmaceutically acceptable salt or the tautomer thereof according to claim 1, wherein the structural unit

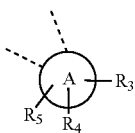

is selected from the group consisting of

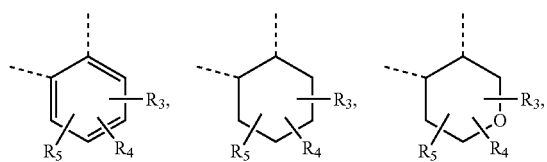

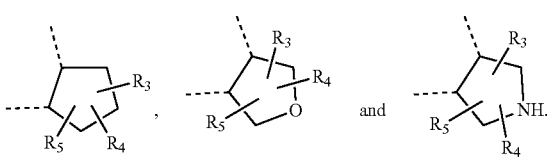 and

7. The compound, the pharmaceutically acceptable salt or the tautomer thereof according to claim 6, wherein the structural unit

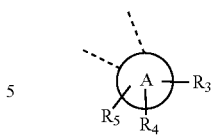

is selected from the group consisting of

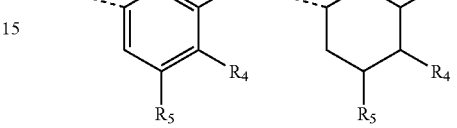

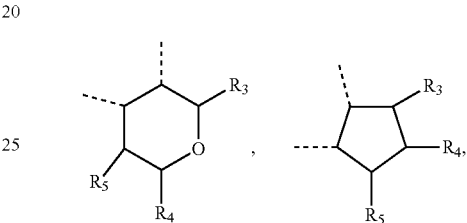

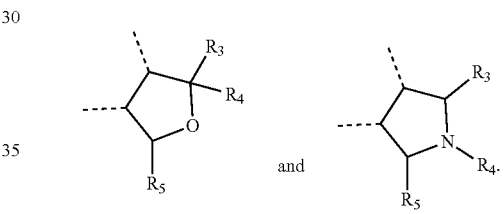 and

8. The compound, the pharmaceutically acceptable salt or the tautomer thereof according to claim 7, wherein the structural unit

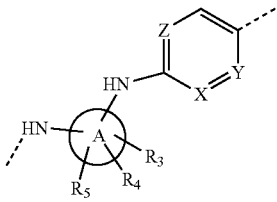

is selected from the group consisting of

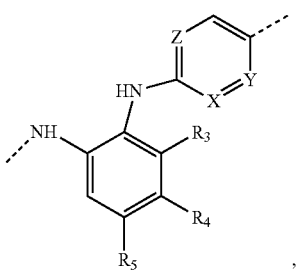

-continued

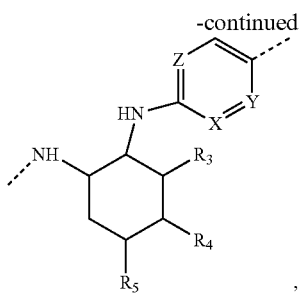,

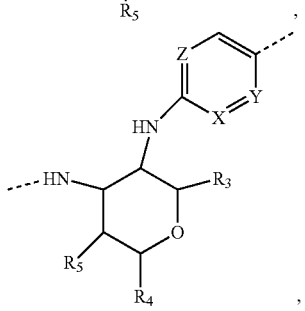,

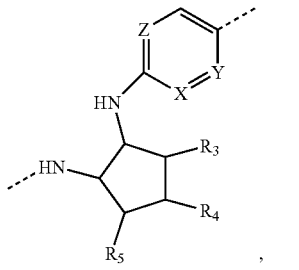,

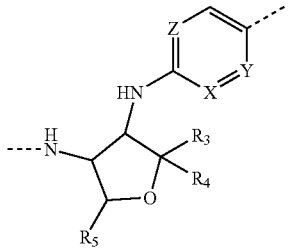 and

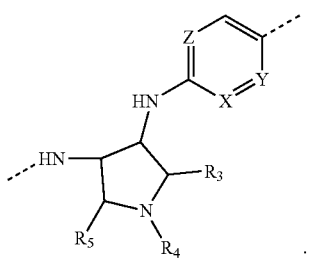.

9. The compound, the pharmaceutically acceptable salt or the tautomer thereof according to claim 1, wherein the structural unit

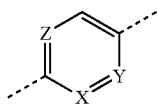

is selected from the group consisting of

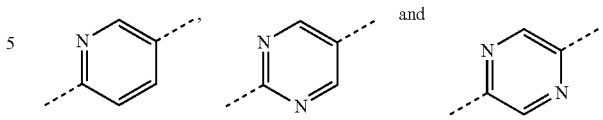

or, each of $R_3$, $R_4$, $R_5$ is independently selected from the group consisting of H, F and Cl, or selected from the group consisting of methyl, ethyl, $C_{1-3}$ alkoxy, $C_{1-3}$ alkyl-C(=O)— and piperazinyl which are optionally substituted with 1, 2 or 3 R.

10. The compound, the pharmaceutically acceptable salt or the tautomer thereof according to claim 9, wherein each of $R_3$, $R_4$, $R_5$ is independently selected from the group consisting of H, F and Cl, or selected from the group consisting of $CH_3$,

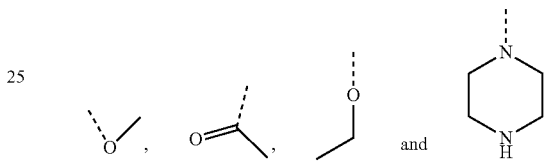

which are optionally substituted with 1, 2 or 3 R.

11. The compound, the pharmaceutically acceptable salt or the tautomer thereof according to claim 10, wherein each of $R_3$, $R_4$, $R_5$ is independently selected from the group consisting of H, F, Cl, $CH_3$,

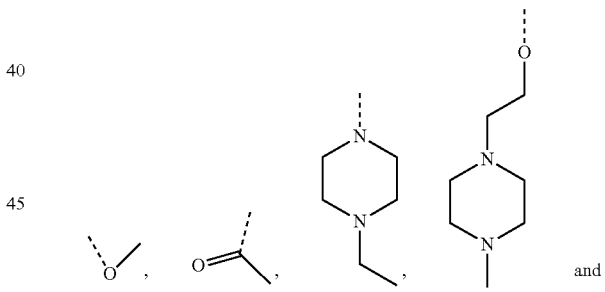

12. The compound, the pharmaceutically acceptable salt or the tautomer thereof according to claim 11, wherein $R_3$ is selected from the group consisting of H, F, Cl and $CH_3$, or, $R_4$ is selected from the group consisting of H, F, Cl,

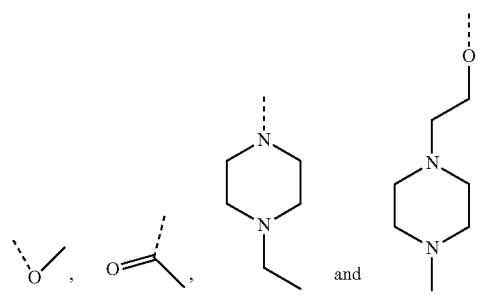
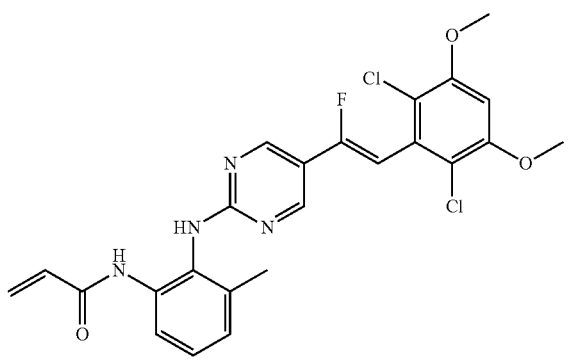
13. The compound, the pharmaceutically acceptable salt or the tautomer thereof according to claim 11, wherein R₅ is selected from the group consisting of H, F, Cl,
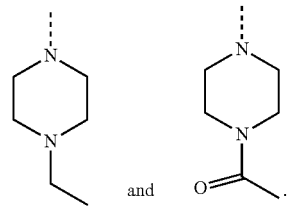
14. A compound, a pharmaceutically acceptable salt or a tautomer thereof, which is selected from the group consisting of
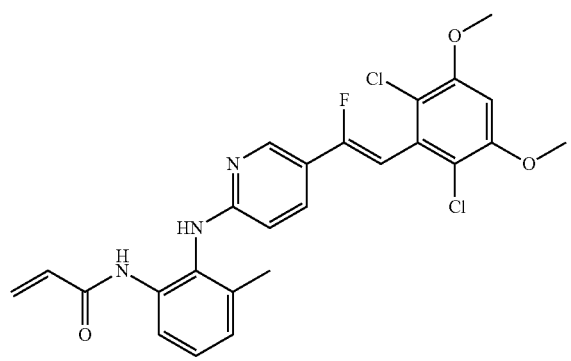
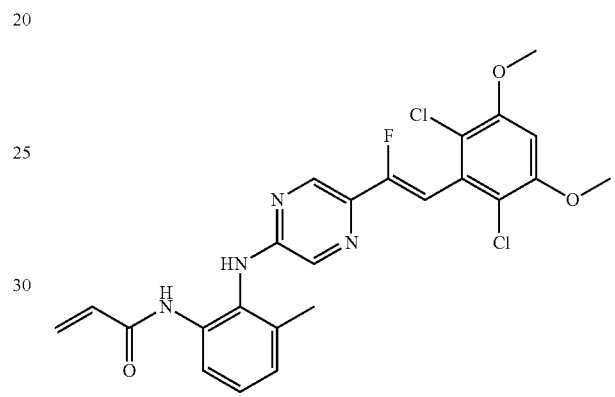
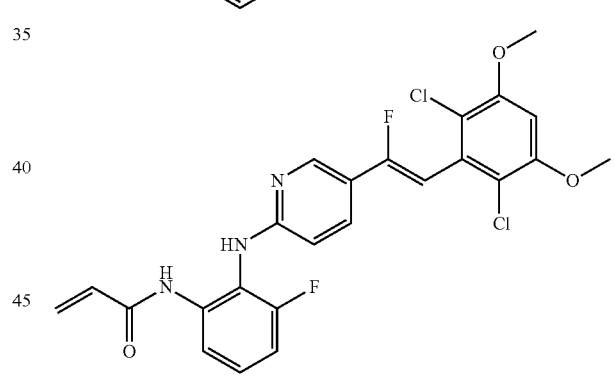
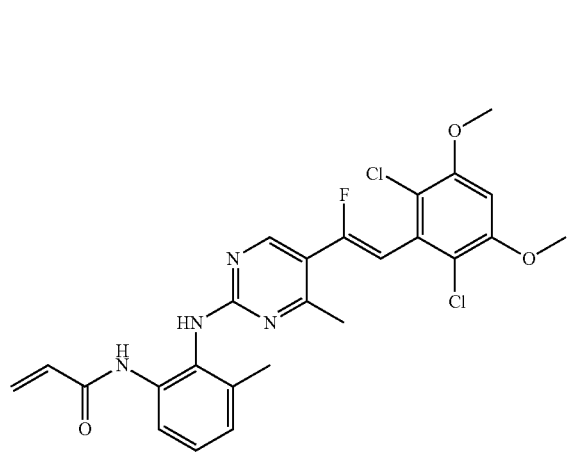
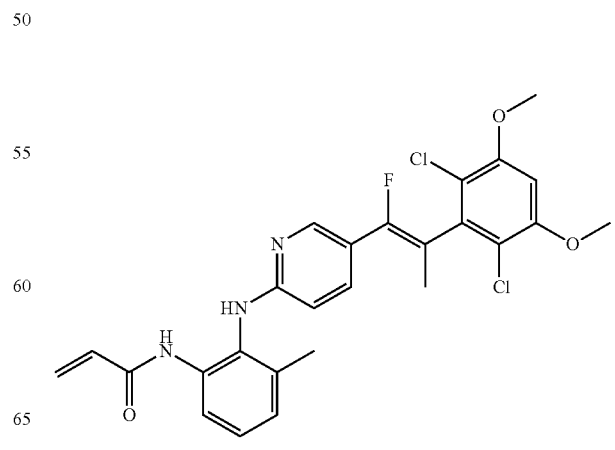

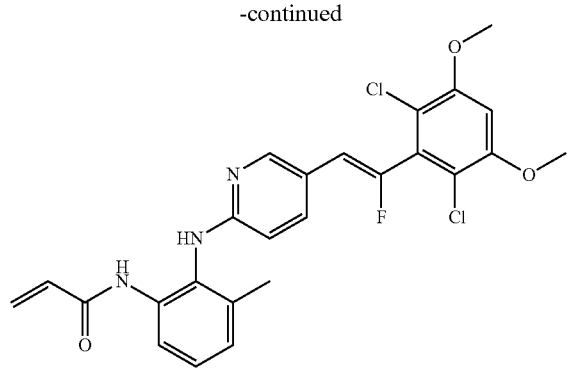
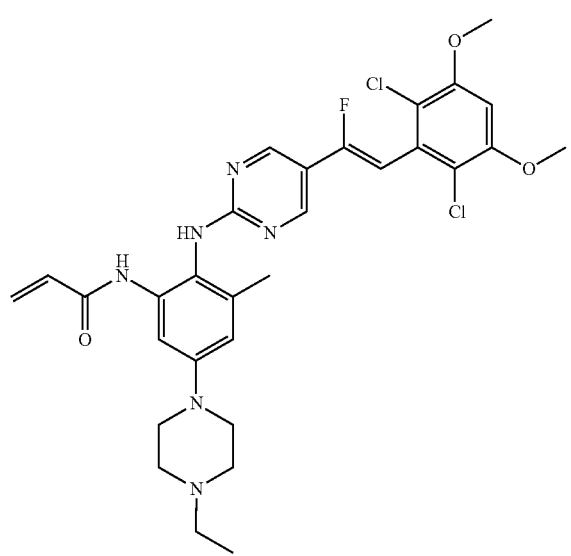
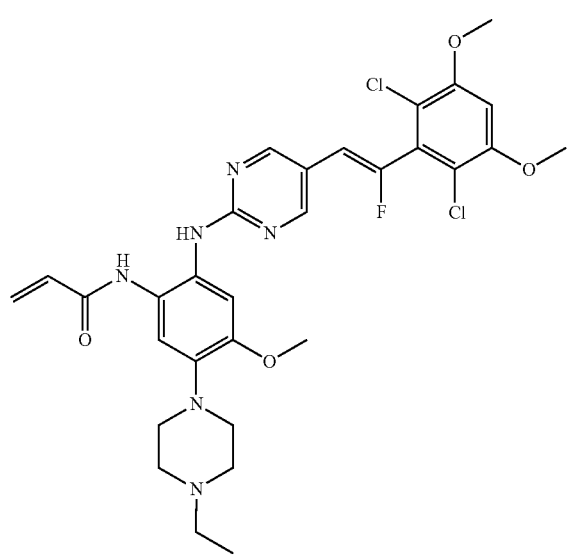
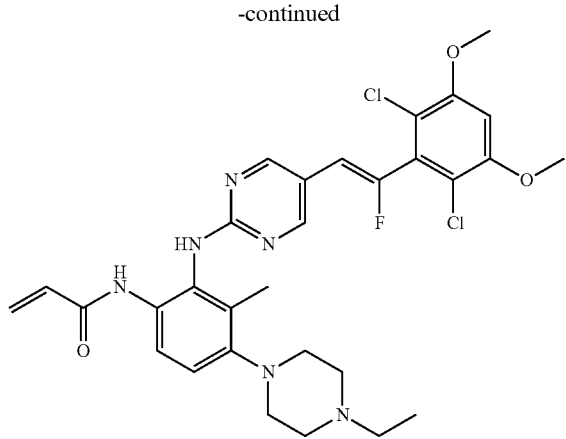
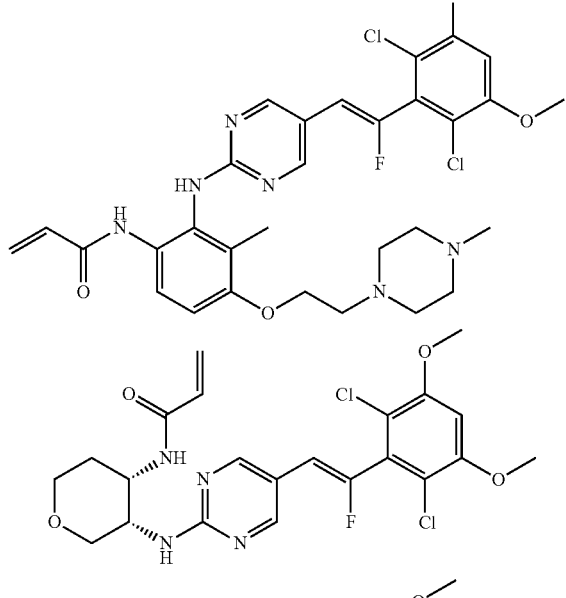
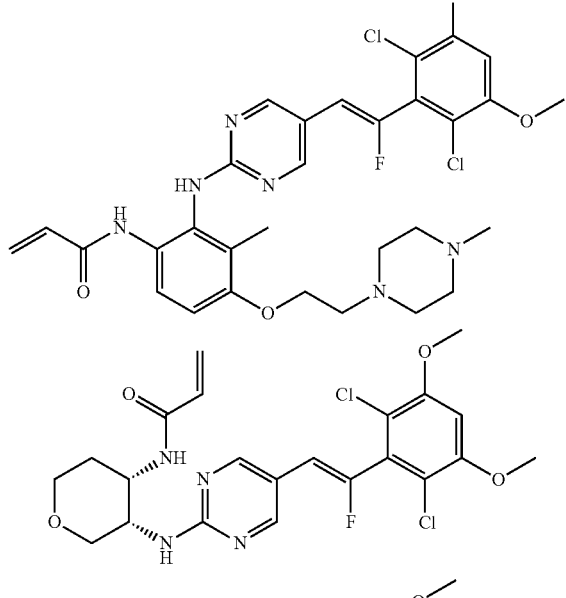
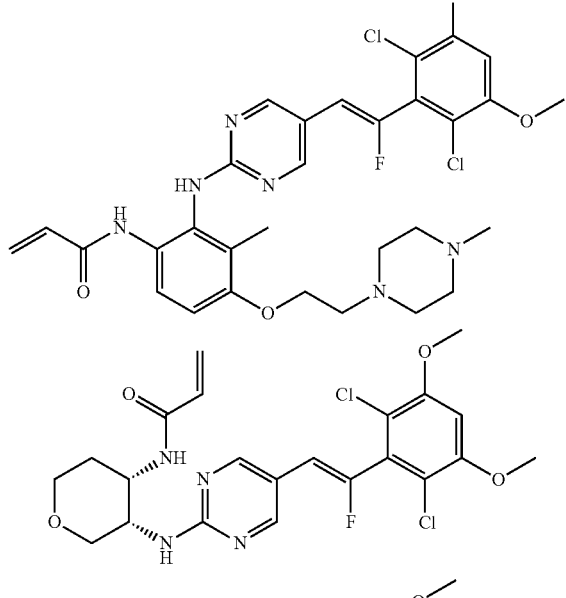
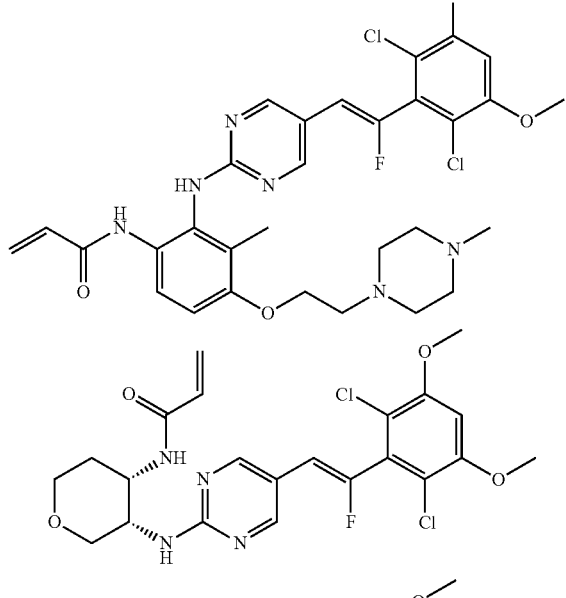

135
-continued
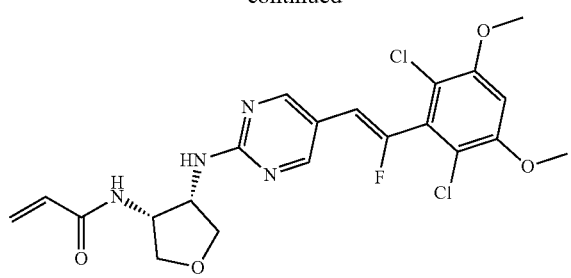
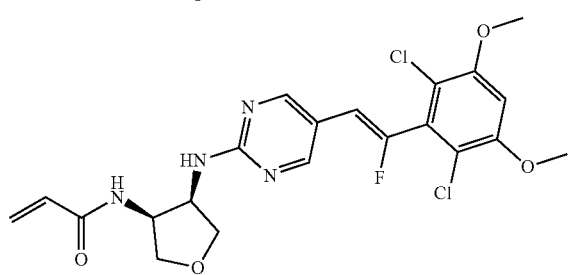
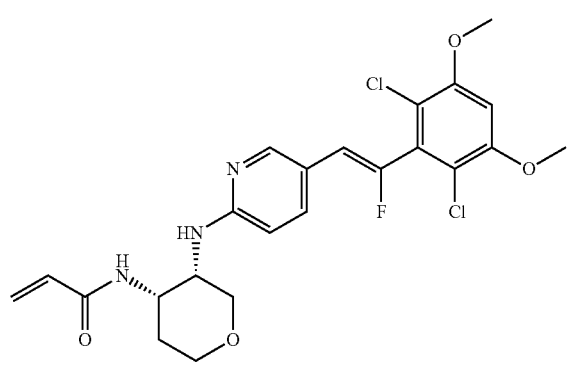
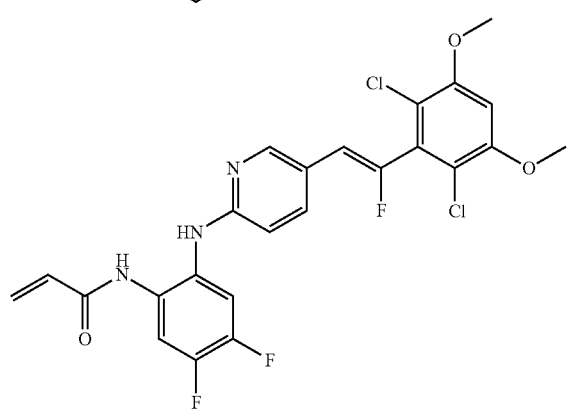
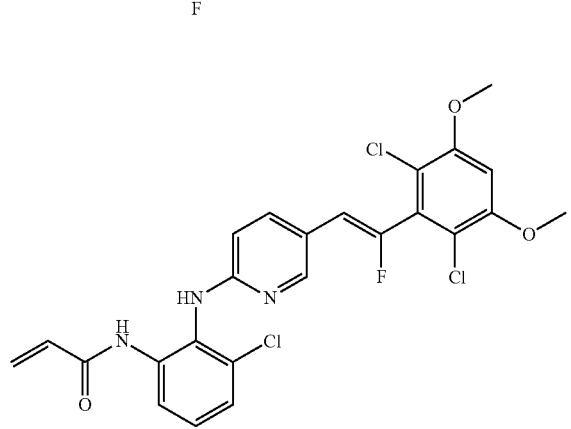
136
-continued
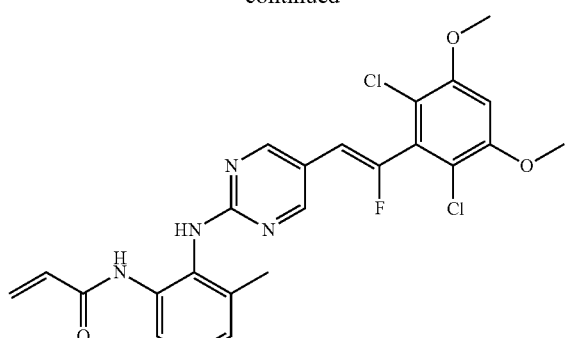
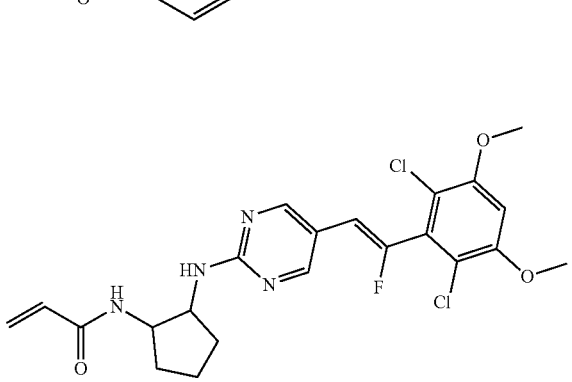
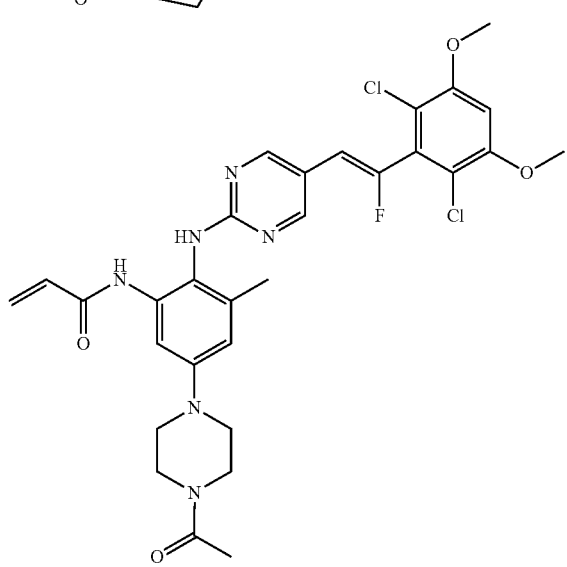
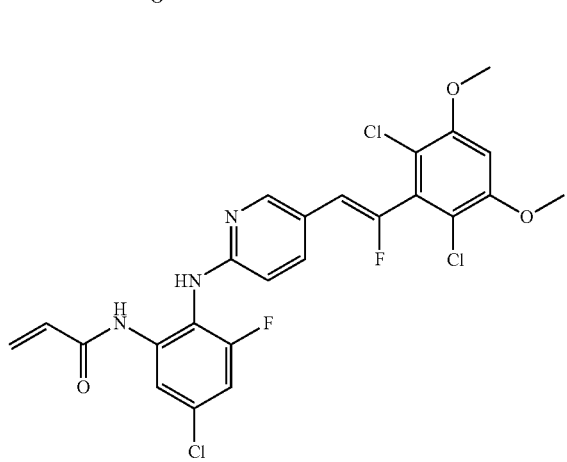

-continued
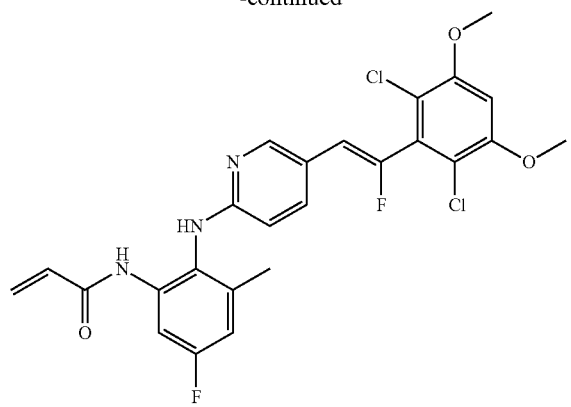
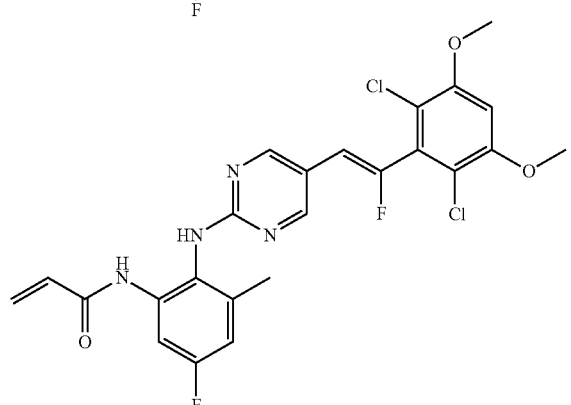
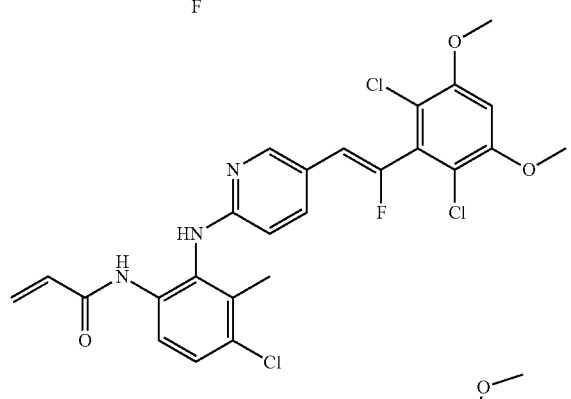
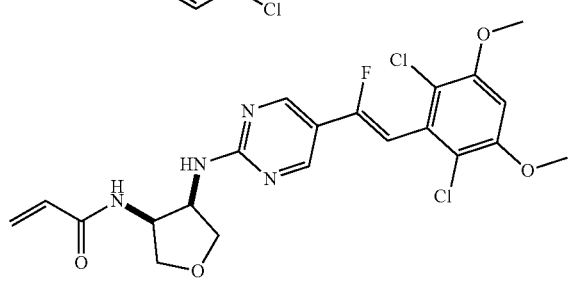
-continued
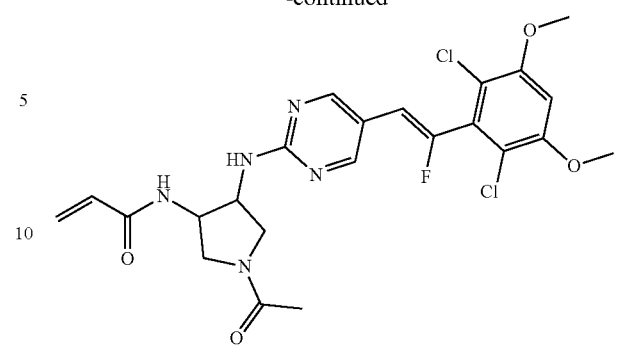
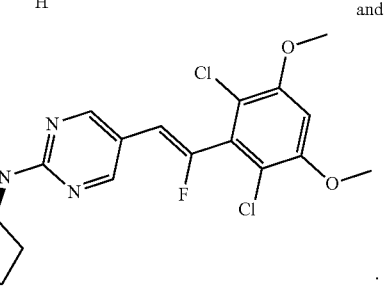
and
15. A pharmaceutical composition, comprising a therapeutically effective amount of the compound or the pharmaceutically acceptable salt thereof according to claim 1 as an active ingredient, as well as a pharmaceutically acceptable carrier.
* * * * *